United States Patent
Barreira Da Silva et al.

(10) Patent No.: US 11,883,398 B2
(45) Date of Patent: *Jan. 30, 2024

(54) DIPEPTIDYLPEPTIDASE 4 INHIBITION ENHANCES LYMPHOCYTE TRAFFICKING, IMPROVING BOTH NATURALLY OCCURRING TUMOR IMMUNITY AND IMMUNOTHERAPY

(71) Applicants: INSTITUT PASTEUR, Paris (FR); INSTITUT NATIONAL DE LA SANTE ET DE LA RECHERCHE MEDICALE (INSERM), Paris (FR)

(72) Inventors: Rosa Barreira Da Silva, San Francisco, CA (US); Matthew Albert, Paris (FR)

(73) Assignees: INSTITUT PASTEUR, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/551,379

(22) Filed: Dec. 15, 2021

(65) Prior Publication Data

US 2022/0117960 A1  Apr. 21, 2022

Related U.S. Application Data

(60) Continuation of application No. 15/930,166, filed on May 12, 2020, now Pat. No. 11,229,645, which is a
(Continued)

(51) Int. Cl.
*A61K 31/4985* (2006.01)
*A61K 31/513* (2006.01)
(Continued)

(52) U.S. Cl.
CPC .......... *A61K 31/4985* (2013.01); *A61K 31/40* (2013.01); *A61K 31/4545* (2013.01); *A61K 31/513* (2013.01); *A61K 31/522* (2013.01); *A61K 35/17* (2013.01); *A61K 39/001129* (2018.08); *A61K 45/06* (2013.01); *A61P 35/00* (2018.01); *A61K 31/403* (2013.01); *A61K 31/4375* (2013.01); *A61K 31/69* (2013.01); *A61K 39/0011* (2013.01); *A61K 39/00117* (2018.08); *A61K 39/00119* (2018.08); *A61K 39/001104* (2018.08); *A61K 39/001106* (2018.08); *A61K 39/001112* (2018.08); *A61K 39/001124* (2018.08); *A61K 39/001126* (2018.08); *A61K 39/001135* (2018.08); *A61K 39/001151* (2018.08); *A61K 39/001156* (2018.08); *A61K 39/001157* (2018.08); *A61K 39/001171* (2018.08); *A61K 39/001181* (2018.08); *A61K 39/001182* (2018.08); *A61K 39/001186* (2018.08); *A61K 39/001188* (2018.08); *A61K 39/001191* (2018.08);
(Continued)

(58) Field of Classification Search
CPC ................ A61K 31/4985; A61K 31/40; A61K 31/4545; A61K 31/513; A61K 31/522; A61K 39/395; A61K 39/001129; A61K 35/17; A61K 31/403; A61K 31/4375
See application file for complete search history.

(56) References Cited

U.S. PATENT DOCUMENTS 5,595,756 A * 1/1997 Bally .................. A61K 9/1272
264/4.1
6,699,871 B2  3/2004 Edmondson et al.
(Continued)

FOREIGN PATENT DOCUMENTS

WO  2006/119260 A2  11/2006
WO  2007/050485 A2  5/2007
(Continued)

OTHER PUBLICATIONS

Pech et al. Dipeptidyl Peptidase-4 Inhibition May Stimulate Progression of Carcinoid Tumor. Case Reports in Endocrinology, vol. 2015, Article ID 95019:1-4 (Year: 2015).*
Vangoitsenhoven et al. GLP1 and cancer: Friend or foe? Endocrine-Related Cancer (2012) 19 F77-F88 (Year: 2012).*
Topalian et al. Safety, Activity, and Immune Correlates of Anti-PD-1 Antibody in Cance. New England Journal of Medicine. 2012; 366(26): 2443-2454 (Year: 2012).*
Heppner et al. Tumor jeterogeneity:biological implications and therapeutic consequences. Cancer Metastasis Review 2:5-23; 1983 (Year: 1983).*
Sporn et al. Chemoprevention of Cancer. Carcinogenesis, vol. 21 (2000), 525-530 (Year: 2000).*
(Continued)

*Primary Examiner* — Vanessa L. Ford
*Assistant Examiner* — Sandra Dillahunt
(74) *Attorney, Agent, or Firm* — Arrigo, Lee, Guttman & Mouta-Bellum LLP

(57) ABSTRACT

The success of anti-tumor immune responses requires effector T cells to infiltrate solid tumors, a process guided by chemokines. Herein, we demonstrate that in vivo post-translational processing of chemokines by dipeptidylpeptidase 4 (DPP4, also known as CD26) limits lymphocyte migration to sites of inflammation and tumors. Inhibition of DPP4 enzymatic activity enhanced tumor rejection by preserving biologically active CXCL10, and increasing trafficking into the tumor by lymphocytes expressing the counter-receptor CXCR3. Furthermore, DPP4 inhibition improved adjuvant-based immunotherapy, adoptive T cell transfer and checkpoint blockade. These findings provide the first direct in vivo evidence for controlling lymphocyte trafficking through CXCL10 cleavage and support the use of DPP4 inhibitors for stabilizing the biologically active form of chemokines as a strategy to enhance tumor immunotherapy.

21 Claims, 44 Drawing Sheets

Related U.S. Application Data division of application No. 15/750,098, filed as application No. PCT/EP2015/079663 on Dec. 14, 2015, now Pat. No. 11,000,521.

(60) Provisional application No. 62/200,186, filed on Aug. 3, 2015.

(51) Int. Cl.

| | | |
|---|---|---|
| *A61K 31/522* | (2006.01) | |
| *A61K 35/17* | (2015.01) | |
| *A61K 31/4545* | (2006.01) | |
| *A61K 31/40* | (2006.01) | |
| *A61K 45/06* | (2006.01) | |
| *A61K 39/00* | (2006.01) | |
| *A61P 35/00* | (2006.01) | |
| *A61K 31/403* | (2006.01) | |
| *A61K 31/69* | (2006.01) | |
| *A61K 31/4375* | (2006.01) | |
| *A61K 47/68* | (2017.01) | |

(52) U.S. Cl.
CPC .............. *A61K 39/001192* (2018.08); *A61K 39/001193* (2018.08); *A61K 39/001194* (2018.08); *A61K 39/001195* (2018.08); *A61K 47/6803* (2017.08); *A61K 2039/55561* (2013.01); *A61K 2300/00* (2013.01)

(56) References Cited

U.S. PATENT DOCUMENTS

| | | | |
|---|---|---|---|
| 9,073,930 B2 | 7/2015 | Weber et al. | |
| 2011/0046071 A1* | 2/2011 | Karasik ................ | A61K 31/704 514/19.3 |

FOREIGN PATENT DOCUMENTS

| | | |
|---|---|---|
| WO | 2013/054307 A2 | 4/2013 |
| WO | 2013/054307 A9 | 4/2013 |
| WO | 2013/078059 A1 | 5/2013 |

OTHER PUBLICATIONS

Auerbach et al. Angiogenesis assays: problems and pitfalls. Cancer and Metastasis Reviews, 2000, 19: 167-172 (Year: 2000).*
Gura T. Systems for identifying new drugd are often faulty. Science, 1997, 278(5340): 1041-1042 (Year: 1997).*
Jain RK. Barriers to drug delivery in solid tumors. Scientific American, Jul. 1994,58-65 (Year: 1994).*
Hait. Anticancer drug development: the grand challenges. Nature Reviews/Drug Discovery, 2010, 9, pp. 253-254 (Year: 2010).*
Gravanis et al. The changing world of cancer drug development: the regulatory bodies' perspective. Chin Clin Oncol, 2014, 3, pp. 1-5 (Year: 2014).*
Beans. Targeting metastasis to halt cancer's spread. PNAS 2018; 115(50): 12539-12543 (Year: 2018).*
NCT01928394. Bristol-Myers Squibb. A study of nivolumab by itself or nivolumab in combination with Ipilimumab in patients with advanced or metastatic solid tumors. Available from: https://clinicaltrials.gov/ct2/show/NCT01928394. NLM identifier. NCT 01928394. First posted Aug. 23, 2013 (Year: 2013).*
Hodi et al. Improved Survival with Ipilimumab in Patients with Metastatic Melanoma. N Engl J Med 2010; 363:711-723) (Year: 2010).*
Barreira da Silva et al. Dipeptidylpeptidase 4 inhibition enhances lymphocyte trafficking, improving both naturally occurring tumor immunity and immunotherapy. Nature Immunology, published inline Jun. 15, 2015; 16(8):850-860 (Year: 2015).*
Wang et al. (2013) Berberine Inhibits Proliferation and Down-Regulates Epidermal Growth Factor Receptor through Activation of Cbl in Colon Tumor Cells. PLoS ONE 8(2): e56666 (Year: 2013).*
NCT02060188. Bristol-Myers Squibb. A Study of Nivolumab Alone or Nivolumab Combination Therapy in Colon Cancer That Has Come Back or Has Spread (CheckMate 142). Available from: https://clinicaltrials.gov/ct2/show/NCT 02060188. NLM identifier. NCT 02060188. First posted Feb. 11, 2014 (Year: 2014).*
Rosa Barreira da Silva, et al., "Dipeptidylpeptidase 4 inhibition enhances lymphocyte trafficking, improving both naturally occurring tumor immunity and immunotherapy," Nature Immunology, vol. 16, No. 8, pp. 850-858.
Agnieszka Sliwinska, et al., Metformin, but not sitagliptin, enhances WP 631-induced apoptotic HepG2 cell death, Toxicology in Vitro, vol. 29, pp. 1116-1123 (2015).
International Search Report and Written Opinion, PCT/EP2015/079663, dated Feb. 5, 2016.
Bristol-Myers Squibb. A study of nivolumab by itself or mivolumab in combination with Ipilimumab in patients with advanced or metastatic solid tumors. Available from: https://clinicaltrials.gov/ct2/show/NCT01928394. NLM identifier. NCT 01928394. First posted Aug. 23, 2013 (Year: 2013).
Eubank et al. Cancer Research, 2009; 69(5): 2133-2140 (Year: 2009).
Bowie et al. Science, 1990, 247:1306-1310 (Year: 1990).
Burgess et al. J. Cell Biol. 111 :2129-2138, 1990 (Year: 1990).
Lazar et al. Mol. Cell. Biol., 8:1247-1252, 1988 (Year: 1988).
Bork. Genome Research, 2000; 10:398-400 (Year: 2000).
Bowie et al. Deciphering the Message in Protein Sequences: Tolerance to Amino Acid Substitutions. Science, 1990, 247: 1306-1310 (Year: 1990).
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111 :2129-2138, 1990 (Year: 1990).
Bork. Powers and Pitfalls in Sequence Analysis: The 70% Hurdle. Genome Research, 2000; 10:398-400 (Year: 2000).
Maccallum et al. Antibody-antigen Interactions: Contact Analysis and Binding Site Topography. Journal of Molecular Biology, 262: 732-7 45, 1996 (Year: 1996).
Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002;320(2):415-28 (Year: 2002).
Lazar et al. Transforming Growth Factor alpha: Mutation of Aspartic Acid 47 and Leucine 48 Results in Different Biological Activities. Mol. Cell. Biol., 8:1247-1252, 1988 (Year: 1988).
Barreira da Silva et al. DPP4 inhibition enhances lymphocyte trafficking, improving both naturally occurring tumor immunity and immunotherapy. Nature Immunology, published online Jun. 15, 2015; 16(8):850-860. (Year: 2015).
Zhang et al. (In: Proceedings of the 103rd Annual Meeting of the American Association for Cancer Research; Mar. 31-Apr. 4, 2012; Chicago, IL. Philadelphia (PA): AACR; Cancer Res 2012;72(8. Suppl): Abstract nr 5226 (Year: 2012).
Hara et al. Interleukin-2 potentiation of cetuximab antitumor activity for epidermal growth factor receptoroverexpressing gastric cancer xenografts through antibody-dependent cellular cytotoxicity. Cancer Sci, 2008; 99(7): 1471-1478. (Year: 2008).
Beckenkamp A, Willig JB, Santana Nascimento J, Paccez JD, Zerbini LF, et al. (2015) Differential Expression and Enzymatic Activity of DPPIV/CD26 Affects Migration Ability of Cervical Carcinoma Cells. PLoS ONE 10(7): e0134305. doi:10.1371/journal.pone.0134305.
Nathalie Vigneron, "Human Tumor Antigens and Cancer Immunotherapy," BioMed Research International vol. 2015, Article ID 948501, 17 pages.
Brynn B. Duncan, et al., "A pan-inhibitor of DASH family enzymes induces immune mediated regression of murine sarcoma and is a potent adjuvant to dendritic cell vaccination and adoptive T-cell therapy," J Immunother. Oct. 2013;. 36(8): . doi:10.1097/CJI.0b013e3182a80213.
Robert M Eager, "Phase II assessment of talabostat and cisplatin in second-line stage IV melanoma," BMC Cancer 2009, 9:263 doi:10.1186/1471-2407-9-263.

(56) References Cited

OTHER PUBLICATIONS

Angelo Pietro Femia, et al., "Long-term treatment with Sitagliptin, a dipeptidyl peptidase-4 inhibitor, reduces colon carcinogenesis and reactive oxygen species in 1,2-dimethylhydrazine-induced rats," Int. J. Cancer: 133, 2498-2503 (2013).

Harald Herrmann, et al., "Dipeptidylpeptidase IV (CD26) defines leukemic stem cells (LSC) in chronic myeloid leukemia," Blood First Edition paper, Apr. 28, 2014; DOI 10.1182/blood-2013-10-536078.

Yu Hong, et al., "Autoantibodies against tumor-associated antigens for detection of hepatocellular carcinoma," World J Hepatol Jun. 18, 2015; 7(11): 1581-1585.

Yi Huan, e al., "Establishment of a dipeptidyl peptidases (DPP) 8/9 expressing cell model for evaluating the selectivity of DPP4 inhibitors," Journal of Pharmacological and Toxicological Methods 71 (2015) 8-12.

Miyako Kishimoto, "Teneligliptin: a DPP-4 inhibitor for the treatment of type 2 diabetes," Diabetes, Metabolic Syndrome and Obesity: Targets and Therapy 2013:6 187-195.

Andre Kunert, "TCR-engineered T cells meet new challenges to treat solid tumors: choice of antigen, T cell fitness, and sensitization of tumor milieu," Frontiers in Immunology, Nov. 8, 2013 doi: 10.3389/fimmu.2013.00363.

Holly Meany, et al., "Pediatric Phase I Trial Design Using Maximum Target Inhibition as the Primary Endpoint," J Natl Cancer Inst 2010;102:909-912.

Kalyani Narra, Stefanie R. Mullins, Hyung-Ok Lee, Brenda Strzemkowski-Brun, Kimberly Magalong, Victoria J. Christiansen, Patrick A. McKee, Brian Egleston, Steven J. Cohen, Louis M. Weiner, Neal J. Meropol & Jonathan D. Cheng (2007) Phase II trial of single agent Val-boroPro (talabostat) inhibiting fibroblast activation protein in patients with metastatic colorectal cancer, Cancer Biology & Therapy, 6:11, 1691-1699, DOI: 10.4161/cbt.6.11.4874.

Saxagliptin, "FDA's Endocrinologic and Metabolic Drugs Advisory Committee Briefing Document for Apr. 2009 Meeting," By Bristol-Myers Squibb Company, dated Mar. 2, 2009.

Umadevi V. Wesley, et al., "Dipeptidyl Peptidase Inhibits Malignant Phenotype of Prostate Cancer Cells by Blocking Basic Fibroblast Growth Factor Signaling Pathway," Cancer Res 2005; 65(4): 1325-34.

Aiying Wang, et al., "Potency, selectivity and prolonged binding of saxagliptin to DPP4: maintenance of DPP4 inhibition by saxagliptin in vitro and ex vivo when compared to a rapidly-dissociating DPP4 inhibitor," BMC Pharmacology 2012, 12:2 http://www.biomedcentral.com/1471-2210/12/2.

Yi-Wen Zang, et al., Clinical application of adoptive T cell therapy in solid tumors, Med Sci Monit, 2014; 20: 953-959.

Paul. Fundamental Immunology, 3rd Edition, Raven Press, New York, Chapter 8, pp. 292-295, 1993 (Year: 1993).

Pech et al. Case Reports in Endocrinology, vol. 2015, Article ID 95019:1-4 (Year: 2015).

Vangoitsenhoven et al. Endocrine-Related Cancer (2012) 19 F77-F88 (Year: 2012).

Topalian et al. New England Journal of Medicine. 2012; 366(26): 2443-2454 (Year: 2012).

Ferrara et al. mABs, 2015; 7(1): 32-41 (Year: 2015).

Auerbach et al. Cancer and Metastasis Reviews, 200, 19: 167-172 (Year: 2000).

Gura T. Science, 1997, 278 (5340): 1041-1042 (Year: 1997).

Jain RK. Scientific American, Jul. 1994, 58-65 (Year: 1994).

Hait. Nature Reviews/Drug Discovery, 2010, 9, pp. 253-254 (Year: 2010).

Gravanis et al. Chin Clin Oncol, 2014, 3, pp. 1-5 (Year: 2014).

Bean. PNAS 2018; 115(50): 12539-12543 (Year: 2018).

\* cited by examiner

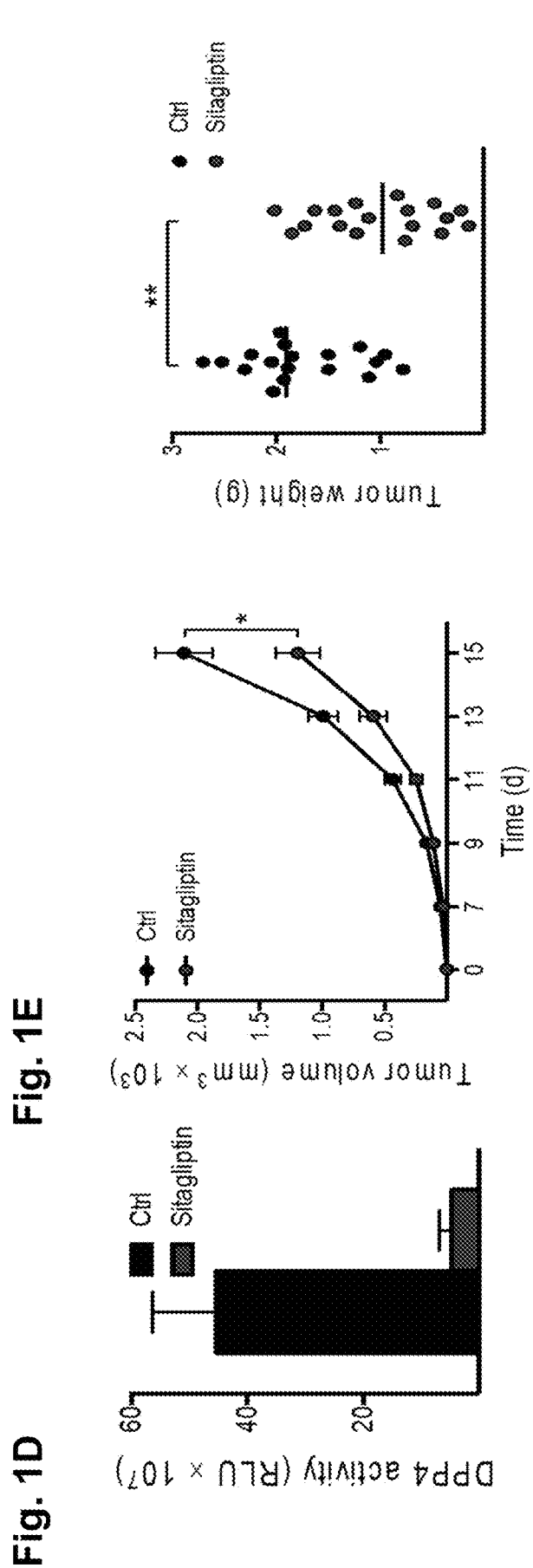

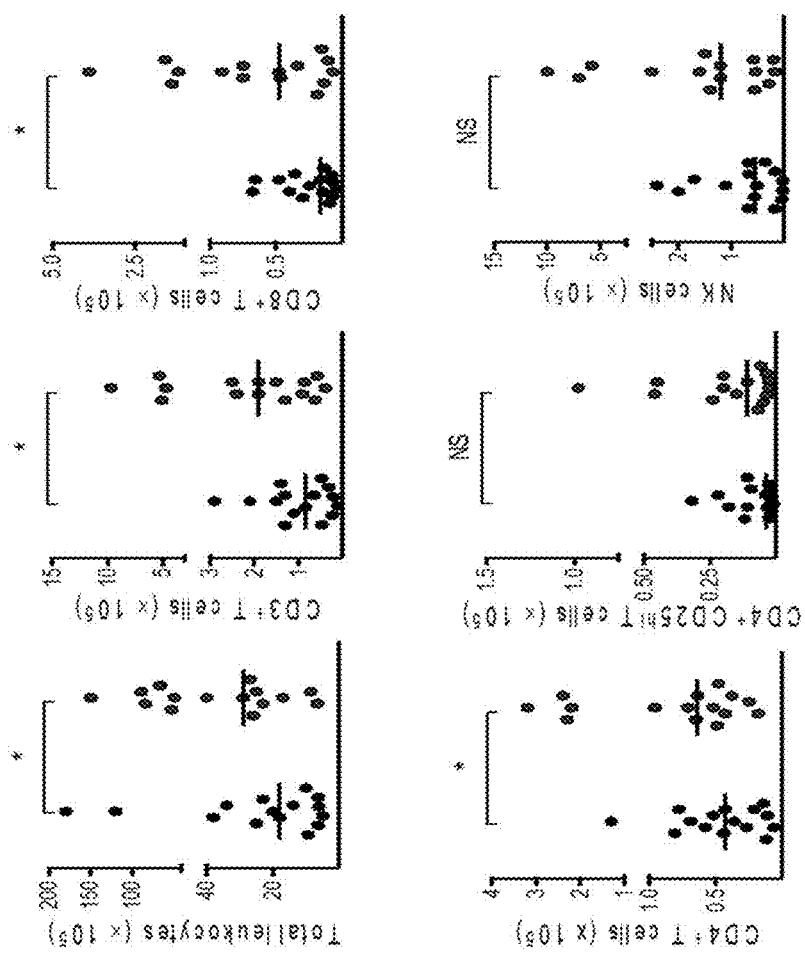

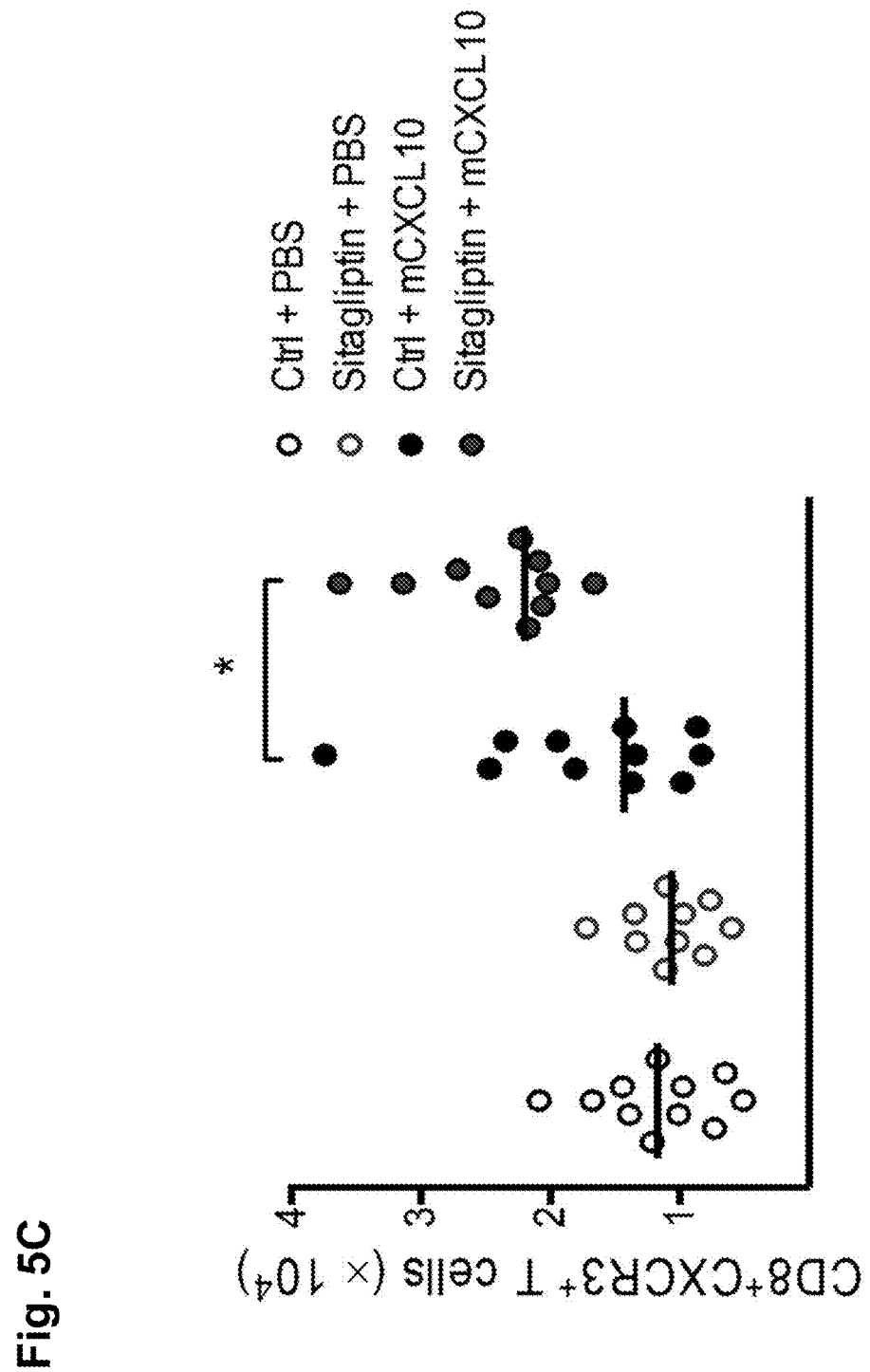

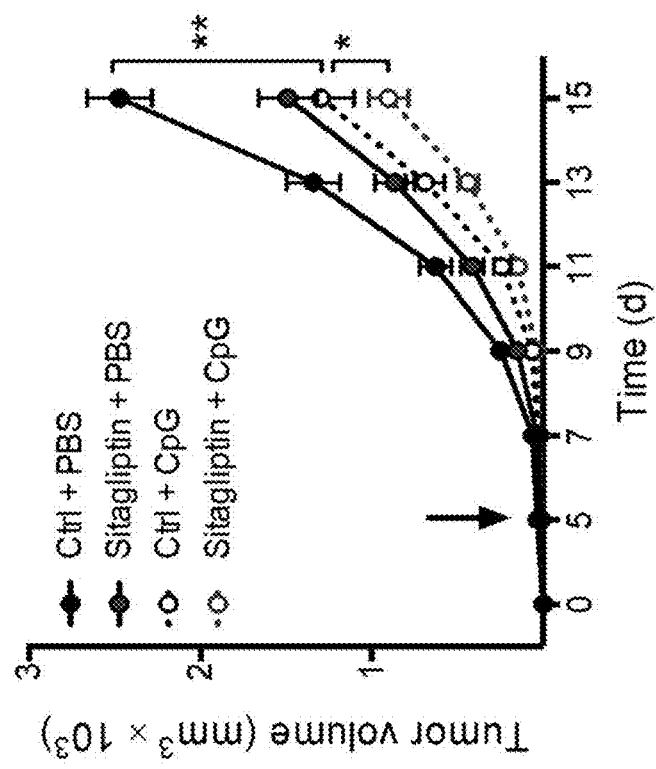
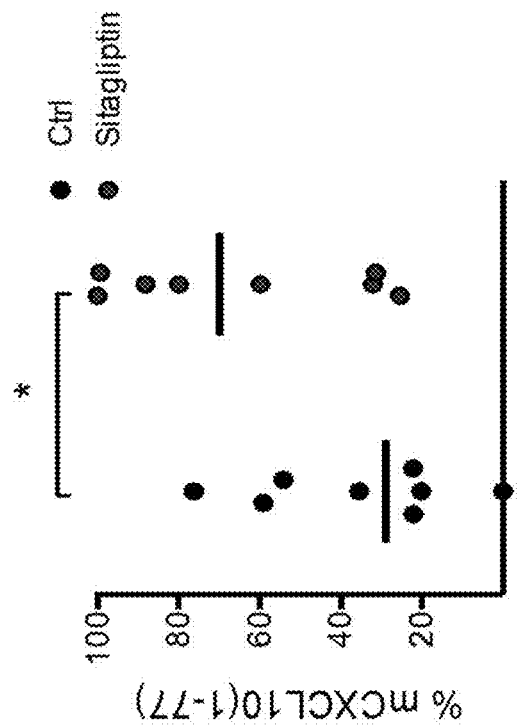
Fig. 6A
Fig. 6B

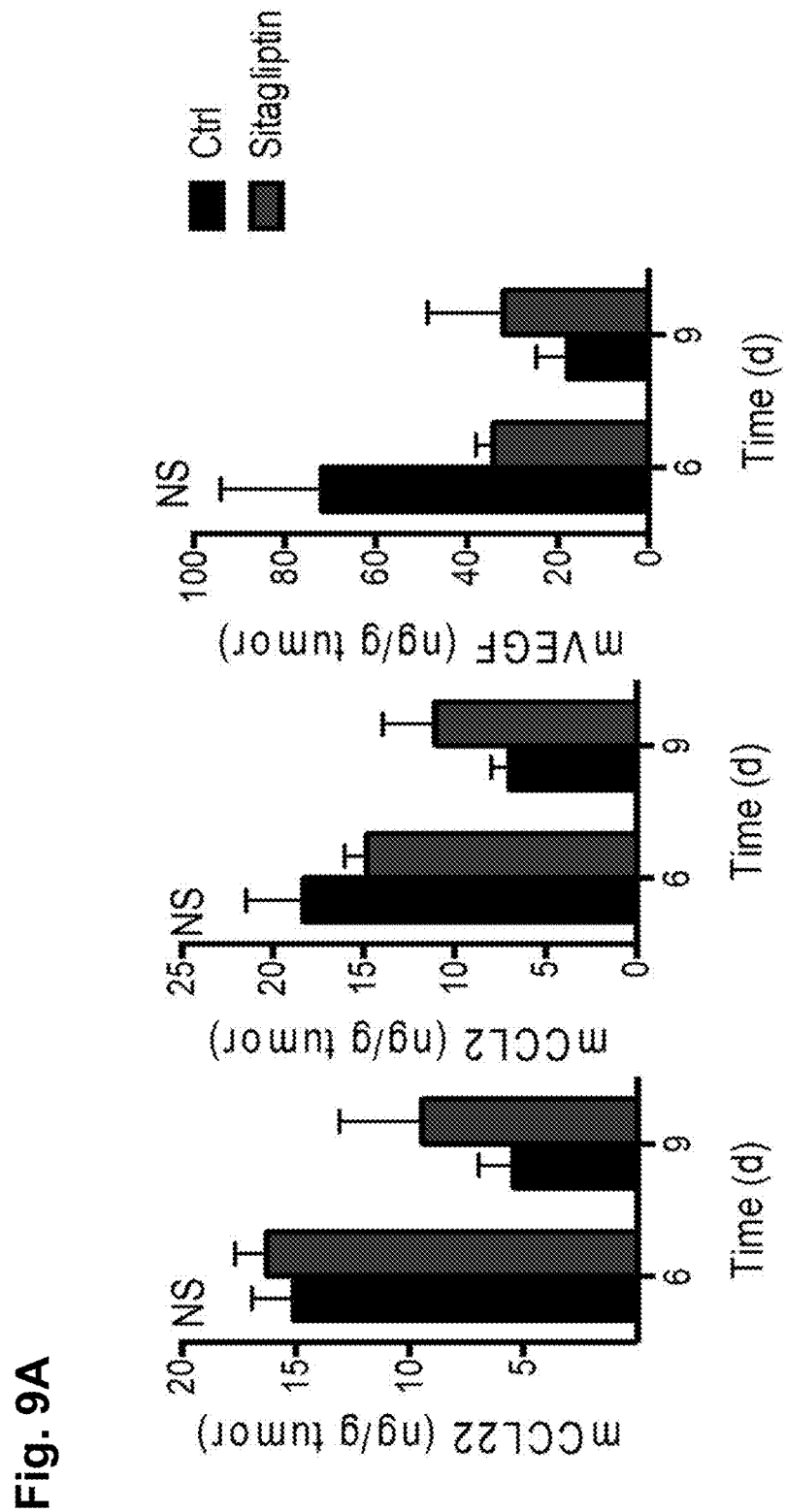

DIPEPTIDYLPEPTIDASE 4 INHIBITION ENHANCES LYMPHOCYTE TRAFFICKING, IMPROVING BOTH NATURALLY OCCURRING TUMOR IMMUNITY AND IMMUNOTHERAPY

CROSS REFERENCE TO RELATED APPLICATIONS

This application is a continuation of U.S. application Ser. No. 15/930,166, filed May 12, 2020, now U.S. Patent 11,229,645, which is a division of U.S. application Ser. No. 15/750,098, filed Feb. 2, 2018, now U.S. Pat. No. 11,000,521, which is the U.S. Natl. Stage of International Appln. PCT/EP2015/079663, filed Dec. 14, 2015, which claims the benefit of U.S. application 62/200,186 filed Aug. 3, 2015, all of which are herein incorporated by reference in their entirety.

TECHNICAL FIELD

The present invention is in the field of immunotherapy of cancer patients.

BACKGROUND

Chemokines regulate leukocyte trafficking in healthy tissues (homeostatic chemokines) and in response to stress, infection or tissue damage (inflammatory chemokines)[1]. Although the mechanisms supporting chemokine-induced leukocyte motility (chemokinesis) and directed migration (chemotaxis) have been described[2], less is known about how these mechanisms are regulated through naturally occurring post translational modifications. It is known that chemokine activity can be influenced by post-translational modifications[3,4], but the lack of direct in vivo evidence has limited the impact of these in vitro biochemical observations on both the field of chemotaxis and on the development of novel immunotherapies.

Dipeptidylpeptidase 4 (DPP4, also known as CD26) is an X-prolyl dipeptidylpeptidase capable of enzymatically removing the first two amino acids from proteins that possess a proline or alanine in the penultimate N-terminal position[5]. Under steady state conditions, DPP4 is enzymatically active both as a membrane-bound and soluble protein; and its expression extends to several tissues and biological fluids in the body[6]. DPP4 expression and/or activity can be modulated by inflammation and malignant transformation[7,8]. Although DPP4 has been documented as an important diagnostic or prognostic biomarker in several clinical settings, its role in regulating protein function in the context of disease pathogenesis is largely unknown. The one disease setting where DPP4 has been extensively studied is type II diabetes. N-terminal truncation of the incretin hormones glucose-dependent insulinotropic polypeptide (GIP) and glucagon-like peptide-1 (GLP-1) leads to the formation of antagonist forms, and constitutes a mechanism of insulin resistance in disease pathogenesis. Accordingly, DPP4 inhibitors have been developed and approved as treatment for type II diabetes patients[9].

In addition to the incretin hormones, other secreted molecules possess the N-terminal consensus motive for DPP4 recognition. Notably, several chemokines have been shown to be processed in vitro by DPP4[3,10]. Among these molecules, the pro-inflammatory chemokine CXCL10 was shown in vitro to be readily truncated. Importantly, this generated an antagonistic form that is capable of engaging its receptor, CXCR3, but does not induce chemotaxis4. Prior studies in chronic hepatitis C suggested that this phenomenon might have relevance in disease pathogenesis. Specifically, high concentrations of N-terminal truncated CXCL10 (referred to herein as CXCL10(3-77)) were correlated with treatment failure[11,12]. Moreover, treatment non-responders showed higher concentrations of soluble DPP4, as compared to those that achieved viral clearance[12,13]. Other chemokine substrates that have been characterized include CXCL12, whose truncation by DPP4 is believed to regulate G-CSF and GM-CSF mobilization of CXCR4-expressing hematopoietic stem cells[14]. CCL22 and CCL5 provide two additional examples that have been evaluated in vitro[10,15], however in vivo evidence of altered leukocyte trafficking is thus far lacking.

DPP4 has been described as having tumor suppressor function. Wesley et al., Cancer Res 2005; 65: (4), 2005. It has been shown to regulate the activities of mitogenic peptides implicated in cancer development. Id.

SUMMARY OF THE INVENTION

The invention encompasses a compositions or kits of parts for administration to a cancer patient. The invention further encompasses methods for enhancing anti-cancer immune responses in a patient.

In various embodiments, the composition or kit of parts comprises a Dipeptidylpeptidase 4 (DPP4) inhibitor and an anti-cancer immunotherapeutic.

In various embodiments, the method comprises administering to the patient a combination of a DPP4 inhibitor and an anti-cancer immunotherapeutic.

In various embodiments, the DPP4 inhibitor is selected from Sitagliptin, Vildagliptin, Saxagliptin, Linagliptin, Anagliptin, Teneligliptin, Alogliptin, Gemigliptin, Dutogliptin, Trelagliptin, Dutogliptin, Omarigliptin, Berberine, Carmegliptin, Denagliptin, ABT-279, ABT-341, and Lupeol.

In various embodiments, the anti-cancer immunotherapeutic is selected from a Tumor-Specific Antigen (TSA), a Tumor-Associated Antigen (TAA), an antibody, a modified immune cell, a cytokine, an immune checkpoint blockade molecule, and a virus or nucleic acid vector.

In various embodiments, the Tumor-Specific Antigen (TSA) or Tumor-Associated Antigen (TAA) is selected from MAG-Tn3, MAGE-A3, New York esophageal squamous cell carcinoma antigen (NY-ESO-1), HER-2/neu, p53, melanoma-associated antigen recognized by T cells 1 (MART-1), glycoprotein (gp) 100, Alphafetoprotein (AFP), EGFRvIII-specific 14-amino acid peptide, PEP-3 chemically conjugated to keyhole limpet hemocyanin (KLH), CA-125, MUC-1, carcinoembryonic antigen (CEA), Epithelial tumor antigen (ETA), Tyrosinase, prostatic acid phosphatase (PAP), prostate-specific antigen (PSA), Sialyl-Tn, prostate specific membrane antigen (PSMA), and non-catalytic hTERT.

In various embodiments, the antibody is a monoclonal antibody that targets CD52, EGFR, VEGF, HER-2, CD20, CD16, OX40, CD137, CD27, GITR, CD40, CD19, CD272, CD279, CD274, PAP, CD38, CD47, or GD2.

In various embodiments, the modified immune cell is a dendritic cell.

In various embodiments, the dendritic cell expresses a PAP antigen.

In various embodiments, the modified immune cell is a T cell.

In various embodiments, the modified immune cell expresses a chimeric antigen receptor (CAR). In various embodiments, the CAR is directed against CD19, melanoma-associated antigen recognized by T cells 1 (MART-1), glycoprotein (gp) 100, carcinoembryonic antigen (CEA), p53, MAGE-A3, or New York esophageal squamous cell carcinoma antigen (NY-ESO-1).

In various embodiments, the cytokine is an interferon or an interleukin.

In various embodiments, the immune checkpoint blockade molecule is a monoclonal antibody that targets CTLA-4, PD-L1 or PD-1.

In various embodiments, the virus expresses a 5T4 tumor-associated antigen.

In various embodiments, the or kit of parts of claim 1 or 2, further comprises an adjuvant or immune modulator selected from GM-CSF, KLH, liposomal AS15, BCG, freeze dried BCG, MONTANIDE, IL-2, and KLH.

In various embodiments, the method further comprises administering an adjuvant or immune modulator selected from GM-CSF, KLH, liposomal AS15, BCG, freeze dried BCG, MONTANIDE, IL-2, and KLH.

BRIEF DESCRIPTION OF THE DRAWINGS

FIG. 1a-g. Inhibition of DPP4 enhances naturally occurring anti-tumor responses to B16F10 melanoma. (a) C57BL/6 wild-type (WT) and Dpp4$^{-/-}$ mice were subcutaneously injected B16F10 cells. Eight days following injection tumor homogenates were prepared and DPP4 activity was determined (RLU—relative luminescence units; bars represent mean±±SEM n=3 (WT) and 4 (Dpp4$^{-/-}$) mice (b) Tumor cells were transferred into Dpp4$^{+/-}$ and Dpp4$^{-/-}$ mice as described in a. Tumor volumes are shown (mean±SEM, n=6 mice per group) * P<0.01. (c) WT mice were fed with chow containing 1.1% sitagliptin or control (Ctrl) chow. DPP4 activity was measured in plasma samples collected before and 24h after initiation of treatment (Tx). DPP4 plasma activity is shown for Dpp4$^{-/-}$ mice and used as a reference for absence of activity. Circles represent individual mice. (d, e) WT mice receiving control or sitagliptin diet were subcutaneously injected as described in a. DPP4 activity in tumor homogenates was performed (d, bars represent mean±SEM, n=4 mice per group). Tumor volumes and weights (measured on day 15) are shown (e, data represent mean±SEM, n=18 mice per group * P<0.01; ** P<0.005). (f) WT mice with growing B16F10 tumors were fed sitagliptin chow at day 3, 5 and 7 (downward arrows). Tumor volumes are shown (mean±SEM, n=12, 13 and 7 mice per group, from left to right * P<0.05, ** P<0.01). (g) Control and sitagliptin fed WT mice were intravenously injected with 2×10$^5$ B16F10 cells. 15 days after injection lungs were dissected and metastatic foci were imaged and counted. Representative images from 4 mice per group are shown, and all mice are plotted with circles indicating the number of metastases in a single mouse (n=9 mice per group, * P<0.05). Significance was determined using 2Way Anova (b, e-left panel and f) and Mann-Whitney (e-right panel and g). Data shown are representative of 2 (a, b and d); 8 (c), or pooled from 3 (e) or 2 (f, g) independent experiments. NS=not significant (P >0.05).

FIG. 2a-g. DPP4 diminishes CXCL10 expression and limits CXCR3-mediated anti-tumor immunity. (a). B16F10 tumors were extracted and homogenized at the indicated time point followed by CXCL10 quantification (mean±SEM, n=4 mice per group; * P<0.05). (b) Recombinant mouse (m)CXCL10 was incubated with (+) or without (−) recombinant DPP4 and analyzed by SELDI-TOF mass spectrometry. Numbers indicate the molecular weight (Daltons) of non-digested (top) and DPP4-digested products. Alignment of the first 12 N-terminal amino acids of mouse and human CXCL10 sequences indicate the presence of a proline (highlighted in red) in the second position of the N-terminus. (c) Number of tumor-infiltrating leukocyte populations analyzed 9 days after injection (Each circle represents 1 mouse, * P<0.05). (d-f) B16F10 tumor growth in Rag2$^{-/-}$, (d) Cxcr3$^{-/-}$ (e) or Cxcl10$^{-/-}$ (f) mice fed with control or sitagliptin chow (Mean±SEM, n=12 (d) 11 (e) and 16 (f) mice per group. (g) CD31 immunostaining was performed in fixed tumors slices. Scale bars indicate 250 μm. T—Tumor tissue; D—Dermis; E—Epidermis. CD31 positive blood vessel profiles were counted and measured as described in the Materials and Methods. Each circle represents a single mouse. Significance was determined using Mann-Whitney (a, c, d—right panel, and g) and 2Way Anova (d—left panel, e and f). Data are representative of 3 (b); 2 (a, g) or pooled from 3 (c, f) or 2 (d, e) independent experiments.

FIG. 5a-f. Inhibition of DPP4 enhances in vivo CXCL10-mediated lymphocyte trafficking. (a). Bioluminescence images of FVB CAG-Luciferase transgenic mice fed with ctrl or sitagliptin chow, acquired 5 min after intraperitoneal injection of Gly-Pro-aminoluciferin. (b) and DPP4 activity measured in the peritoneal lavage of WT mice were fed with ctrl or sitagliptin chow (* P<0.005). (c, d) WT mice fed with control or sitagliptin food were injected intraperitoneally with PBS or recombinant mCXCL10. The absolute number (c) and CXCR3 MFI (d) on CXCR3-expressing CD8$^+$ T cells were determined. Representative histograms are shown (* P<0.05 (c) * P<0.005 (d)). (e, f) WT mice fed with ctrl or sitagliptin food and growing B16F10 tumors were given an intra-tumoral injection of PBS or mCXCL10, 7 days after tumor-cell implant. The number of endogenous lymphocytes was determined (e) (* P<0.05,  P<0.01, * P<0.005. (f) 3 days after tumor cell implantation, mice received an adoptive transfer of Cxcr3$^{-/-}$ and Cxcr3$^{+/+}$ Pmel-1 CD8$^+$ T cells (1:1 mix, total of 1×10$^6$ cells). Tumors were dissected after mCXCL10 intratumoral injection, as described in (e). Representative dot plots are shown, indicating the strategy for discriminating transferred cells based on congenic markers: Cxcr3$^{-/-}$ (Thy-1.1$^+$Thy-1.2$^+$) and Cxcr3$^{+/+}$ (Thy-1.1$^+$ Thy-1.1$^+$) Pmel-1 infiltrates, among host CD8$^+$ T cells (Thy-1.2$^+$Thy-1.2$^+$). The number of infiltrating Pmel-1 cells was calculated (*P<0.05). Each circle represents a single mouse. Significance was determined using Mann-Whitney statistical tests. Data are from 1 experiment (a, b) or pooled from 3 (f) or 2 (c, d and e) independent experiments.

FIG. 6a-e. DPP4 inhibition protects adjuvant-induced CXCL10 and improves tumor immunity. WT (a, b, e), Ifnar1$^{-/-}$ (c) or Cxcr3$^{-/-}$ (d) mice fed with ctrl or sitagliptin chow were subcutaneously injected with B16F10 cells. Mice were given an intra-tumoral injection of 5 µg CpG-A or PBS (downwards arrows). (a) Six hours following CpG-A injection, tumors were dissected and mCXCL10 expression was determined in tumor homogenates. Graph represents percentage of mCXCL10(1-77) among total mCXCL10 (b-d) Tumor volumes are shown (data represents mean±SEM; n=11 (b) and 5 (c, d) mice, * P<0.01, ** P<0.0001). (e) 18 hours after intratumoral CpG injection, tumors were dissected and prepared for histological analysis: H&E—hematoxylin and eosin staining (upper images of low magnification and middle high-powered images); CD3 immunolabelling (lower panels). T—Tumor. Stars highlight areas of high inflammation. Red arrowheads indicate infiltrating CD3$^+$ cells. Images are representative of n=11 mice per group. Scale bars are 100 µm. Each circle represents a mouse (a). Significance was determined using Mann-Whitney (a) or 2Way Anova (b-d). Data are representative of 2 (c,-e) or pooled from 2 (a, b) independent experiments.

FIG. 9a-d. Susceptibility of mouse chemokines to DPP4-mediated processing. (a) WT mice fed with control (ctrl) or sitagliptin chow were subcutaneously injected with B16F10 cells. Tumors were dissected at the indicated time points after tumor cell injection, and mCCL22, mCCL2 and mVEGF expression in tumor homogenates was evaluated (data represent mean±s.e.m.; n=4 mice per group). (b,c) Recombinant mCXCL9 and mCXCL11 (b) and mCCL2, mCCL22, mCXCL12, mCCL3, mCCL4 and mCCL5 (c) were incubated in the absence (−) or presence (+) of recombinant DPP4 and analyzed by SELDI-TOF mass spectrometry. (d) WT mice were treated as described in a. Tumors were dissected at the indicated time points, and the number of infiltrating leukocytes was determined. Graphs represent fold change in tumor infiltrates upon sitagliptin treatment when compared with ctrl treatment (dashed line). Each circle represents a single mouse; *P<0.05. P values were generated via Mann-Whitney test. Data are representative of 2 independent experiments (a) or are pooled from 2-3 independent experiments (d).

WT mice fed with sitagliptin or ctrl chow were injected intraperitoneally with thioglycollate. Cellular contents in the peritoneal cavity were analyzed 24 h after injection. (a) The gating strategy used for the identification of neutrophils, eosinophils and monocytes among peritoneal leukocytes is shown. (b,c) The cell number of infiltrating myeloid (b) and lymphoid (c) populations is indicated. P values from Mann-Whitney test. Data are combined from 2 independent experiments.

Figure 16:
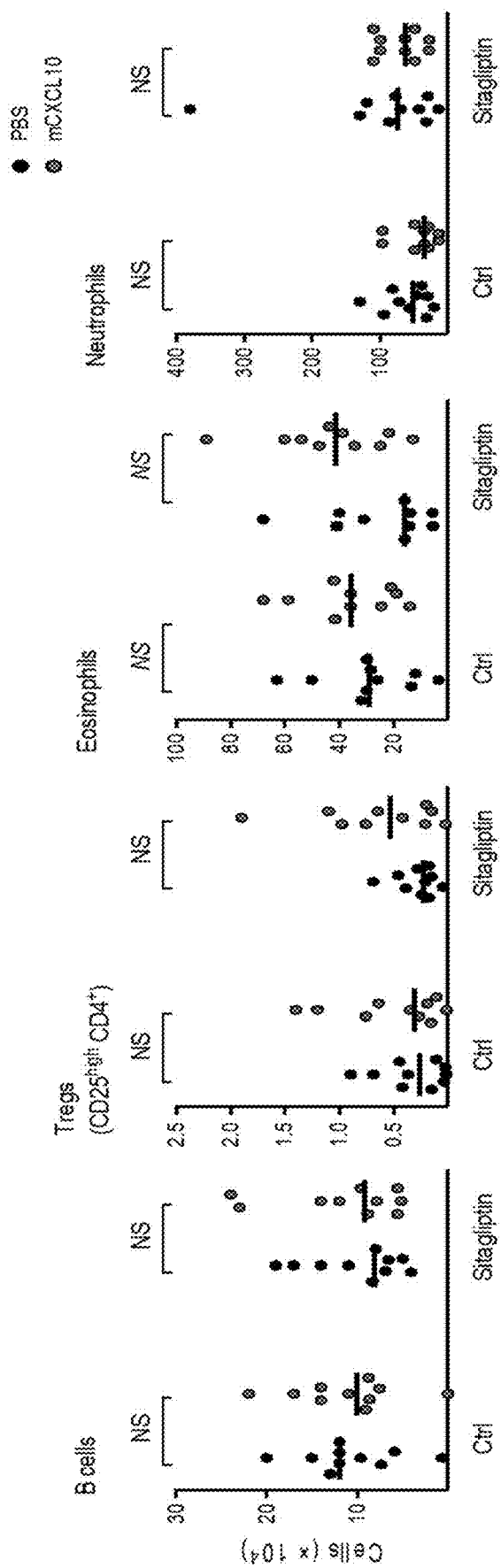

FIG. 16. DPP4 inhibition does not affect the recruitment of myeloid cells in B16F10 tumors. WT mice fed with ctrl or sitagliptin chow were subcutaneously injected with B16F10 tumor cells. Mice were given an intratumoral injection of PBS or mCXCL10 7 d after tumor-cell implant. The number of endogenous leukocytes was analyzed 12-14 h after intratumoral injection. Each circle represents a single mouse. P values from Mann-Whitney test. Data are combined from 2 independent experiments.

DETAILED DESCRIPTION OF THE INVENTION

The present inventors tested the hypothesis that DPP4 could be regulating chemokine-mediated lymphocyte trafficking into inflammatory sites, such as the tumor parenchyma. Their findings provide the first direct evidence for DPP4 inhibition as a mechanism for protecting the biologically active form of CXCL10, which in turn enhanced recruitment of lymphocytes into the tumor parenchyma. DPP4 inhibitors, including sitagliptin (currently approved for use in type II diabetes) also enhanced the effect of three distinct immunotherapy strategies. These results provide a functional role for DPP4-mediated post-translation modification of chemokines in the regulation of tumor immunity. Importantly, the inventors provide herein experimental support for the re-purposing of DPP4 inhibitors, which can be used to direct effector cell migration in the context of tumor immunotherapy.

This study provides the first direct demonstration for DPP4 as an in vivo regulator of CXCL10-mediated lymphocyte trafficking, with relevance for tumor immunity and immunotherapy. By treating mice with an orally active inhibitor of DPP4 enzymatic activity, the inventors demonstrated preservation of full length CXCL10 that resulted in an enhanced T cell migration to inflammatory sites. Remarkably, upon DPP4 inhibition, the efficacy of naturally occurring and immunotherapy-based tumor immunity was also augmented. This work places the upregulation and/or induction of DPP4 expression by some tumors in a new context; and establishes chemokine post-translational modification as a key immunomodulatory step that can be targeted therapeutically to enhance inflammation.

DPP4 belongs to a family of six pleotropic serine proteases that cleave the N-terminal two amino acids of proteins and peptides[5]. Their roles in regulating biological processes are dictated by their expression pattern and the targeted substrate. Fibroblast activation protein alpha (FAP, also known as Seprase) and DPP4 are the two cell surface expressed enzymes, having their catalytic domain facing the extracellular space[28]. In the case of DPP4, but not FAP, high levels of soluble protein (referred to as sDPP4) can be found in the plasma and urine of healthy individuals[6,29]. In addition to its well-studied regulation of the incretin hormones, in vitro biochemical studies have shown that DPP4 can cleave up to 36 chemokines and cytokines possessing a putative truncation site for DPP4 (i.e., presence of proline in the penultimate position of the N-terminus)[30], with stromal derived factor-1 (SDF-1 or CXCL12) being the most substantive in vivo example[20,31]. While suggesting a possible role of DPP4 in the regulation of immune cell migration, in vivo data has not been established; and the concept of post-translational modification as means of regulating leukocyte trafficking has been largely overlooked in the field, although few studies were able to identify truncated forms of chemokines in biological samples[31,32]. Indeed, to define DPP4 as an in vivo regulator of chemokine-mediated leukocyte trafficking it was essential to provide definitive evidence of $NH_2$-terminal truncation of in vivo substrates.

Several examples of upregulated or induced DPP4 expression in the context of malignant transformation have been described.[7,33] In some instances the tumor cell itself expressed DPP4; and in other examples the tumor cell does not express the enzyme, and instead induces its expression in the surrounding tumor stroma[34]. Prior experimental studies have evaluated dipeptidylpeptidases as a target for tumor therapy, however these reports have been limited due to their use of chemical inhibitors that block both DPP4 and FAP activity[35,36]. One notable exception is the work of Arwert and colleagues, who reported that DPP4 is upregulated in a model of MEK1 induced skin tumors, and that treatment with sitagliptin, the same DPP4 specific inhibitor used herein, delays malignant transformation[37]. While their study suggests that DPP4 inhibition may synergize with IL1RA therapy, they do not consider a role for regulation of lymphocyte trafficking. Instead, they hypothesize that blood glucose levels might alter tumor cell proliferation. However, the present inventors demonstrated that a role for immune-independent mechanisms cannot be ruled out as DPP4 inhibition in Rag2−/−, Cxcr3−/− and Cxcl10−/− animals failed to show a beneficial effect. As FAP has been reported to be an oncogene[36], and recent work suggests that FAP-expressing carcinoma-associated fibroblasts contribute to tumor growth[38] the present inventors were careful to exclude this as an alternative regulator of tumor immunity in their models.

Post-translational modification of intracellular proteins is fundamental for cellular biology processes such as signal transduction or chromatin organization; however the role of modifications of extracellular proteins in the extracellular space is poorly understood.

Regarding chemokines, several families of enzymes have been reported to modify their structure and/or function_. While DPP4-mediated truncation of several chemokines abrogated their chemoattractive functions[3,4], N-terminal truncation of CXCL5, as well as COOH-truncation of CXCL7 have been shown to enhance their in vitro chemoattractive potential[40,41]. Considering CXCL10 regulation, Van den Steen and colleagues have demonstrated C-terminal truncation by gelatinase B and neutrophil collagenase/MMP-8, do not impact in vitro chemotactic activity[42]. Moreover, peptidylarginine deaminases can citrullinate CXCL10, which modestly reduces migration of T cells, and may alter its interaction with heparin sulfate binding proteins[43]. Strikingly, our study of dipeptidylpeptidase N-terminal truncation provides the first experimental evidence for post-translational modification of CXCL10 having an in vivo biological significance.

The field of tumor immunotherapy has witnessed a rebirth in the last few years, with recent approval of CTLA-4 and PD-1 inhibitors for the treatment of melanoma; as well as several successful high-profile clinical trials[44]. Moreover, immune adjuvants (e.g., CpG) which have been directly injected into tumors as a means to enhance the function of antigen presenting cells (APCs) and support T cell priming[25]. Limiting the efficacy of these strategies, tumors have evolved mechanisms to resist the action of incoming lymphocytes and promote immunosuppression[45]. This study shows that DPP4 participates in restricting lymphocyte access to the tumor parenchyma, by modifying the pro-inflammatory chemokine CXCL10. The present results offer considerable opportunities for combination therapy, adding DPP4 inhibitors to existing tumor immunotherapy protocols. This innovative approach to enhance lymphocyte trafficking into tumors may be readily combined with current practices, including T cell adoptive therapy (in instances where the transferred T cells mediate killing)[46-48], intra-tumoral injection of TLR ligands[24,25] or checkpoint blockade[49,50]. In fact, there is a remarkable opportunity for application of this approach, as DPP4 inhibitors are widely used in the clinic. Over 30 million people are currently taking DPP4 inhibitors as a strategy of protecting the agonist form of the incretin hormones, highlighting their safety profile and the potential for rapid translation to other therapeutic purposes[9]. In sum, post-translational modification of chemokines is a general mechanism of immune regulation, and therapeutic control of these processes may provide robust strategies to enhance or inhibit immune responses.

Compositions and Kits of Parts

The invention encompasses a composition or kit of parts for administration to a cancer patient comprising a Dipeptidylpeptidase 4 (DPP4) inhibitor and an anti-cancer immunotherapeutic.

An "immunotherapeutic" as used herein refers to any type of compound which can be used in immunotherapy. Immunotherapy as used herein is the treatment of disease by inducing, enhancing, or suppressing an immune response. An "anti-cancer immunotherapy", as used herein, stimulates the immune system to reject and destroy tumors. An "anti-cancer immunotherapeutic" as used herein thus includes such compounds as e.g. Tumor-Specific Antigens (TSA), Tumor-Associated Antigens (TAA), immune adjuvants, immune modulators, antibodies, modified immune cells, cytokines, immune checkpoint blockade molecules, viruses. These compounds are further described here below.

Said DPP4 inhibitor and anti-cancer immunotherapeutic may be present in the same composition being administered or may be administered separately. In one aspect of the invention, the administration of the DPP4 inhibitor is performed with the anti-cancer immunotherapeutic, either simultaneously, separately or sequentially over time.

The composition or kit of parts is for simultaneous, separated or sequential administration to the patient. When the administration is performed simultaneously, the two active principles may be combined in a single pharmaceutical composition, comprising the two compositions, such as a tablet or a gel capsule. On the other hand, the two active principles may, whether or not they are administered simultaneously, be present in separate pharmaceutical compositions. To this end, the combination may be in the form of a kit comprising, on the one hand, the DPP4 inhibitor and, on the other hand, the anti-cancer immunotherapeutic, the DPP4 inhibitor and the anti-cancer immunotherapeutic being in separate compartments and being intended to be administered simultaneously, separately, or sequentially over time. The composition or kit of parts may thus be in a single vial or container or may be in multiple vials or containers.

The administration can be by conventional means including intravenous, oral, intramuscular, intratumoral, subcutaneous, and intranasal administration. A different form of administration may be used for the Dipeptidylpeptidase 4 (DPP4) inhibitor and the anti-cancer immunotherapeutic.

Simultaneous administration of the Dipeptidylpeptidase 4 (DPP4) inhibitor and the anti-cancer immunotherapeutic can be at the same time or within 1, 2, 3, or 4 hours of each other.

Sequential administration of the Dipeptidylpeptidase 4 (DPP4) inhibitor and the anti-cancer immunotherapeutic can be in either order and after 4 hr, 8 hr, 12 hr, 24 hr, 2 days, 3 days, 4 days, 1 week, 2 weeks, etc., of each other.

DPP4 Inhibitors

Within the context of this invention, a "Dipeptidylpeptidase 4 (DPP4) inhibitor" is a highly-selective inhibitor of DPP4 that shows no or only mild inhibition of Dipeptidylpeptidase 8 and 9, for example, when tested in a system of extracellular incubation with DPP8/9 over-expressing cells. See, Huan et al., J Pharmacol Toxicol Methods, 71:8-12 (2015), which is hereby incorporated by reference. Using this system, compounds such as e.g. sitagliptin, vildagliptin, saxagliptin, alogliptin, carmegliptin, denagliptin, ABT-279, ABT-341, and linagliptin have been shown to be highly-selective inhibitors of DPP4.

Thus, compounds inhibiting a multitude of DASH proteases (e.g. Val-boroPro and ARI-4175, and PT-100), as exemplified in WO2013/078059 and Narra et al., Cancer Biology & Therapy, 6:11, 1691-1699 (2007), which are hereby incorporated by reference, are specifically excluded from the meaning of "Dipeptidylpeptidase 4 (DPP4) inhibitor" as used herein. Preferably, the DPP4 inhibitor has an IC50 value that is at least 10-fold, 25-fold, 100-fold, 250-fold, 1,000-fold, 2,500-fold, or 10,000-fold greater for DPP8 and/or DPP9 than for DPP4 using the assays set forth in Huan et al. (2015), Table 1. In this assay, 0.01 μg of purified recombinant DDP4 or 100 μg of protein lysates of DPP8/9 over-expressing cells are used in an enzymatic assay. DPP4 enzymatic assays are well-known in the art; some are described hereafter in the experimental examples. Methods for measuring DPP8 and/or DPP9 activity are also well known in the art (see e.g., Hu et al., *Biotech Let,* 31: 979-984, 2009; Liu et al., *Acta Pharm Sin B,* 4(2):135-140, 2014).

Particularly preferred DPP4 inhibitors are those that show no effect on DPP8 or DPP9 activity in an in vitro enzymatic assay, such as sitagliptin, linagliptin, and alogliptin (Verspohl, Pharmacol Rev., 64(2): 188-237, 2012; Huan et al., J Pharmacol Toxicol Methods, 71:8-12, 2015) which is hereby incorporated by reference. Likewise, carmegliptin, denagliptin, ABT-279, and ABT-341 are highly selective towards DPP4 (Madar et al., *J Med Chem*, 49(21): 6416-6420, 2006; Gilibili et al., *J Pharm Pharm Sci.*, 18(3): 434-447, 2015).

Preferably, the DPP4 inhibitor causes less than a 10%, 20%, 30%, 40%, or 50% reduction in DPP8 and/or DPP9 activity using the cell-based assays set forth in Huan et al. (2015), FIG. 4. In this assay, the DPP4 inhibitor is incubated with cells over-expressing DPP8 and/or DPP9 for a specified time, after which the DPP8 and/or DPP9 activity is assayed (see e.g., Hu et al., *Biotech Let*, 31: 979-984, 2009; Liu et al., *Acta Pharm Sin B*, 4(2):135-140, 2014). Preferably, the inhibitor is incubated at least 1 hour, preferably 2 hours, preferably 3 hours, preferably 4 hours, preferably 5 hours, preferably 6 hours.

Preferably, the Dipeptidylpeptidase 4 (DPP4) inhibitor is selected from trelagliptin, sitagliptin, vildagliptin, saxagliptin, linagliptin, anagliptin, teneligliptin, alogliptin, gemigliptin, dutogliptin, berberine, onglyza, trajenta, combiglyze, janumet, jentadueto, ofsitagliptin, carmegliptin, denagliptin, ABT-279, ABT-341, ALS2-0426/AMG 222, NVP-DPP728, P32/98, Gosogliptin, SK-0405, SDZ 029-576, and lupeol. More preferably, the Dipeptidylpeptidase 4 (DPP4) inhibitor is selected from trelagliptin sitagliptin, vildagliptin, saxagliptin, alogliptin, carmegliptin, denagliptin, ABT-279, ABT-341, and linagliptin, most preferably selected from sitagliptin, linagliptin, carmegliptin, denagliptin, ABT-279, ABT-341, and alogliptin.

Screening Methods for DPP4 Inhibitors

The invention encompasses screening methods for DPP4 inhibitors in a mouse. In one embodiment, the method comprises administering tumor cells to a mouse, administering a DPP4 inhibitor(s) to the mouse, administering an anti-cancer immunotherapeutic(s) to the mouse, and measuring the growth of the tumor cells or metastases.

The invention further encompasses a system for determining the effect of a DPP4 inhibitor on tumor cells comprising a mouse that is administered: exogenous tumor cells, a DPP4 inhibitor, and an anti-cancer immunotherapeutic(s).

The administration of the exogenous tumor cells, a DPP4 inhibitor, and an anti-cancer immunotherapeutic(s) can be in any order and all orders are contemplated. In other words, any one of the tumor cells, DPP4 inhibitor, and anti-cancer immunotherapeutic(s) may be administered before or after the other two. For example, the tumor cells may be administered before or after the DPP4 inhibitor and/or the anti-cancer immunotherapeutic(s). Likewise, the DPP4 inhibitor may be administered before or after the anti-cancer immunotherapeutic(s). The invention also contemplates the simultaneous administration of at least two of the tumor cells, DPP4 inhibitor, and anti-cancer immunotherapeutic(s). In that case, the third element is administered before, after or at the same time as the other two. For example, the DPP4 inhibitor may be administered simultaneously with the anti-cancer immunotherapeutic(s), with the administration of the tumor cells taking place before, after or at the same time.

The effect of the DPP4 inhibitor can be determined by the measuring the growth of the tumor cells or metastases in the presence of the anti-cancer immunotherapeutic(s) and in the presence and absence of the DPP4 inhibitor. Preferably, the presence of the DPP4 inhibitor decreases the growth or metastases of the tumor cells compared to the absence of the DPP4 inhibitor.

Preferably, the mouse is one of the mouse models in the Examples of the application.

Preferably, the mouse is selected from WT C57BL/6 CD45.1, Rag2$^{-/-}$, Cxcr3$^{-/-}$, Ifnar1$^{-/-}$ Dpp4$^{+/-}$, Dpp4$^{-/-}$, Cxcl10$^{-/-}$, Ccr5$^{-/-}$, Pmel-1 Thy-1.1$^+$Thy-1.1$^+$, OT1 and FVB-Tg(CAG-luc), Pmel-1 Thy-1.1$^+$Thy-1.1$^+$, Cxcr3$^{-/-}$ Thy-1.2$^+$Thy-1.2$^+$, and Pmel-1 Cxcr3$^{-/-}$ Thy-1.1$^+$Thy-1.2$^+$ mice.

Preferably, the tumor cells are a melanoma or colon carcinoma cell line, most preferably B16F10 melanoma cells or CT26 colon carcinoma cells.

Preferably, the Dipeptidylpeptidase 4 (DPP4) inhibitor is selected from trelagliptin, sitagliptin, vildagliptin, saxagliptin, linagliptin, anagliptin, teneligliptin, alogliptin, gemigliptin, dutogliptin, carmegliptin, denagliptin, ABT-279, ABT-341, berberine, and lupeol. More preferably, the Dipeptidylpeptidase 4 (DPP4) inhibitor is selected from trelagliptin, sitagliptin, vildagliptin, saxagliptin, alogliptin, carmegliptin, denagliptin, ABT-279, ABT-341, and linagliptin, most preferably selected from sitagliptin, linagliptin, carmegliptin, denagliptin, ABT-279, ABT-341, and alogliptin.

The anti-cancer immunotherapeutic can be selected from a Tumor-Specific Antigen (TSA), a Tumor-Associated Antigen (TAA), an immune adjuvant or an immune modulator, an antibody, a modified immune cell, a cytokine, an immune checkpoint blockade molecule, and a virus.

Most preferably, the anti-cancer immunotherapeutic is selected from CpG, adoptive T cell therapy, and anti-PD1 and/or anti-CTLA-4 antibodies.

Anti-Cancer Immunotherapeutics

The invention encompasses methods, compositions and kits of parts—comprising a (DPP4) inhibitor and an anti-cancer immunotherapeutic.

The anti-cancer immunotherapeutic can be selected from a Tumor-Specific Antigen (TSA), a Tumor-Associated Antigen (TAA), an immune adjuvant or an immune modulator, an antibody, a modified immune cell, a cytokine, an immune checkpoint blockade molecule, and a virus.

Tumor-Specific Antigens (TSA) and Tumor-Associated Antigens (TAA)

As used herein, the term "antigen" is any structural substance that serves as a target for the receptors of an adaptive immune response. A "Tumor-Specific Antigen" (TSA) as used herein refers to an antigen which is only present on tumor cells, but not on normal cells. By contrast, a "Tumor-Associated Antigen" (TAA), as used herein, is an antigen which is present not only on tumor cells but also on some normal cells.

Preferred Tumor-Specific Antigen (TSA) and Tumor-Associated Antigen (TAA) include MAG-Tn3 (See US 20140171618, incorporated herein by reference), Melanoma Associated Antigen-A3 (MAGE-A3) as described in Gaugler et al, J. Exp. Med. 179:921-930(1994) incorporated herein by reference, New York esophageal squamous cell carcinoma antigen (NY-ESO-1), HER-2/neu, p53, melanoma-associated antigen recognized by T cells 1 (MART-1), glycoprotein (gp) 100, Alphafetoprotein (AFP), EGFRvIII-specific 14-amino acid peptide PEP-3 chemically conjugated to keyhole limpet hemocyanin (KLH), CA-125, MUC-1, carcinoembryonic antigen (CEA), Epithelial tumor antigen (ETA), Tyrosinase, prostatic acid phosphatase (PAP), prostate-specific antigen (PSA), Sialyl-Tn, prostate specific membrane antigen (PSMA), and non-catalytic hTERT.

Other preferred TSA and TAA include epidermal growth factor receptor, survivin, ras, LAGE-1, MAGE-A4, SSX-2, RCAS1, and WT1. Other TSA and TAA are described in Melero, I. et al. (2014), Therapeutic vaccines for cancer: an overview of clinical trials Nat Rev Clin Oncol. 2014 September; 11(9):509-24, and Hong et al., World J Hepatol. 2015 Jun. 18; 7(11): 1581-1585, which are hereby incorporated herein by reference.

The TSAs and TAAs can be delivered as proteins/peptides, nucleic acids encoding these antigens, or using viral vectors.

Many tumors express mutations. These mutations potentially create new targetable antigens (neoantigens) for use in immunotherapy. A "neoantigen", as used herein, is a newly formed antigen that has not been previously recognized by the immune system.

Immune Adjuvants and Immune Modulators

As used herein, an "immune adjuvant" is a component that potentiates the immune responses to an antigen towards the desired immune responses. An "immune modulator", as used herein, is a component that modulates the immune responses to an antigen towards the desired immune responses.

Preferred immune adjuvants/immune modulators include TLR agonists, preferably TLR9 agonists, for example CpG and PF-3512676. See, e.g., Pashenkov, M., et al., *J Clin Oncol* 24, 5716-5724 (2006); Krieg, A. M., *Nucleic Acid Ther* 22, 77-89 (2012), which are hereby incorporated by reference.

The invention further contemplates a composition or kit of parts for immunotherapy comprising a DDP4i, a Tumor-Specific Antigen (TSA) or a Tumor-Associated Antigen (TAA), and an adjuvant or immune modulator such as GM-CSF, KLH, liposomal AS15, BCG, freeze dried BCG, MONTANIDE, IL2, KLH.

Antibodies

The invention comprises isolated antibodies that bind specifically to TAAs, TSAs, and immune checkpoint proteins, and peptides derived therefrom. In some embodiments, purified proteins are used to produce antibodies by conventional techniques. In some embodiments, recombinant or synthetic proteins or peptides are used to produce antibodies by conventional techniques.

Antibodies can be synthetic, monoclonal, or polyclonal and can be made by techniques well known in the art. A typical antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. Such antibodies specifically bind to proteins and polypeptides via the CDRs, i.e. the antigen-binding sites of the antibody (as opposed to non-specific binding). Purified or synthetic proteins and peptides can be employed as immunogens in producing antibodies immunoreactive therewith. The proteins and peptides contain antigenic determinants or epitopes that elicit the formation of antibodies.

These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon protein folding (C. A. Janeway, Jr. and P. Travers, Immuno Biology 3:9 (Garland Publishing Inc., 2nd ed. 1996)). Because folded proteins have complex surfaces, the number of epitopes available is quite numerous; however, due to the conformation of the protein and steric hindrances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Such epitopes or variants thereof can be produced using techniques well known in the art such as solid-phase synthesis, chemical or enzymatic cleavage of a polypeptide, or using recombinant DNA technology.

Antibodies are defined to be specifically binding if they bind proteins or polypeptides with a Ka of greater than or equal to about $10^7$ $M^{-1}$. Affinities of binding partners or antibodies can be readily determined using conventional techniques, for example those described by Scatchard et al., Ann. N.Y. Acad. Sci., 51:660 (1949).

Polyclonal antibodies can be readily generated from a variety of sources, for example, horses, cows, goats, sheep, dogs, chickens, rabbits, mice, or rats, using procedures that are well known in the art. In general, a purified protein or polypeptide that is appropriately conjugated is administered to the host animal typically through parenteral injection. The immunogenicity can be enhanced through the use of an adjuvant, for example, Freund's complete or incomplete adjuvant. Following booster immunizations, small samples of serum are collected and tested for reactivity to proteins or polypeptides. Examples of various assays useful for such determination include those described in Antibodies: A Laboratory Manual, Harlow and Lane (eds.), Cold Spring Harbor Laboratory Press, 1988; as well as procedures, such as countercurrent immuno-electrophoresis (CIEP), radioimmunoassay, radio-immunoprecipitation, enzyme-linked immunosorbent assays (ELISA), dot blot assays, and sandwich assays. See U.S. Pat. Nos. 4,376,110 and 4,486,530.

Monoclonal antibodies can be readily prepared using well known procedures. An antibody reactive with a specific antigen can be generated by recombinant methods such as selection of libraries of recombinant antibodies in phage or similar vectors, or by immunizing an animal with the antigen or an antigen-encoding nucleic acid. See, for example, the procedures described in U.S. Pat. Nos. RE 32,011, 4,902,614, 4,543,439, and 4,411,993; Monoclonal Antibodies, Hybridomas: A New Dimension in Biological Analyses, Plenum Press, Kennett, McKeam, and Bechtol (eds.), 1980.

For example, the host animals, such as mice, can be injected intraperitoneally at least once and preferably at least twice at about 3 week intervals with isolated and purified proteins or conjugated polypeptides, for example a peptide comprising or consisting of the specific amino acids set forth above. Mouse sera are then assayed by conventional dot blot technique or antibody capture (ABC) to determine which animal is best to fuse. Approximately two to three weeks later, the mice are given an intravenous boost of the protein or polypeptide. Mice are later sacrificed and spleen cells fused with commercially available myeloma cells, such as Ag8.653 (ATCC), following established protocols. Briefly, the myeloma cells are washed several times in media and fused to mouse spleen cells at a ratio of about three spleen cells to one myeloma cell. The fusing agent can be any suitable agent used in the art, for example, polyethylene glycol (PEG). Fusion is plated out into plates containing media that allows for the selective growth of the fused cells. The fused cells can then be allowed to grow for approximately eight days. Supernatants from resultant hybridomas are collected and added to a plate that is first coated with goat anti-mouse Ig. Following washes, a label, such as a labeled protein or polypeptide, is added to each well followed by incubation. Positive wells can be subsequently detected. Positive clones can be grown in bulk culture and supernatants are subsequently purified over a Protein A column (Pharmacia).

The monoclonal antibodies of the invention can be produced using alternative techniques, such as those described by Alting-Mees et al., "Monoclonal Antibody Expression Libraries: A Rapid Alternative to Hybridomas", Strategies in Molecular Biology 3:1-9 (1990), which is incorporated herein by reference. Similarly, binding partners can be constructed using recombinant DNA techniques to incorporate the variable regions of a gene that encodes a specific binding antibody. Such a technique is described in Larrick et al., Biotechnology, 7:394 (1989).

Antigen-binding fragments of such antibodies, which can be produced by conventional techniques, are also encompassed by the present invention. Examples of such fragments include, but are not limited to, Fab and F(ab')2 fragments. Antibody fragments and derivatives produced by genetic engineering techniques are also provided.

The monoclonal antibodies of the present invention include in particular chimeric antibodies and humanized antibodies, i.e. versions of murine monoclonal antibodies with reduced immunogenicity.

Such chimeric and humanized antibodies can be prepared by known techniques, and offer the advantage of reduced immunogenicity when the antibodies are administered to humans. A "chimeric antibody", as used herein, is an antibody in which the constant region, or a portion thereof, is altered, replaced, or exchanged, so that the variable region is linked to a constant region of a different species, or belonging to another antibody class or subclass. "Chimeric antibody" also refers to an antibody in which the variable region, or a portion thereof, is altered, replaced, or exchanged, so that the constant region is linked to a variable region of a different species, or belonging to another antibody class or subclass. In one embodiment, a chimeric monoclonal antibody comprises the variable region of a murine antibody (or just the antigen binding site thereof) and a constant region derived from a human antibody. Alternatively, a chimeric antibody fragment can comprise the antigen binding site of a murine monoclonal antibody and a variable region fragment (lacking the antigen-binding site) derived from a human antibody.

Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, May, 1993).

A "humanized antibody" as used herein refers to an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988).

The goal of humanization is a reduction in the immunogenicity of a xenogenic antibody, such as a murine antibody, for introduction into a human, while maintaining the full antigen binding affinity and specificity of the antibody. The humanized antibodies of the invention or fragments of same can be prepared by techniques known to a person skilled in the art (such as, for example, those described in Singer et al., J. Immun., 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for their use in methods involving in vitro diagnoses or preventive and/or therapeutic treatment in vivo. Antibodies can be humanized using a variety of other techniques including CDR-grafting (EP 0 451 261, EP 0 682 040, EP 0 939 127, EP 0 566 647 or U.S. Pat. Nos. 5,530,101, 6,180,370, 5,585,089 and 5,693,761), veneering or resurfacing (EP 0 592 106; EP 0 519 596; Padlan E. A., 1991, Mol Immunol, 28(4/5): 489-498; Studnicka G. M. et al., 1994, Protein Engineering 7(6): 805-814; Roguska M. A. et al., 1994, Proc. Natl. Acad. Sci. U.S.A., 91: 969-973), and chain shuffling (U.S. Pat. No. 5,565,332). Another preferred method of humanization of antibodies, based on the identification of flexible residues, has been described in PCT application WO 2009/032661.

In certain embodiments both the variable and constant regions of the antibodies, or antigen-binding fragments, variants, or derivatives thereof are fully human. Fully human antibodies can be made using techniques that are known in the art. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140. Other techniques are known in the art. Fully human antibodies can likewise be produced by various display technologies, e.g., phage display or other viral display systems. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741 (said references incorporated by reference in their entireties). Procedures to generate antibodies transgenically can be found in GB 2,272,440, U.S. Pat. Nos. 5,569,825 and 5,545,806.

Antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in Robinson et al.

International Publication No. WO 87/02671; Akira, et al. European Patent Application 0184187; Taniguchi, M., European Patent Application 0171496; Morrison et al. European Patent Application 0173494; Neuberger et al. PCT International Publication No. WO 86/01533; Cabilly et al. U.S. Pat. No. 4,816,567; Cabilly et al. European Patent Application 0125023; Better et al., Science 240:1041 1043, 1988; Liu et al., PNAS 84:3439 3443, 1987; Liu et al., J. Immunol. 139:3521 3526, 1987; Sun et al. PNAS 84:214 218, 1987; Nishimura et al., Canc. Res. 47:999 1005, 1987; Wood et al., Nature 314:446 449, 1985; and Shaw et al., J. Natl. Cancer Inst. 80:1553 1559, 1988); Morrison, S. L., Science 229: 1202 1207, 1985; Oi et al., BioTechniques 4:214, 1986; Winter U.S. Pat. No. 5,225,539; Jones et al., Nature 321:552 525, 1986; Verhoeyan et al., Science 239:1534, 1988; and Beidler et al., J. Immunol. 141:4053 4060, 1988.

In connection with synthetic and semi-synthetic antibodies, such terms are intended to cover but are not limited to antibody fragments, isotype switched antibodies, humanized antibodies (e.g., mouse-human, human-mouse), hybrids, antibodies having plural specificities, and fully synthetic antibody-like molecules.

In one embodiment, the anti-cancer immunotherapeutic comprises a monoclonal antibody that targets CD28, CD52, EGFR, VEGF, HER-2, CD20, CD16, OX40, CD137, CD27, GITR, CD40, CD19, CD272, CD279, CD274, PAP, CD38, CD47, or GD2.

In one embodiment, the anti-cancer immunotherapeutic comprises a monoclonal antibody that targets a transmembrane programmed cell death 1 protein (PDCD1, PD-1; also known as CD279) or its ligand, PD-1 ligand 1 (PD-L1, CD274), such as for example Nivolumab described in Pardoll, DM Nature reviews of Mar. 22, 2012, incorporated herein by reference. In one embodiment, the anti-cancer immunotherapeutic comprises a monoclonal antibody that targets B7-H3, CTLA-4 (e.g., Ipilimumab), GITR, OX40, LAG-3, CTLA-4 (CD152, or TIM-3/Tim-3L.

In one embodiment, the anti-cancer immunotherapeutic comprises multiple antibodies, including combinations of 2 or 3 of any of the antibodies detailed herein. In a preferred embodiment, the anti-cancer immunotherapeutic comprises antibodies targeting PD-1 and LAG-3.

In still another embodiment, the anti-cancer immunotherapeutic comprises an anti-CD47 antibody, for example as described in Keith Syson Chan et al, Proc Natl Acad Sci USA. 2009 Aug. 18; 106(33): 14016-14021, incorporated herein by reference.

In still another embodiment, the anti-cancer immunotherapeutic comprises an anti-GD3 or anti-GD2 antibody, for example as described in Ahmed, M; Cheung, N K (Jan. 21, 2014). "Engineering anti-GD2 monoclonal antibodies for cancer immunotherapy.". FEBS Letters 588 (2): 288-97, incorporated herein by reference. In another embodiment, the anti-cancer immunotherapeutic comprises Bec2, an anti-idiotypic antibody that mimics GD3, a ganglioside antigen, preferably with *Bacillus* Calmette-Guerin (BCG), as described in Giaccone et al., J Clin Oncol. 2005 Oct. 1; 23(28):6854-64, incorporated herein by reference.

Modified Immune Cells

The invention encompasses modified immune cells. The immune cells of the invention encompass any type of cell of the immune system. In a preferred embodiment, the immune cells of the invention are dendritic cells. A modified immune cell as used herein is an immune cell which has been engineered in order to modify its properties and, as a consequence, the behavior of the immune system (see e.g., Porter, D. L. et al. N. Engl. J. Med. doi:10.1056/nejmoa1103849, 2011; Kalos, M. et al. Sci. Transl. Med. 3, 95ra73; 2011; Brentjens, R. J. et al. Sci. Transl. Med. 5, 177ra38, 2013). Preferably, said modified immune cell has been genetically modified. More preferably, said genetically modified immune cell expresses a protein or an RNA. The immune cells can be loaded with a protein. See U.S. Pat. No. 7,414,108. The immune cells can be loaded with an RNA. See U.S. Pat. No. 7,105,157, which is hereby incorporated by reference.

The immune cell therapy can be SIPLEUCEL T, BELAGENPUMATUCEL-L, or TERGENPUMATUCEL-L (Villaruz et al. Transl Lung Cancer Res. 2014 February; 3(1): 2-14.), incorporated herein by reference.

In a preferred embodiment, the modified immune cell is a dendritic cell that expresses a PAP antigen.

The invention encompasses modified immune cells including T cells expressing chimeric antigen receptors (CARs) and T cells modified through altering the specificity of the T cell receptor (TCRs) targeting and TAAs, particularly those detailed herein. TCRs, and CARs and immune cells expressing them, can be produced using routine techniques in the art, for example, those set forth in U.S. Pat. Nos. 8,088,379, 8,785,601, 5,359,046 and 8,389,282, which are hereby incorporated by reference.

In a preferred embodiment, the modified immune cell expresses a chimeric antigen receptor (CAR) or is a TCR directed against CD19, melanoma-associated antigen recognized by T cells 1 (MART-1), glycoprotein (gp) 100, carcinoembryonic antigen (CEA), p53, MAGE-A3, or New York esophageal squamous cell carcinoma antigen (NY-ESO-1).

In preferred embodiments, the modified immune cell expresses a chimeric antigen receptor (CAR) or is a TCR directed against folate receptor (FR) (preferably in ovarian cancer), carbonic anhydrase IX (CAIX) (preferably in renal cell carcinoma), L1-cell adhesion molecule (L1-CAM; CD171), CD20 (preferably in indolent non-Hodgkin lymphoma), and diasialoganglioside GD2 (preferably in neuroblastoma).

In preferred embodiments, the modified immune cell expresses a chimeric antigen receptor (CAR) or is a TCR directed against CD19, HER-2, or CEA.

Preferably, the CAR comprises a single chain antibody, preferably a humanized scFv or an scFv derived from a human monoclonal antibody, directed against a tumor TSA or TAA.

In a preferred embodiment, the immune cell has been modified with a vector, particularly a plasmid, a poxvirus, an adenovirus, an adeno-associated virus, an integrative or non-integrative lentivirus, or a measles virus vector. In a particularly preferred embodiment, the lentivrus technology set forth in U.S. Pat. No. 8,460,678 is used to construct the modified immune cell.

Cytokines

By "cytokine", it is herein referred to a group of cell signaling proteins that aid cell to cell communication in immune responses and stimulate the movement of cells towards sites of inflammation, infection and trauma. Cytokines are classified as being proinflammatory (T helper 1, Th1) or anti-inflammatory (T helper 2, Th2) depending on their effects on the immune system.

The invention encompasses the use of cytokines as anti-cancer immunotherapeutics. Particularly preferred cytokines include interleukin or interferon. Particularly preferred cytokines are GM-CSF, IL-12, IL-2, interferon-α2b, and IFN-y.

Immune Checkpoint Blockade Molecule

An "immune checkpoint" as used herein refers to an inhibitory pathway hardwired into the immune system that is crucial for maintaining self-tolerance and modulating the duration and amplitude of physiological immune responses in peripheral tissues in order to minimize collateral tissue damage. The expression of immune-checkpoint proteins is known to be dysregulated in at least some tumors as an important immune resistance mechanism, in particular against T cells. An "immune checkpoint blockade molecule", as used herein, is a molecule which blocks said immune checkpoint, thus overriding the immune resistance of the tumor. Immune checkpoints and immune checkpoint blockade molecule are well-known in the literature. See e.g., *Nature Reviews Cancer* 12: 252-264, April 2012).

In various embodiments, the invention encompasses an immune checkpoint blockade molecule, preferably a monoclonal antibody, which targets CTLA-4, PD-L1 or PD-1.

In various embodiments, the anti-cancer immunotherapeutic comprises a monoclonal antibody that targets CD27, CD28, CD40, CD122, CD137, B7-H3, B7-H4, A2R2, ICOS, VISTA, B7-H3, KIR, IDO, BTLA, GITR, OX40, LAG-3 or TIM-3/Tim-3L.

In some embodiments, the anti-cancer immunotherapeutic comprises multiple antibodies, including combinations of 2 or 3 antibodies targeted against CD27, CD28, CD40, CD122, CD137, B7-H3, B7-H4, A2R2, ICOS, VISTA, B7-H3, KIR, IDO, BTLA, CTLA-4, PD-L1, PD-1, GITR, OX40, LAG-3 or TIM-3/Tim-3L. In a preferred embodiment, the anti-cancer immunotherapeutic comprises antibodies targeting PD-1 and LAG-3.

In preferred embodiments, the monoclonal antibody is NIVOLUMAB, an IgG4 anti-PD-1 monoclonal antibody that acts as an immunomodulator by blocking ligand activation of the programmed cell death 1 (PD-1) receptor on activated T cells. Preferably, it is used for patients with metastatic melanoma or for the treatment of squamous non-small cell lung cancer.

PEMBROLIZUMAB is a humanized monoclonal antibody that targets the programmed cell death 1 (PD-1) receptor. Preferably, it is for use following treatment with IPILIMUMAB, or after treatment with IPILIMUMAB and a BRAF inhibitor in advanced melanoma patients who carry a BRAF mutation.

Virus and Nucleic Acid Vectors

In still another embodiment, the invention is directed to a composition for immunotherapy comprising a DDP4i, and a nucleic acid vector expressing an antigen such as one of the antigens described above.

In a preferred embodiment, the vector is a plasmid vector.

Vectors are well-known in the art and include measles virus, lentivirus, retrovirus, adenovirus, poxvirus, herpes virus, measles virus, foamy virus or adeno-associated virus (AAV). Viral vectors can be replication-competent, or can be genetically disabled so as to be replication-defective or replication-impaired. Suitable vectors can be integrative or non-integrative.

In one embodiment, the vector is an Alphavirus vector. Alphaviruses are single-stranded positive-sense RNA viruses that replicate in the cytoplasm of infected cells. In various embodiments, the vector is a Venezuelan equine encephalitis virus (VEE), Sindbis virus (SIN), Semliki forest virus (SFV), and VEE-SIN chimera vector.

In various embodiments, the vector is a poxvirus, preferably a vaccinia virus, vector. In one embodiment, the poxvirus vector expresses a tumor antigen, such as prostate-specific antigen (PSA) or CEA, and multiple human T-cell co-stimulatory molecules (B7.1, LFA-3, and intracellular adhesion molecule-1). In various embodiments, the poxvirus vector is a replicating poxviral vector selected from attenuated modified vaccinia virus Ankara (MVA), NYVAC (derived from the Copenhagen strain of vaccinia), and ALVAC (canarypoxviral vector) strains.

In various embodiments, the vector is a lentiviral vector. Preferred vectors are the DNA Flap vectors as described in WO 99/055892, U.S. Pat. No. 6,682,507 and WO 01/27300, and U.S. Pat. No. 8,460,678, which are hereby incorporated by reference.

In a preferred embodiment, the virus expresses a 5T4 tumor-associated antigen. The nucleic acid vector can be an mRNA. Preferable, the mRNA is a modified mRNA, preferably in a nanoparticle. See, e.g., U.S. Pat. Nos. 8,664,194, 8,754,062, and 8,999,380, which are hereby incorporated by reference.

Methods for Treating a Cancer Patient

The invention encompasses methods for treating a cancer patient. In one embodiment, the invention encompasses a method for enhancing anti-cancer immune responses in a patient comprising administering to the patient a combination of a DPP4 inhibitor and an anti-cancer immunotherapeutic.

The invention also relates to a combination of a DPP4 inhibitor and an anti-cancer immunotherapeutic for use in the treatment of cancer, wherein anti-cancer immune responses are enhanced.

The cancer can be selected from the group consisting of basal cell carcinoma, biliary tract cancer, bladder cancer, bone cancer, brain cancer, breast cancer, cervical cancer, choriocarcinoma, CNS cancer, colon and rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, liver cancer, small cell lung cancer, non-small cell lung cancer, lymphoma, Hodgkin's lymphoma, Non-Hodgkin's lymphoma, melanoma, neuroblastoma, oral cavity cancer, ovarian cancer, pancreatic cancer, prostate cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancer of the urinary system.

In other embodiments, the cancer is selected from the group consisting of prostate cancer, colorectal cancer, multiple myeloma, and non-small cell lung cancer. In certain other embodiments, the cancer is selected from lung cancer, colorectal cancer, breast cancer, pancreatic cancer and prostate cancer. Preferably, the cancer is selected from melanoma, colorectal carcinoma, synovial sarcoma, prostate cancer, breast cancer, lung cancer, and pancreatic cancer. Most preferably, the cancer is metastatic.

Preferably the cancer is a solid cancer, most preferably a DPP4—overexpressing cancer.

DPP4-overexpressing cancers include non-melanoma skin cancer. See., Rinkevich et al., Science. 2015 Apr. 17; 348(6232); Arwert et al. Oncogene. 2012 Feb. 23; 31(8): 992-1000; and Starska et al., Part I. Folia Histochem Cytobiol. 2011; 49:579-592.

DPP4-overexpressing cancers include colorectal cancer. See., Pang et al. (2010) Cell stem cell 6: 603-615.

DPP4-overexpressing cancers include mesothelioma. See., Amatya et al., Oncol Rep. 2011 December; 26(6): 1369-75; Inamoto et al. (2007) Clin Cancer Res 13:4191-4200.

DPP4-overexpressing cancers include mesothelioma. See., Stange et al., (2000) Eur J Histochem 44:157-164.

DPP4—overexpressing cancers include breast cancer. See., Leccia et al., Cytometry A. 2012; 81:960-972; Wilson et al., Int J Oncol. 2012; 41:919-932.

DPP4-overexpressing cancers include glioma. See., Mares et al., Histol Histopathol. 2012; 27:931-940.

Dosages of compounds are as routine in the art. Normally, the amount of DPP4 inhibitor will be between 1-1000 mg/day, preferably between 1-800, 1-600, 1-400, 1-200, and 1-100 mg/day. This can be provided in a single dose or in multiple doses (e.g., 2, 3,4 doses/day). Preferably, sitagliptin is administered at 25-100, 200, 400, 600, or 800 mg/day. Preferably, saxagliptin is administered at 2.5-5, 10, 20, 30, or 40 mg/day.

Preferably, linagliptin is administered at 5 mg/day. Preferably, alogliptin is administered at 6.25-25, 50, 100, 150, or 200 mg/day.

EXAMPLES

Example 1. Mice

WT C57BL/6 CD45.2 Thy1.2 and BALB/c mice were obtained from Charles Rivers, France. WT C57BL/6

CD45.1, Rag2$^{-/-}$, Cxcr3$^{-/-}$, Ifnar1$^{-/-}$Dpp4$^{+/-}$, Dpp4$^{-/-}$, Cxcl10$^{-/-}$, Ccr5$^{-/-}$, Pmel-1 Thy-1.1$^+$Thy-1.1$^+$, OT1 and FVB-Tg(CAG-luc) mice were bred in our mouse facility. Male Pmel-1 Thy-1.1$^+$Thy-1.1$^+$ mice were crossed with female Cxcr3$^{-/-}$ Thy-1.2$^+$Thy-1.2$^+$, mice to obtain first generation males that were Pmel-1 Cxcr3$^{-/-}$ Thy-1.1$^+$Thy-1.2$^+$. Mice used were 7-12 weeks old. For inhibition of DPP4 activity in vivo, mice were fed with chow (SAFE) formulated to contain 1.1% Sitagliptin (trade name Januvia, Merck). Sitagliptin food was administrated to mice before treatments, unless stated differently in the figure legend. Mice were maintained in a specific pathogen free facility and all experimental protocols were approved by the Comité d'Ethique pour l'Expérimentation Animale (The ethics committee for animal experimentation) Paris.

Example 2. Mass Spectrometry

Recombinant mDPP4, mCXCL10, mCXCL9, mCXCL11, mCCL2, mCCL3, mCCL4, mCCL5, mCXCL12 and mCCL22 were purchased from Peprotech. For surface-enhanced laser desorption/ionization-time-of-light (SELDI-TOF) mass spectrometry, chemokines were incubated in the presence or absence of 10 nM of mDPP4 for 30 min at 37° C. The digested product was applied onto an H4 protein chip, following the manufacturer's instructions and analyzed using the PROTEINCHIP™ SYSTEMS SERIES 4000 (Ciphergen). Data were analyzed using CIPHERGENEX-PRESS Software.

Example 3. Model of Trafficking into the Peritoneal Cavity

WT and Dpp4$^{-/-}$ mice were intraperitoneally injected with PBS or 1 µg of mCXCL10, mCXCL9 or mCCL5 (all from Peprotech). At the indicated time points, mice were sacrificed and peritoneal cells were collected in 10 mL of PBS. For thioglycollate induced peritonitis mice were intraperitoneally injected with thioglycollate 3% weight/volume, 24 hours before collection of peritoneal cells.

Example 4. DPP4 Enzymatic Activity

For evaluation of DPP4 enzymatic activity, mice were bled at the time points indicated and plasma samples were collected after centrifugation of blood. For measurements of DPP4 activity in tumor homogenates, tumors growing in mice were dissected, weighted and homogenized in PBS supplemented with protease inhibitor cocktail (Roche). Soluble extracts were collected after centrifugation of tumor homogenates. DPP4 activity in peritoneal cavity was measured by collecting peritoneal washes in 1.5 ml of PBS. DPP4 activity was measured using the DPPIV-GLO™ Protease assay (Promega). To evaluate DPP4 activity in vivo, FVB-Tg(CAG-luc) mice were fed with control and sitagliptin chow 24 hours prior to intraperitoneal injection of 10 mM Gly-Pro-aminoluciferin (Promega). Bioluminescence images were acquired with a XENOGEN (IVIS system, Perkin Elmer), 5 min after injection.

Example 5. Tumor Growth In Vivo

B16F10 and M04 (Ovalbumin-expressing B16F10 cells, gift from C. Reis e Sousa) tumor cells were cultured in DMEM (Gibco) supplemented with 10% FCS (PAA), 0.1 mM non-essential amino acids, 1 mM sodium pyruvate, 10 mM Hepes, 70 µM beta-mercaptoethanol and 23 µg/ml gentamycin (all from Gibco). CT26 colon carcinoma cells were cultured in RPMI (Gibco) supplemented as described for DMEM. Cells for injections were passaged 1-2 times after thawing, before use. WT and genetically modified mice were subcutaneously injected with 2×10$^5$ B16 or 5×10$^5$ CT26 cells in the shaved right flank. When indicated, mice received an intra-tumoral injection of 1 µg of recombinant mCXCL10, 5 µg CpG-A in DOPTAP or vehicle control. For blocking of chemokine and chemokine receptors, WT mice were intraperitoneally injected with 100 µg of hamster a-mCXCR3 (clone CXCR3-173, BioLegend), 100 µg of hamster α-mCCR5 (clone HM-CCR5, BioLegend), 50 µg of rat anti-mCXCL10 (clone 134013, R&D systems) and 20 µg of rat-α-mCXCR4 (clone 2B11/CXCR4, BD Biosciences) or with respective isotype antibodies (hamster IgG (clone HTK888, BioLegend, used as control for mCXCR3 and mCCR5 blockage); rat IgG2a (clone 54447, R&D systems, used as control for mCXCL10 blockade) and rat IgG2b (clone A95-1, BD Biosciences, used as control for mCXCR4 blockade). Intraperitoneal injection was done one day before and 4, 8 and 12 days after tumor cell injection. For CXCL10 neutralization, antibodies were injected on day 2, 5, 8 and 11 after tumor cell injection. For immunotherapy protocols, mice were intraperitoneally injected with 100 µg of mouse α-CTLA-4 (clone 9D9, Bioxcell), 200 µg of PD1 (clone RMP1-14, Bioxcell), a combination of 100 µg of α-CTLA-4+200 µg of a-PD1 or control isotypes (100 µg rat IgG2b (clone MPC-11) and 200 µg rat IgG2a (clone 2A3), both from Bioxcell) on day 3, 6 and 9 after tumor cell implantation. For adoptive cell transfer experiments, Pmel-1 Thy-1.1$^+$Thy-1.1$^+$, Cxcr3$^{-/-}$ Thy-1.1$^+$Thy-1.2$^+$ Pmel-1 or OT1 splenocytes were activated ex-vivo, by incubation with 1 nM of human gp100 (for Pmel-1 cells) or SIINFEKLL (for OT1 cells) peptides for 1h at room temperature with agitation. Splenocytes were then washed and resuspended in R10 supplemented with 30U/mL of recombinant human IL-2. CD8$^+$ T cells were expanded for 6-7 days before used. For analysis of tumor infiltrates, activated Cxcr3$^{+/+}$ Thy-1.1$^+$Thy-1.1$^+$ and Cxcr3$^{-/-}$ Thy-1.1$^+$Thy-1.2$^+$ transgenic Pmel-1 CD8$^+$ T cells were mixed in a 1:1 ratio (total 1×10$^6$ cells) and injected intravenously into gender matched tumor-bearing mice (3 days after tumor cell injection). For analysis of tumor growth, activated OT1 cells were injected intravenously (1×10$^5$ cells per mouse) into gender matched tumor-bearing mice, 3 days after tumor cell injection. Tumor height and width were measured with a caliper and tumor volume was calculated (Elliptical volume=width$^2$×height×0.523). The model of metastatic melanoma was achieved by intravenous injection of 2×10$^5$ B16 tumor cells. 15 days after tumor cell injection, lungs were dissected, placed in Fekete's solution and metastatic foci were counted. Lungs with more than 100 metastatic nodules were defined as 100.

Example 6. Flow Cytometry

Fluorochrome-conjugated anti-mouse CD3 (clone145-2C11), CD8 (clone 53-6.7), CD4 (clone RM4-5), NK1.1 (clone PK136), CD49b (clone DX5), CD25 (clone PC61), B220 (clone RA3-6B2), Ly6G (clone 1A8), Ly6C (clone AL-21), CD11 b (clone M1/70) Siglec-F (clone E50-2440), MHCII IA-IE (clone M5/114.15.2), CD45.2 (clones 56-0454-82 and 109830), Thy-1.1 (clone HIS51), Thy-1.2 (clone 53-2.1), DPP4 (clone H194-112) and CXCR3 (clone CXCR3-173) were from eBiosciences and BD Biosciences. Fluorochrome conjugated anti-F4/80 (clone CI:A3-1) was from AbDserotec. For exclusion of dead cells, Live/Dead fixable Aqua reagent (Invitrogen) was used. For all staining protocols, cell suspensions were incubated with mouse CD16/CD32 Fc Blocking antibodies (BD Biosciences) prior to antibody. For analysis of peritoneal cavity infiltrates, cells were washed and incubated with a cocktail of fluorochrome-conjugated antibodies. For analysis of tumor infiltrates, B16F10 tumors were collected at the indicated time points and digested in PBS supplemented with 2.7 mg/ml of Collagenase (Roche) and 23U/ml of Deoxyribonuclease I (Invitrogen) for 30 min, 37° C. Digestion was terminated by adding PBS supplemented with 2% FCS and 5 mM EDTA (Gibco). Tumor cell suspensions were obtained after filtration over a 70 µm cell strainer. For determination of cell numbers, the ACCUCHECK COUNTING BEADS reagent (Invitrogen) was used. Flow cytometry was performed using a BD LSRFORTESSA or a BD CANTO cytometer, with DIVA software. Computer analysis was done with FLOWJO (Treestar).

Example 7. Histology

B16F10 tumors were dissected and fixed in JB fixative (zinc acetate 0.5%, zinc chloride 0.05%, and calcium acetate 0.05% in Tris buffer, pH 7) for 48 hours, prior to being embedded in low-melting point paraffin (Poly Ethylene Glycol Distearate; Sigma, USA). 5 µm thick paraffin sections were deparafinized in absolute ethanol, air dried, and routinely stained with hematoxylin-eosin or used for immunolabelling. For immunohistochemistry, the following primary antibodies were used: anti-CD3 (rabbit α-human, clone A0452, DAKO, Carpinteria, CA) and anti-CD31 (rat a-mouse, clone 1/75e, BD Pharmingen, Franklin Lake, NJ, USA). CD31 immunolabelled sections were digitalized using a Zeiss Axio Scan Z.1 at ×20. For histomorphometry of blood vessels, CD31 positive profiles were manually delineated on digitalized images, using the "area" tool of the Zen software (Zeiss) at a magnification of 30%. The whole tumor surface was also delineated in the same way at a magnification of 2%. Mean number of blood vessels per mm2 and mean vessel area were then calculated for each group of mice.

Example 8. In Vitro T Cell Migration and CXCR3 Internalization Assays

For evaluation of T cell migration upon different mCXCL10 isoforms, 5×105 activated Pmel-1 CD8+ T cells were resuspended in 100 µL of HBSS medium (Gibco) supplemented with 0.1% BSA and placed in the upper chamber of a 96 transwell plate containing 5 µm pores (Corning). T cells were allowed to migrate into the lower chamber, where no chemokine (medium only) or indicated concentrations of full length mCXCL10(1-77) and DPP4-truncated mCXCL10(3-77) were added. For evaluation of CXCR3 levels, activated Pmel-1 cells were incubated with indicated amounts of the chemokines in a 96U bottom plate. After 1h.30m, the number of cells migrating to the lower chamber, and levels of surface CXCR3 were evaluated by flow cytometry.

Example 9. ELISA/Luminex Assays

For detection of mCXCL10(1-77), MAXISORP PLATES® (Nunc) were coated with 4 µg/ml of α-mCXCL10 capturing antibody (MAB466, R&D) in PBS and incubated over night at 4° C. Plates were washed twice with 300 µL of PBS. Blocking was done with BSA 1% (proteinase free, Gibco), in PBS for 2h at room temperature. Plates were washed 3 times with 300 µL of 0.05% Tween-20 in PBS. Tumor and plasma samples were diluted in BSA 1% and incubated for 2h, at room temperature. To obtain a standard curve, and to control for the cross-reactivity of the detection antibody, dilutions of recombinant mCXCL10 (Peprotech) or DPP4-digested mCXCL10(3-77) were incubated in parallel. For detection of mCXCL10(1-77), biotinylated α-mCXCL10(1-77) (AbDSerotec, 0.5 µg/ml, clone AbD17185.1), Streptavidin-HRP (BD Biosciences) and 1-STEP ULTRA TMB (Thermo Scientific) were used.

Enzymatic reactions were stopped with HCL 1N and plates were read with 450 nm in a Lab-systems MULTISKAN MS (Thermo) reader. For detection of total mCXCL10, the MCXCL10 DUOSET® ELISA kit (R&D) or a combination of capturing α-mCXCL10 (MAB466) and biotinylated α-mCXCL10 (BAF466, both from R&D) were used, unless otherwise indicated. Detection of mDPP4, mCCL22 and mCXCL12 was done with the DUOSET® ELISA kit (R&D). Detection of mVEGF, mCCL2 and mCCL3 was done with a multiplex kit (Invitrogen).

Example 10. DPP4 Inhibition Enhances Anti-Tumor Responses to Melanoma

Figure 1C:
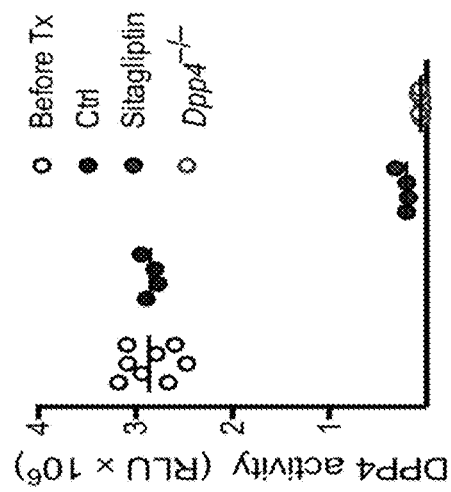
Figure 1B:
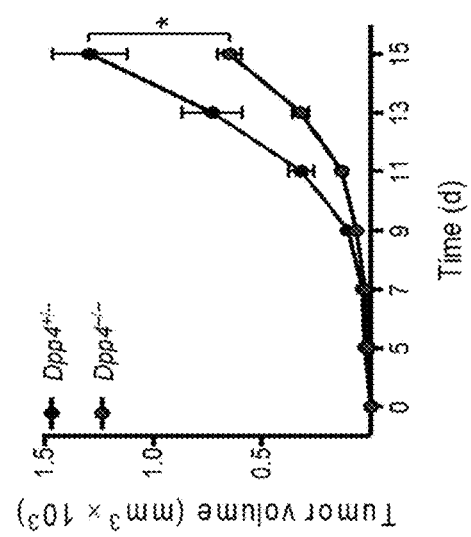
Figure 1A:
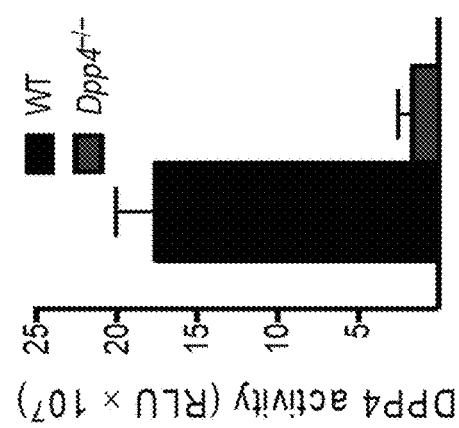
Figure 8A:
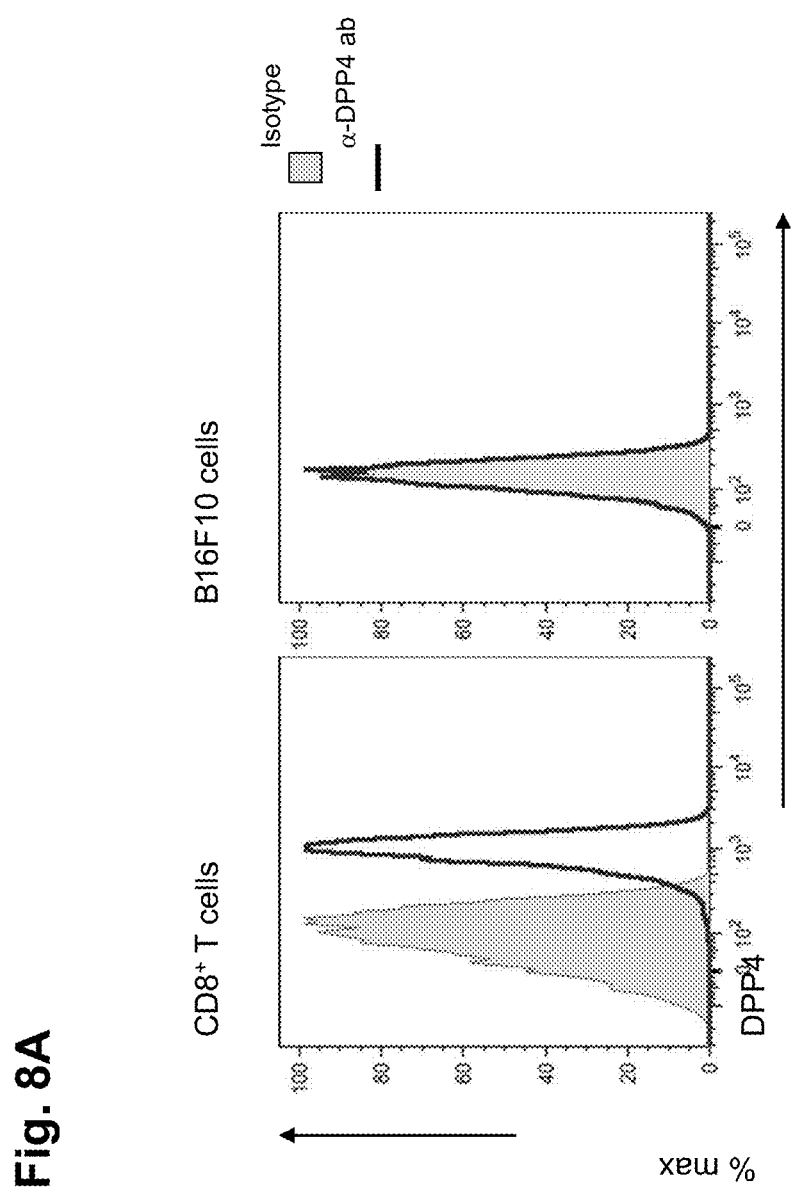
FIG. 8a-c. Expression of DPP4 in B16F10 cells and tumors. (a) C57BL/6 splenocytes and B16F10 melanoma cells were incubated with fluorochrome-conjugated anti-mDPP4 or with an isotype control. CD8+ T cells on splenocytes were gated and shown as positive control for DPP4 expression. (b) C57BL/6 wild-type (WT) and Dpp4–/– mice were subcutaneously injected with B16F10 cells. Eight days after injection, tumor homogenates were prepared and the DPP4 concentration was determined (bars represent mean±s.e.m.; n=3 (WT) and 4 (Dpp4–/–) mice). (c) Dpp4–/– mice were fed with control (ctrl) or sitagliptin chow prior to subcutaneous injection of B16F10 tumor cells. Tumor volumes are shown (data represent mean±s.e.m.; n=5 mice per group). Significance was determined using two-way ANOVA. Data are representative of 3 (a) and 2 (b,c) independent experiments.
Figure 8B:
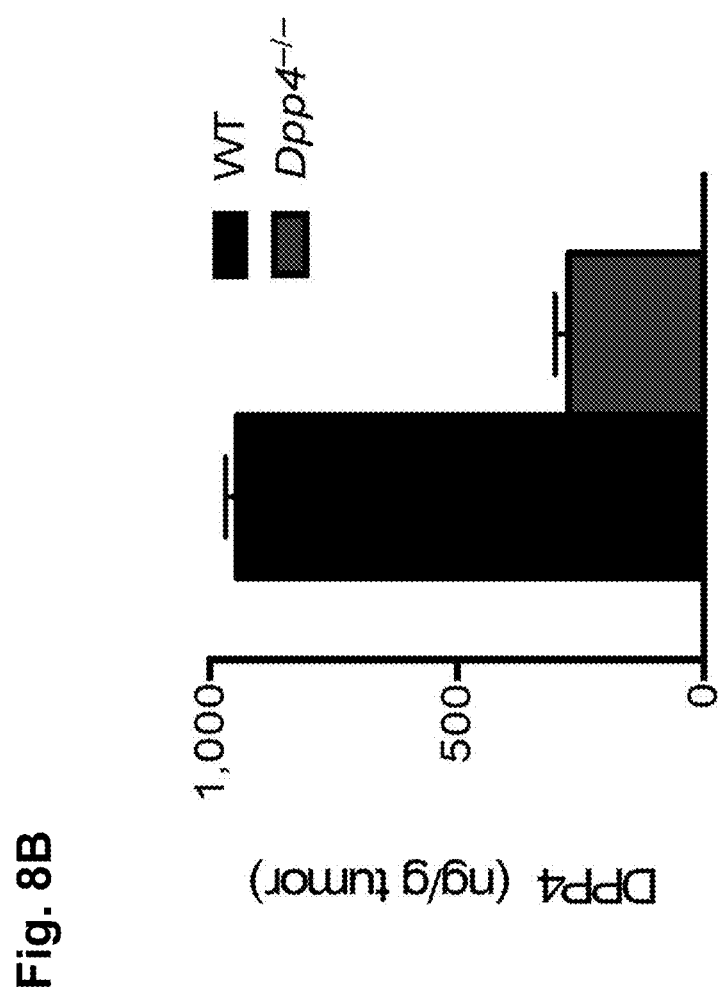

Despite data supporting T cell infiltration into solid tumors as a correlate of better prognosis[16,17], there remains no known therapeutic approach to direct lymphocytes into the tumor parenchyma. As the enzyme DPP4 was shown to modulate the activity of several immune molecules (including pro-inflammatory chemokines), we evaluated its role in tumorigenesis. First, we studied DPP4 expression in B16F10 tumor cells by flow cytometry. Although DPP4 was not expressed by in vitro cultured B16F10 cells (FIG. 8a), we detected high DDP4 activity and expression in excised B16F10 subcutaneous tumors, measured using an enzymatic assay and ELISA, respectively (FIG. 1a, FIG. 8b). Notably, tumor-associated DPP4 activity was detectable, but significantly lower when tumors were implanted into Dpp4$^{-/-}$ mice, thus suggesting contribution from both tumor cells and tumor-induced stroma. Next, we evaluated if DPP4 expression played a role in tumorigenesis, comparing tumor growth in Dpp4$^{-/-}$ mice and heterozygote littermates. We observed a significant delay in tumor growth when DPP4 was absent (FIG. 1b). To specifically evaluate the role of DPP4 enzymatic activity, we next fed wild-type mice with chow formulated to contain a DPP4 specific inhibitor called sitagliptin (also known by its trade name JANUVIA®). Use of sitagliptin chow also circumvents possible caveats due to developmental differences between wild-type and Dpp4$^{-/-}$ animals. Sitagliptin chow inhibited >80% of in vivo enzymatic activity (FIG. 1c), with no evidence of long-term drug intolerance or toxicity.

Figure 8C:
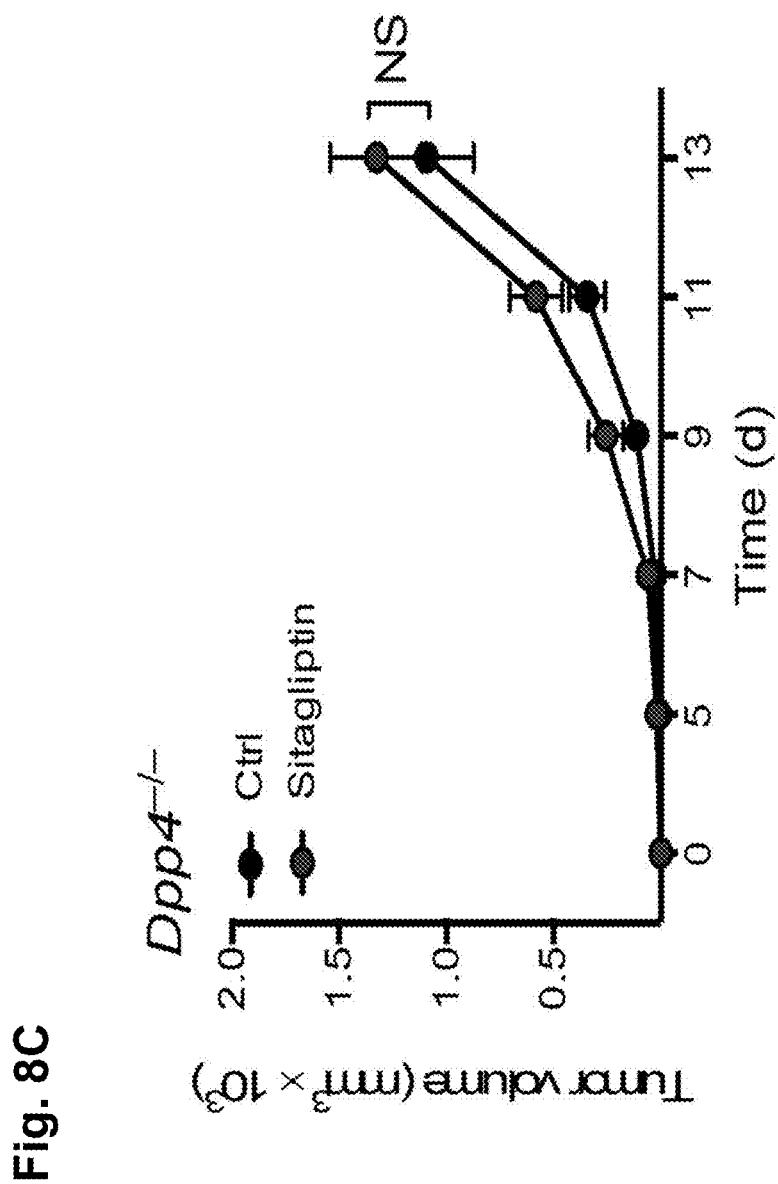

Furthermore, we demonstrated a reduced DPP4 enzymatic activity in the melanoma tumors extracted from mice (FIG. 1d). Notably, in vivo DPP4 inhibition resulted in reduced tumor growth (FIG. 1e). By contrast, sitagliptin treatment of Dpp4$^{-/-}$ mice did not influence the kinetics of melanoma growth (FIG. 8c), thus excluding off-target effects or direct cytotoxicity of the drug on the tumor.

Figure 1F:
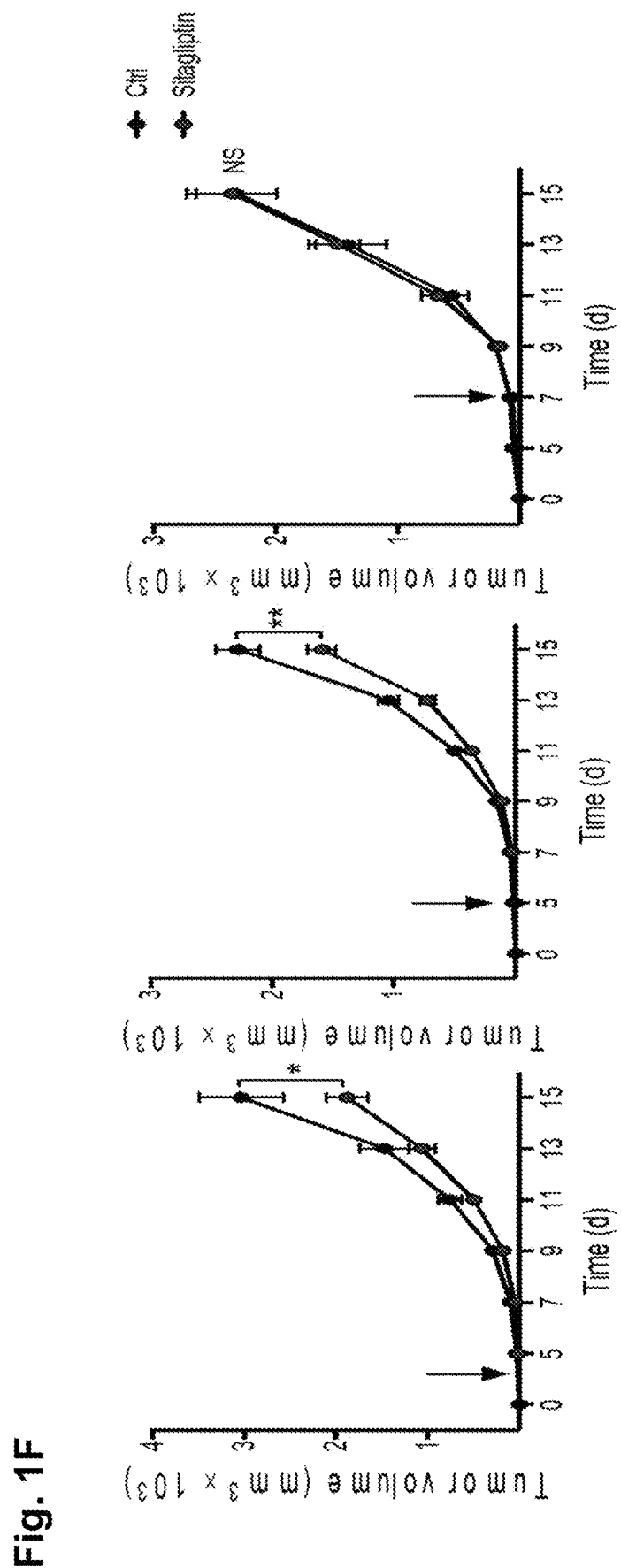
Figure 1G:
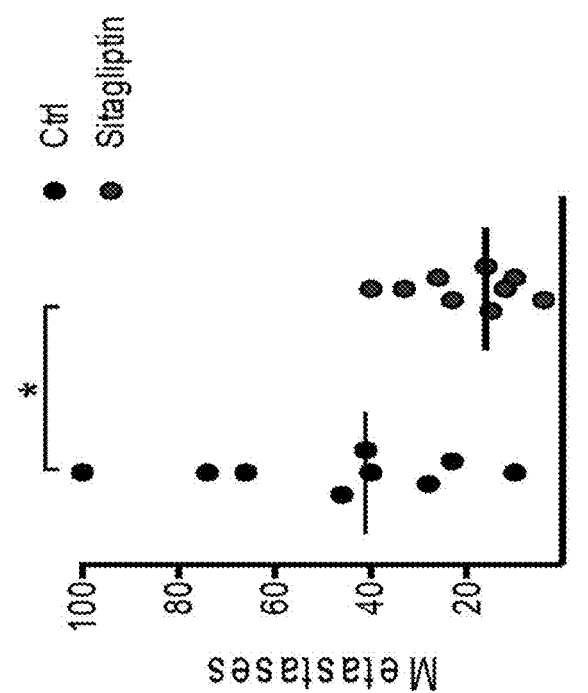
Figure 1G:
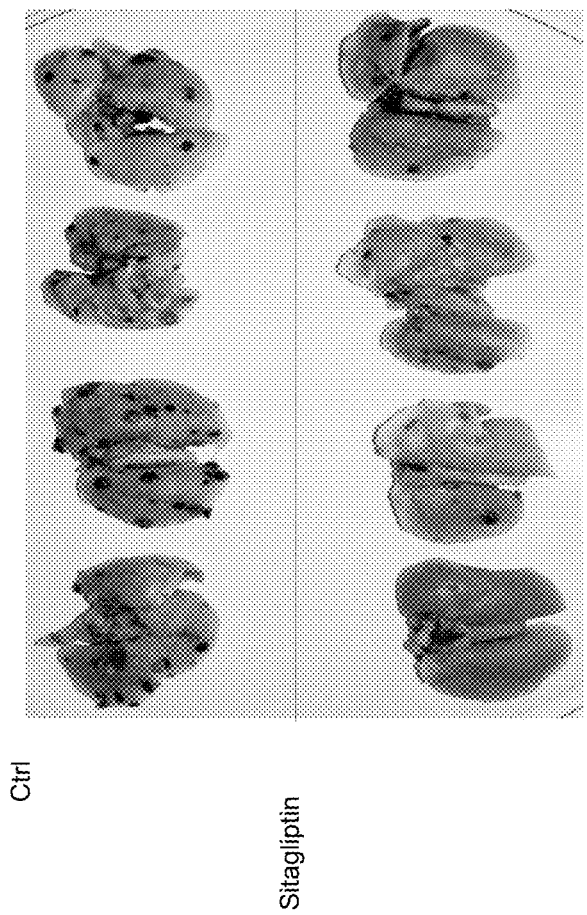

To evaluate DPP4 inhibition as a treatment for established tumors, we administrated sitagliptin chow to mice 3, 5 or 7 days after orthotopic tumor implantation. We observed a delay in tumor growth if sitagliptin was administrated within 5 days after tumor cell implantation (FIG. 1f). Finally, we assessed DPP4 inhibition in a model of metastatic melanoma, achieved by intravenous injection of B16F10 cells. DPP4 inhibition significantly reduced the number of lung metastases, as compared to control mice (FIG. 1g). These results suggest a role for DPP4 as a regulator of tumor growth in both orthotopic and metastatic models.

Example 11. Enhanced CXCL10 and CXCR3-Dependent Tumor Immunity

Figure 9B:
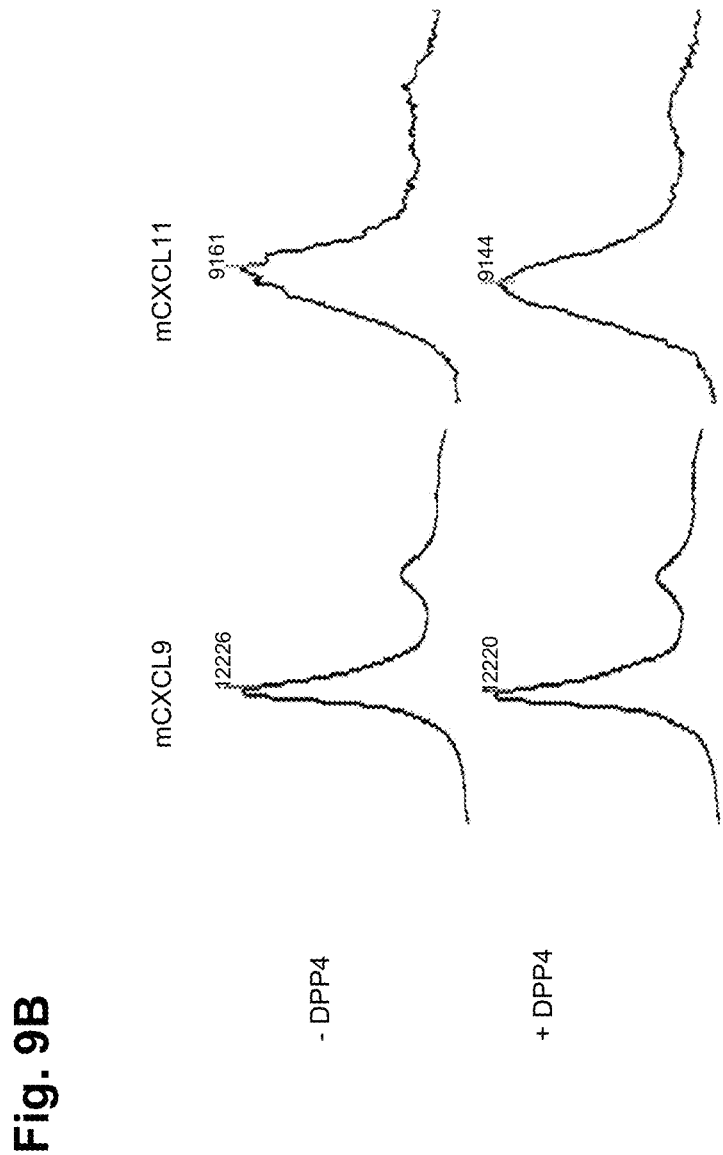
Figure 9C:
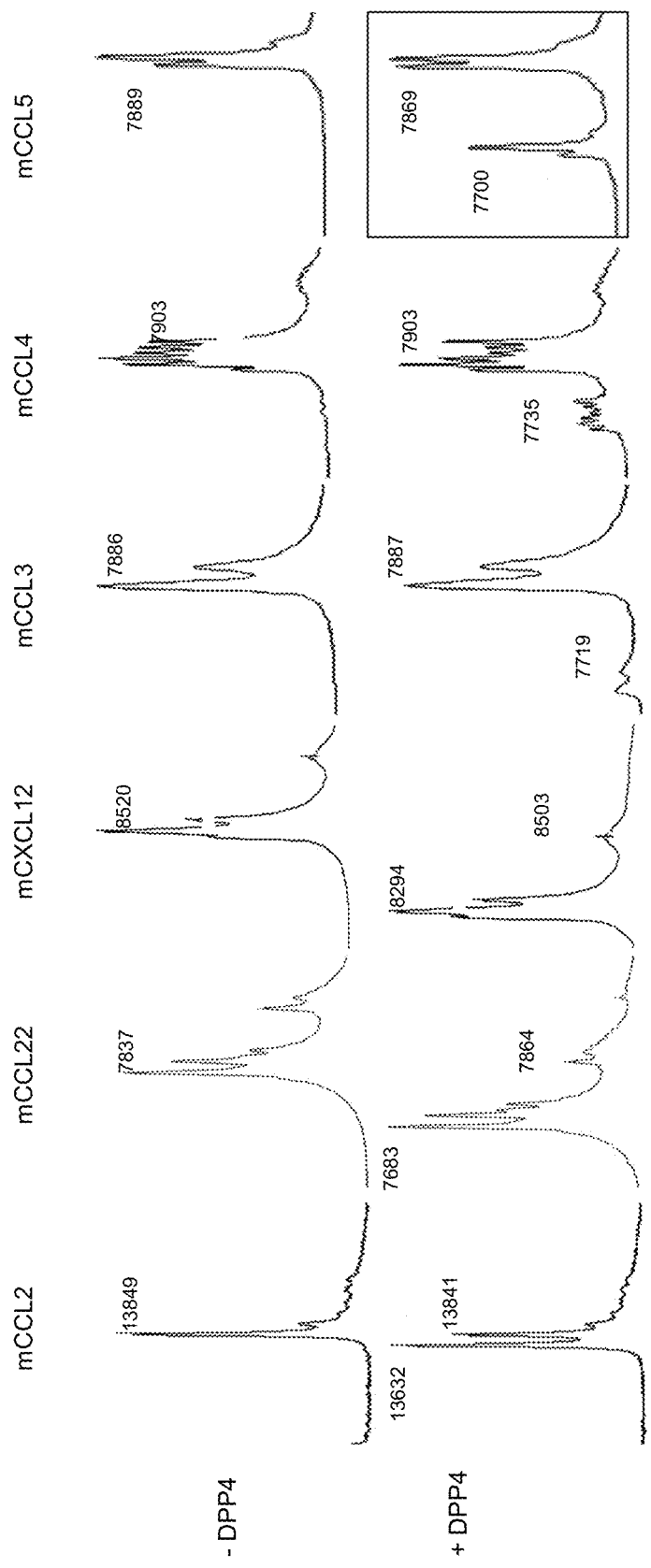

In vitro biochemical studies have established that DPP4 truncates chemokines and other immune molecules, thus initiating their catabolism and clearance by other N-terminal aminopeptidases[18]. To gain insight into the mechanism(s) accounting for delayed melanoma growth, we excised tumors growing in control and sitagliptin treated mice and quantified the expression of known DPP4 substrates. We observed elevated concentrations of tumor associated mouse (m)CXCL10 in B16F10 tumors growing in sitagliptin-treated mice, whereas the concentrations of mCCL2, mCCL22 and vascular endothelial growth factor (VEGF) were similar in treated and control animals (FIG. 2a and FIG. 9a). Of note, the potential DPP4 substrates mCXCL12 and mCCL3 were undetectable in the extracted tumors (data not shown). The in vivo protection of CXCL10 by sitagliptin is consistent with mCXCL10 being a substrate for DPP4 (FIG. 2b). Notably, mCXCL10 is the only alpha chemokine (achemokine) sensitive to DPP4 N-terminal truncation (FIG. 9b). Despite the lack of higher chemokine concentration in vivo, we confirmed the in vitro cleavage of putative DPP4 substrates that contain the X-Proline N-terminal motif—mCCL2, mCXCL12, mCCL22 and the three beta chemokines (B-chemokines) mCCL3, mCCL4, mCCL5 (FIG. 9c).

Figure 2D:
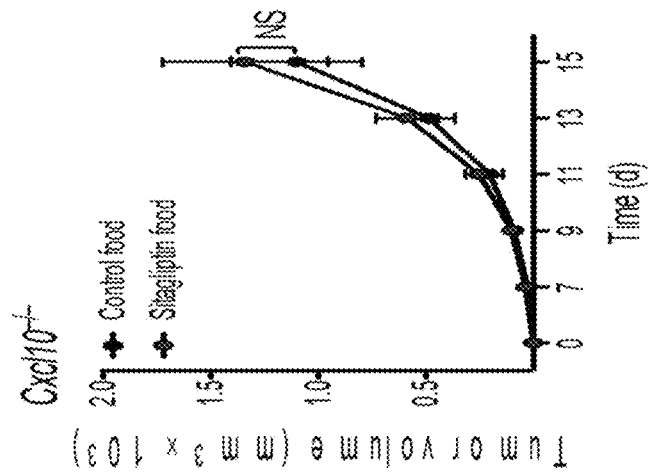
Figure 9D:
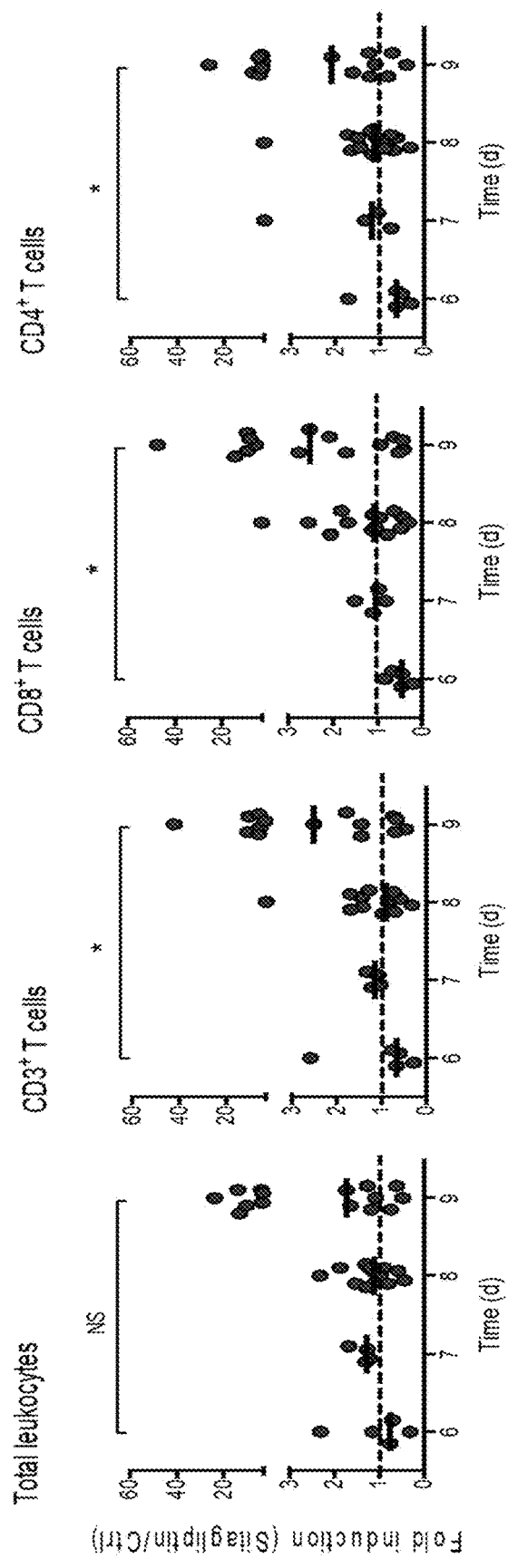

Higher concentrations of CXCL10 correlated with a significant increase in the number of CD4' and CD8$^+$ T cells localized to the tumors of sitagliptin treated animals (FIG. 2c and FIG. 9d). By contrast, no significant differences were seen in the number of tumor-infiltrating myeloid cells, NK cells, B lymphocytes or CD25$^{hi}$ regulatory T cells (FIG. 2c and data not shown). To directly assess the role of increased lymphocyte trafficking as the mechanism of action by which DPP4 inhibition impacts tumor growth, we first injected B16F10 melanoma cells into recombination activating gene 2 deficient (Rag2$^{-/-}$) mice, comparing sitagliptin or control treated animals. In the absence of adaptive immunity, the beneficial effects of DPP4 inhibition were lost (FIG. 2d). These results support a role for immune cells and prompted us to assess chemokine-mediated lymphocyte trafficking as the mechanism of action by which sitagliptin mediates tumor immunity.

Figure 2E:
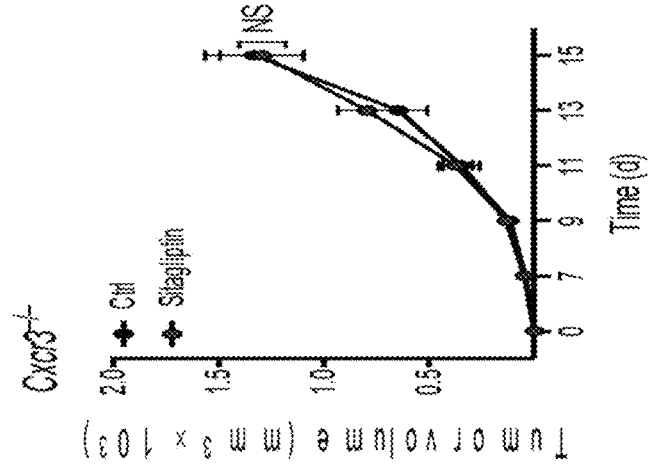
Figure 2F:
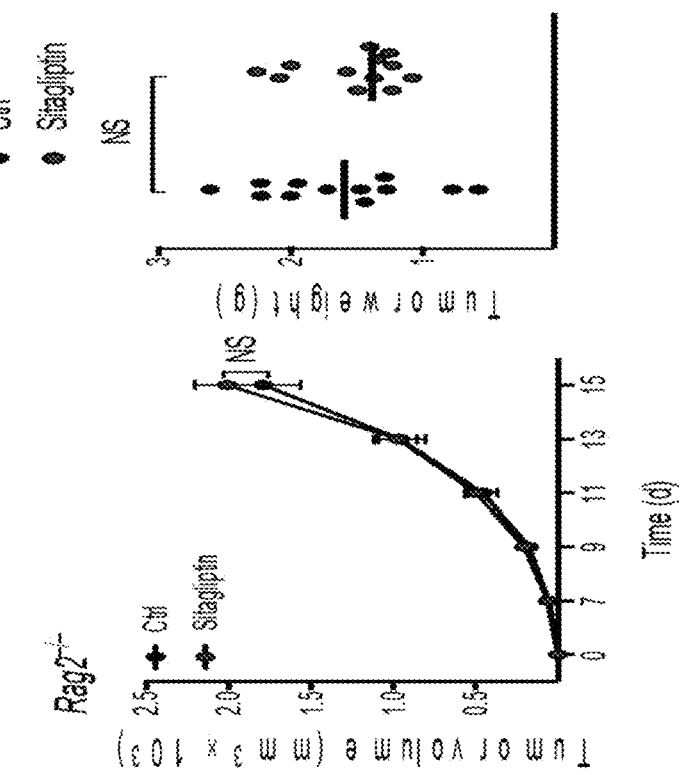
Figure 10A:
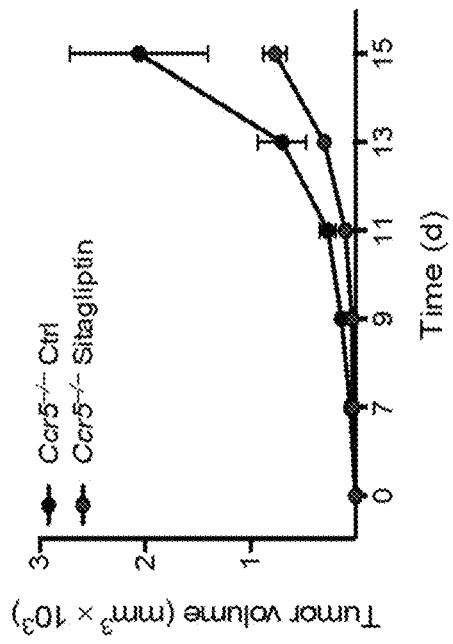
FIG. 10a-d. DPP4 inhibition enhances CXCL10-mediated antitumor responses to B16F10 melanoma. (a-d) WT (a, c and d) and Ccr5–/– (b) mice fed with ctrl or sitagliptin chow were subcutaneously injected with B16F10 cells. Mice were treated with blocking antibodies to (a) mCCR5, (c) mCXCR4 or (d) mCXCL10 and compared to their respective isotype ctrl-treated animals. Tumor volumes are shown (data represent mean±s.e.m.; n=12 (a), 4 (b) and 6 (c, d) mice per group, *P<0.05). Significance was determined using two-way ANOVA. Data are from 1 experiment (c,d), are representative of 2 independent experiments (b) or are pooled from 2 independent experiments (a).
Figure 10B:
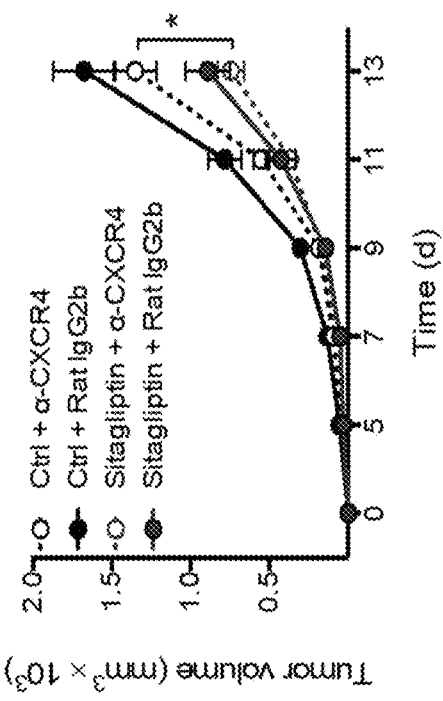
Figure 10C:
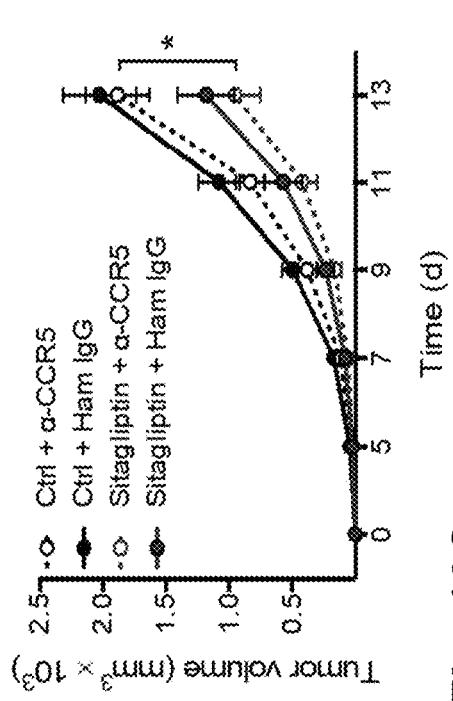

Migration of activated or memory lymphocytes is typically mediated by a- and B-chemokines[1], some of which are DPP4 substrates (FIG. 9b,c). We therefore tested if CXCR3 or CCR5 mediated the observed tumor immunity in sitagliptin-treated mice. The absence of CXCR3 (Cxcr3$^{-/-}$) abrogated the delayed tumor growth achieved by DPP4 inhibition (FIG. 2e). By contrast, CCR5 blockade or use of Ccr5$^{-/-}$ mice showed a similar beneficial effect of sitagliptin as seen in control or wild-type mice (FIG. 10a, b). Based on mCXCL10 being the sole CXCR3 ligand that can be post-translationally modified by DPP4, we next tested Cxcl10$^{-/-}$ mice. Similar to findings in Cxcr3$^{-/-}$ mice, the delayed tumor growth achieved by DPP4 inhibition was absent in Cxcl10$^{-/-}$ (FIG. 2f). These results were confirmed in wild-type animals treated with CXCL10 blocking antibodies (FIG. 10c).

Figure 2G:
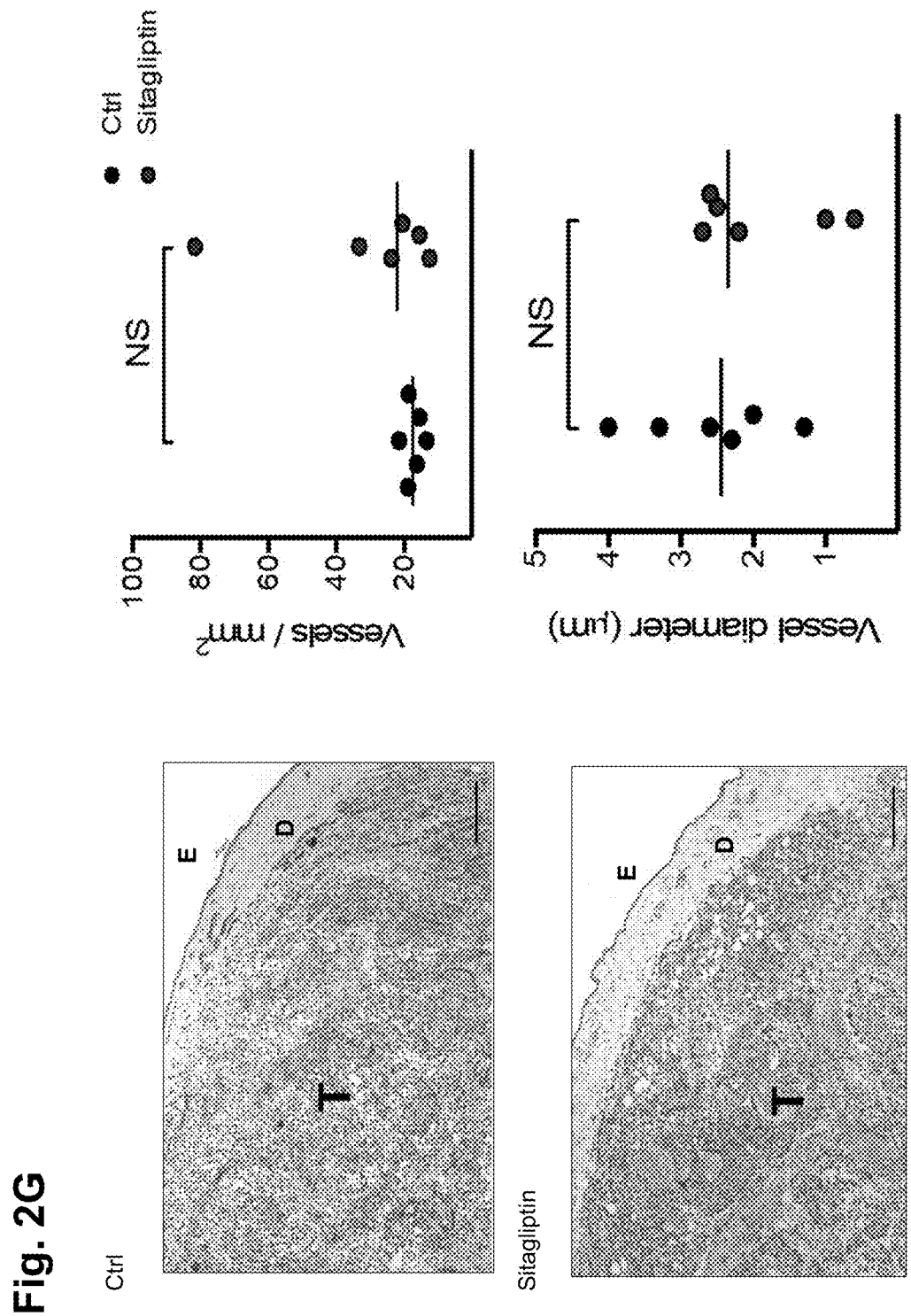
Figure 10D:
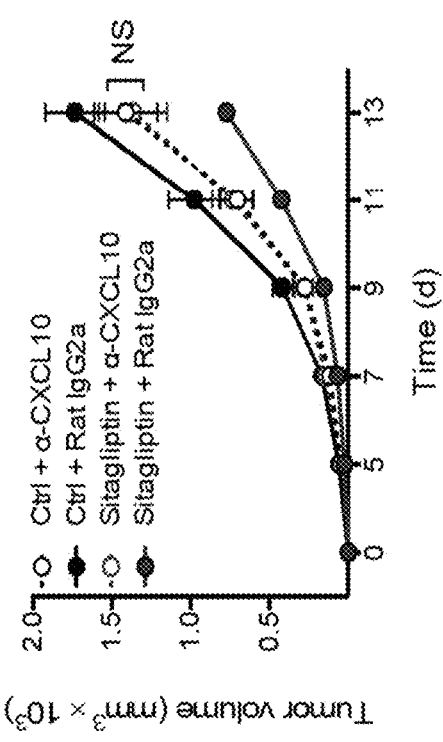

Although these data support a direct role for DPP4 protection of CXCL10 that in turn enhances tumor infiltrating lymphocytes and tumor immunity, other possible mechanisms of action were considered. First, we evaluated the reported angiostatic effects of CXCL10[19]. Histological analysis of tumors revealed no difference in the number, nor the diameter of blood vessels (as measured by CD31 staining) present in the tumors of untreated or sitagliptin-treated mice (FIG. 2g). Furthermore, the concentration of tumor associated VEFG was not altered by sitagliptin treatment (FIG. 9a). Additionally, CXCL12 being a substrate of DPP4[20] prompted us to consider the reported observation that CXCR4 antagonists modulate tumor growth. As indicated above, we did not detect CXCL12 expression within the growing tumors (data not shown). Moreover, blocking CXCR4 in vivo did not impact sitagliptin-mediated inhibition of tumor growth (FIG. 10d). These results support our conclusion that protection of CXCL10 within the tumor and CXCR3-directed migration of lymphocytes account for the enhanced tumor immunity when DPP4 activity is inhibited.

Figure 3A:
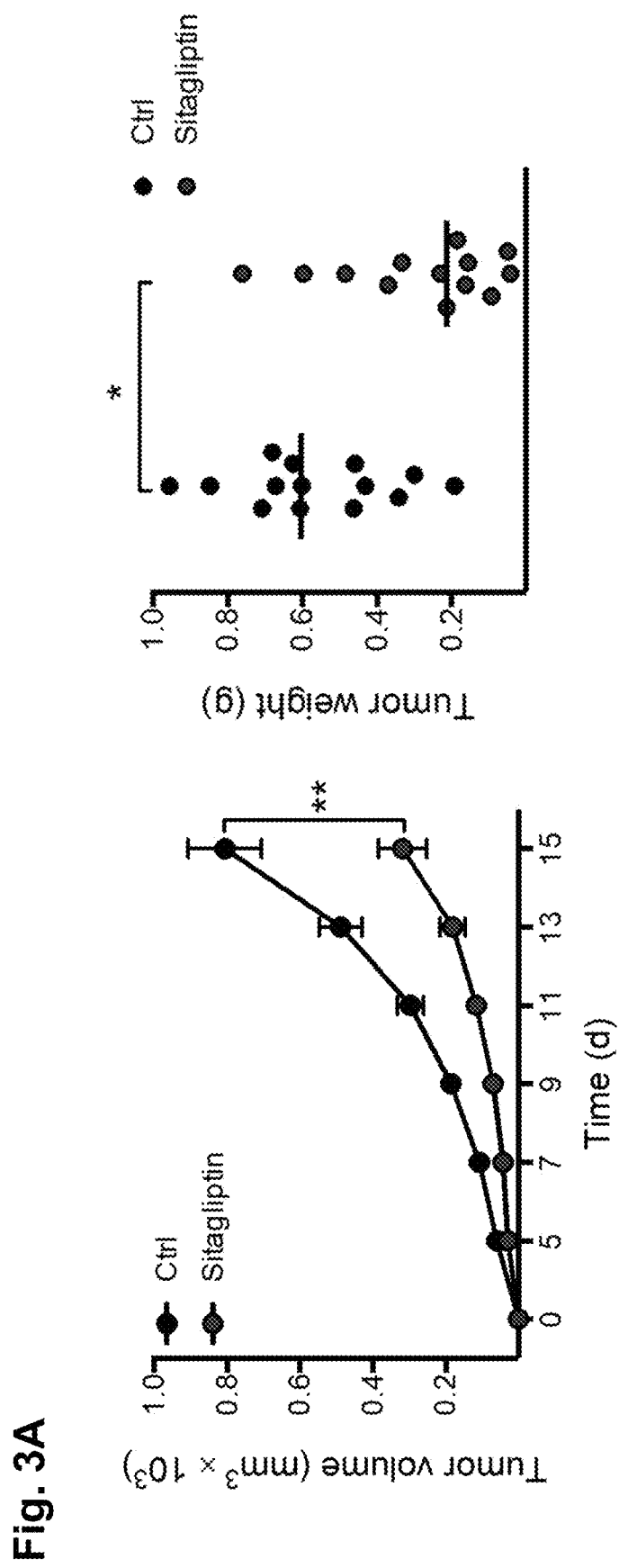
FIG. 3a-c. DPP4 inhibition enhances CXCR3-mediated immunity to CT26 tumors. (a) BALB/c WT mice fed with control or sitagliptin chow were subcutaneously injected with 5×10$^5$ CT26 cells. Tumor volumes and weights (on day 15) are shown (mean±SEM, * P<0.01; ** P<0.001). (b) tumors were excised on day 11 and the number of infiltrating leukocyte populations was evaluated (* P<0.05, ** P<0.005). (c) Mice fed with control or sitagliptin food were treated with □-CXCR3 blocking antibodies or the corresponding isotype control (hamster IgG, ham IgG). Tumor volumes are shown (mean±SEM, n=5 mice per group, * P<0.05). Circles represent individual mice. Significance was determined using 2Way Anova (a—left panel and c) and Mann-Whitney (a—right panel and b). Data are from 1 experiment representative of 2 (b, c); or pooled from 2 (a) independent experiments.
Figure 3B:
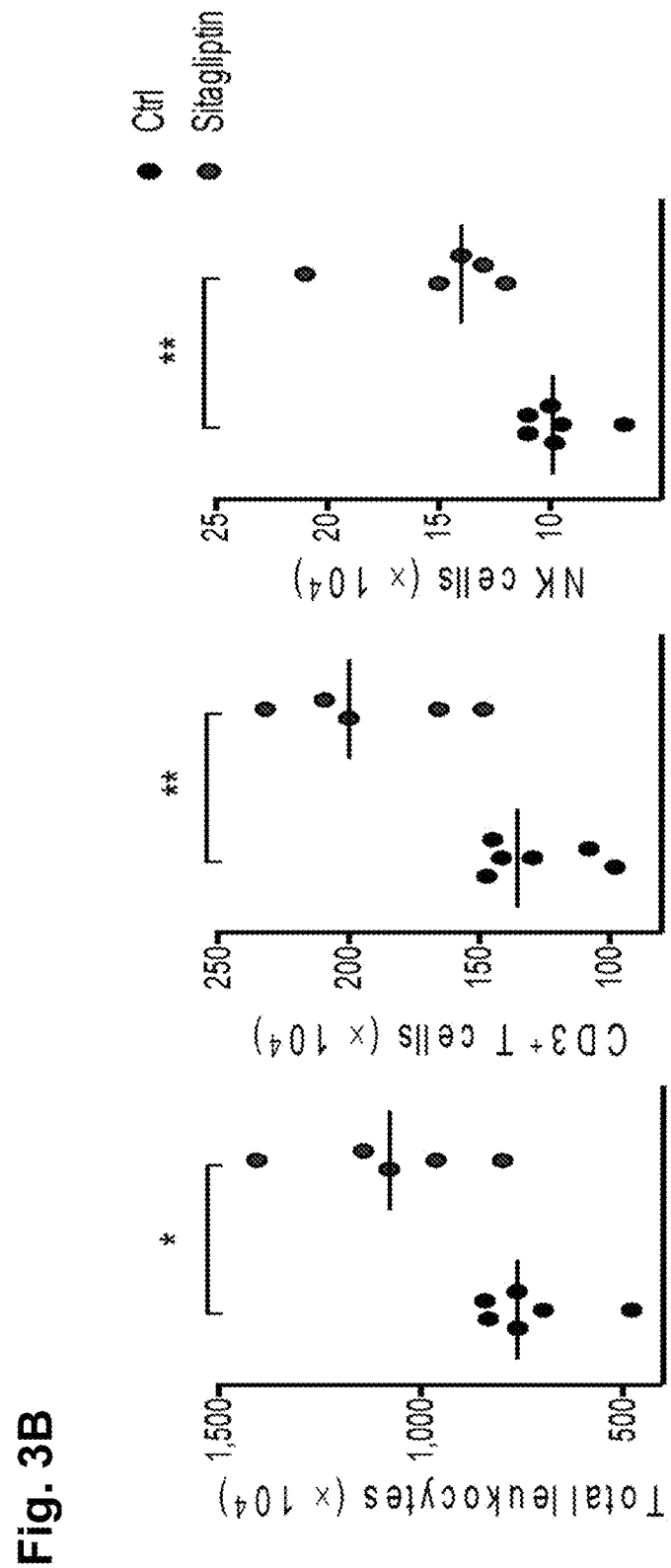
Figure 3C:
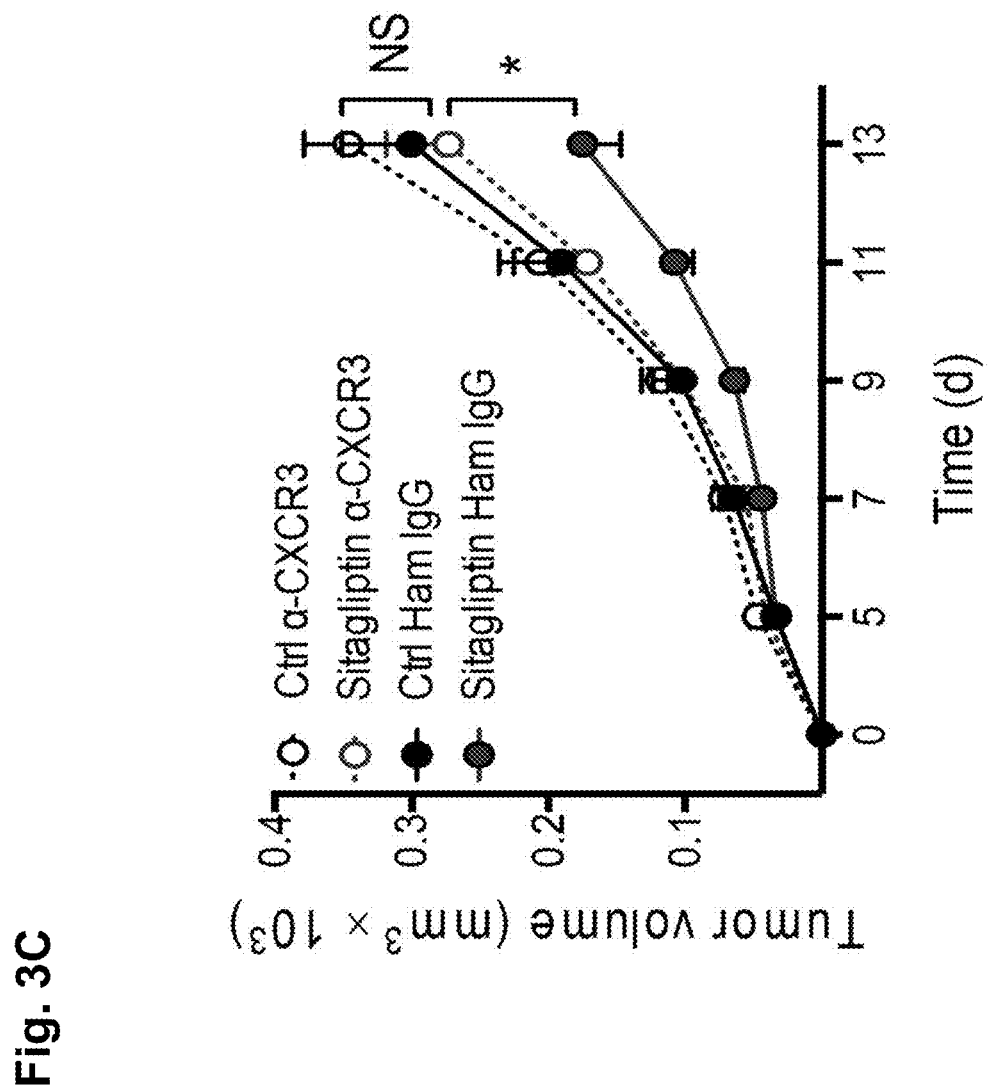
Figure 11:
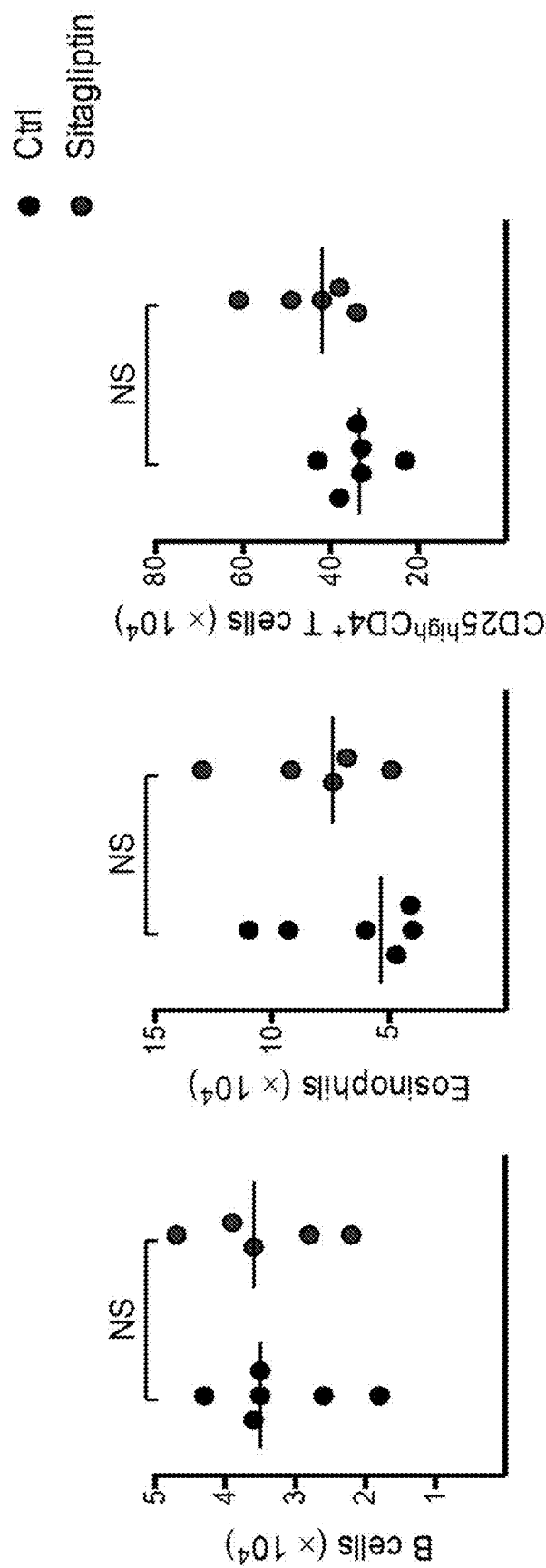
FIG. 11. DPP4 inhibition does not induce recruitment of B cells, eosinophils or regulatory T cells into CT26 tumors. BALB/c WT mice fed with ctrl or sitagliptin chow were subcutaneously injected with CT26 cells. Tumors were dissociated on day 11, and the number of infiltrating leukocytes was analyzed. Significance was determined via Mann-Whitney test. Data are representative of 2 independent experiments.

Our observations using the melanoma model, prompted us to study whether DPP4-mediated anti-tumor immunity could be extended to other tumor models. We therefore employed the CT26 colon carcinoma cell line, which can be used to initiate subcutaneous tumors in Balb/c mice. DPP4 inhibition resulted in a marked delay of CT26 tumor growth (FIG. 3a), which correlated with an enhanced infiltration of lymphocytes, including T cell subsets and NK cells (FIG. 3b). Of note, the number of tumor associated B cells, eosinophils and CD25$^{hi}$ regulatory T cells did not change upon sitagliptin treatment (FIG. 11). Blocking CXCR3 receptor signaling resulted in the loss of protection achieved with DPP4 inhibition (FIG. 3c). Our results thus far indicated that DPP4 acts to negatively regulate CXCR3-mediated anti-tumor immunity, effectively limiting lymphocyte infiltration into the tumor parenchyma.

Example 12. CXCL10 Degradation Limits CXCR3$^+$ Lymphocyte Migration

Figure 4A:
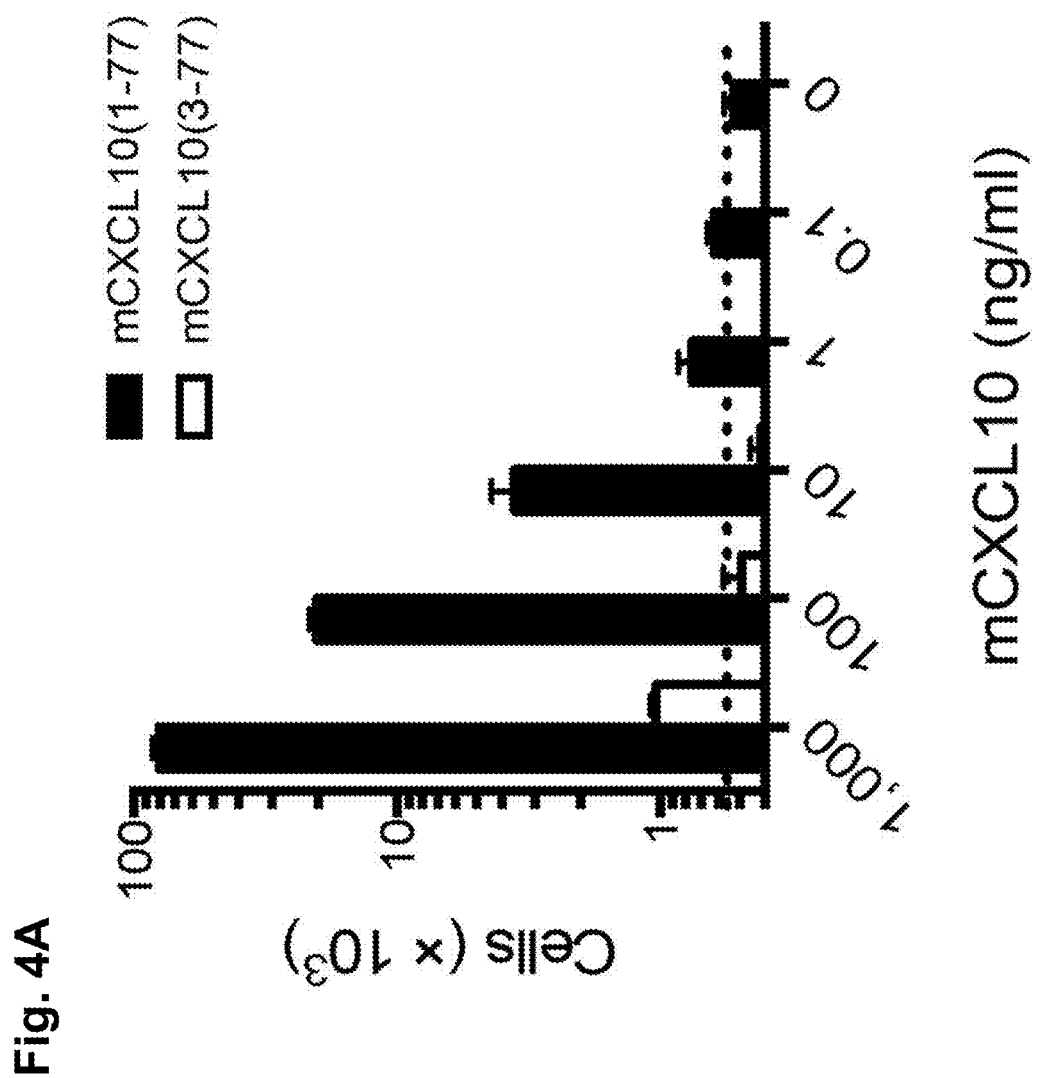
FIG. 4a-d. DPP4 mediates in vivo truncation of CXCL10. (a) Enumeration of CD8$^+$T cells migrating throw a transwell plate in which the indicated concentrations of mCXCL10 (1-77) (intact) or mCXCL10(3-77) (cleaved) were added. The dotted line indicates spontaneous migration (0 ng/ml) (Mean±SEM; n=4 experimental replicates). (b) Surface CXCR3 expression on CD8$^+$ T cells after incubation with the indicated amounts of chemokines. Representative histograms are shown for the 0-1000 ng/ml dose of mCXCL10 as indicated. Bars represent mean±SEM, n=4 experimental replicates. (c, d) WT mice fed with control or sitagliptin chow were injected intravenously with 5 μg of CpG-A and blood samples were collected at the indicated time points. Quantification of total mCXCL10 (c) and mCXCL10(1-77) (d) was determined by ELISA (* P<0.01). Each circle represents a single mouse. Significance was determined using 2Way Anova. Data are representative of 3 (a, b); or 2 (c, d) independent experiments.
Figure 4B:
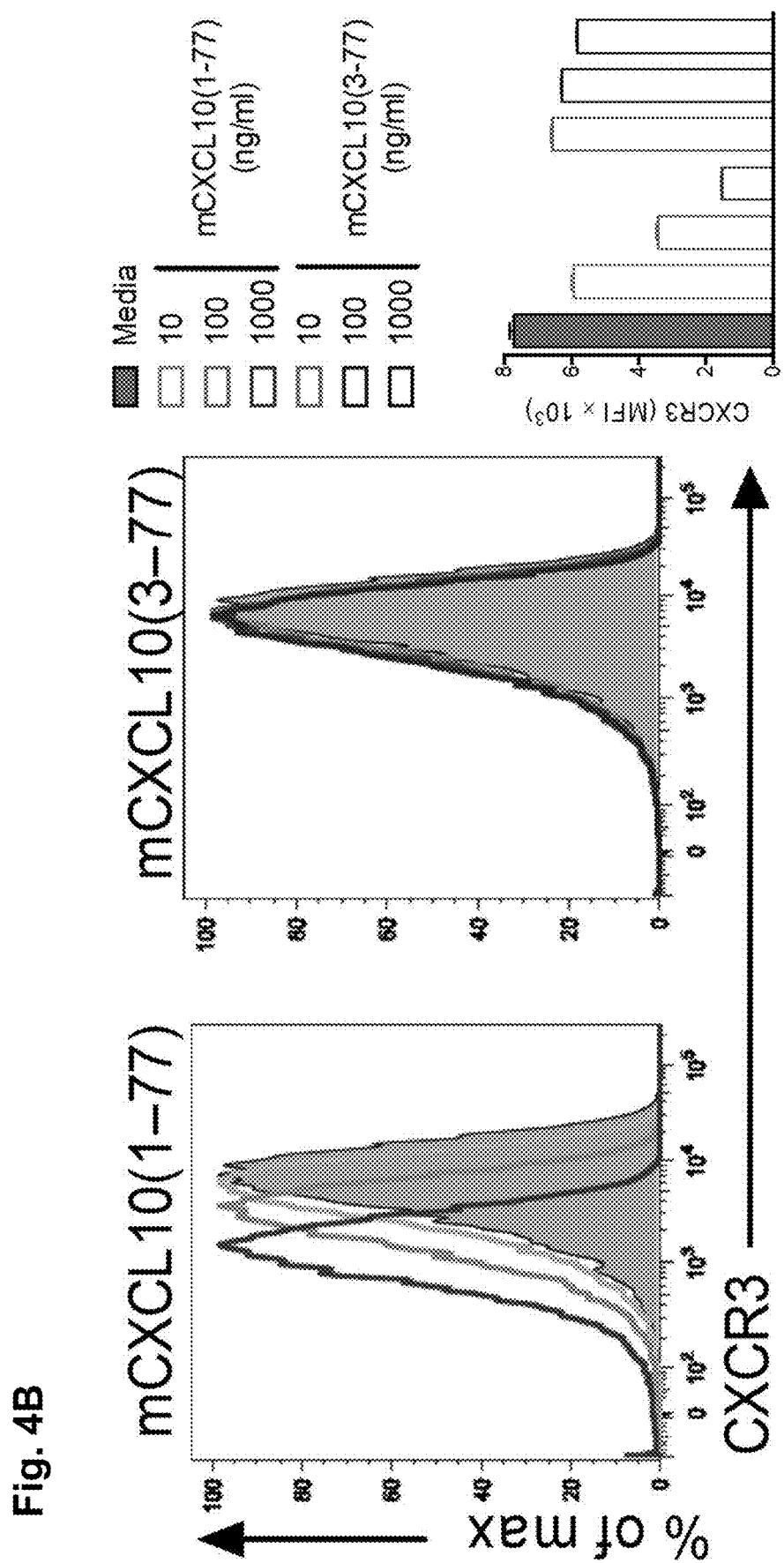

Most biochemical and functional studies of chemokine processing have employed human proteins. Indeed, only a few mouse chemokines have been reported to be DPP4 substrates[20,21]. As indicated above, we directly tested the ability of DPP4 to truncate an extended panel of chemokines (FIG. 2b, FIG. 9b,c). We further assessed the consequences of DPP4 post-translational modification on mCXCL10-induced lymphocyte trafficking. We examined the ability of full length and DPP4-truncated CXCL10 (referred to herein as mCXCL10(1-77) and mCXCL10(3-77), respectively) to promote lymphocyte migration in an in vitro transwell system. Consistent with human studies[4], DPP4-truncated mCXCL10(3-77) did not induce murine T cell migration (FIG. 4a), nor did it trigger CXCR3 internalization (FIG. 4b).

Figure 4C:
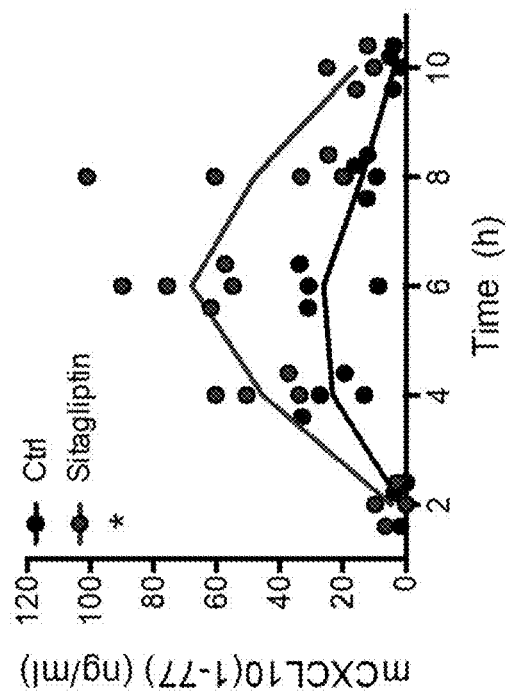
Figure 4D:
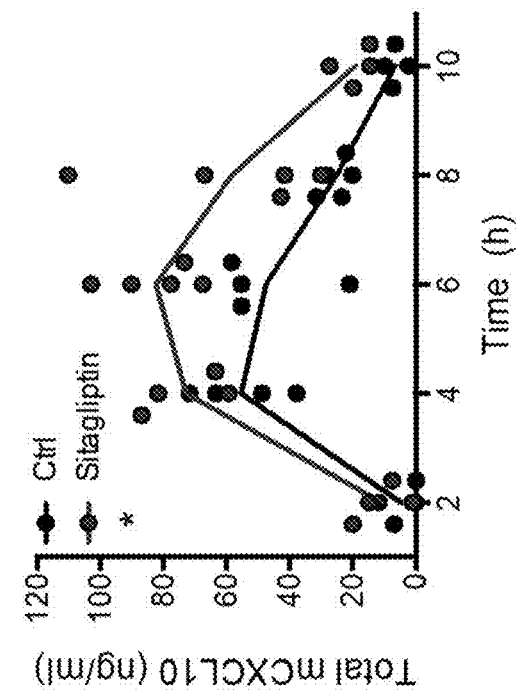
Figure 12C:
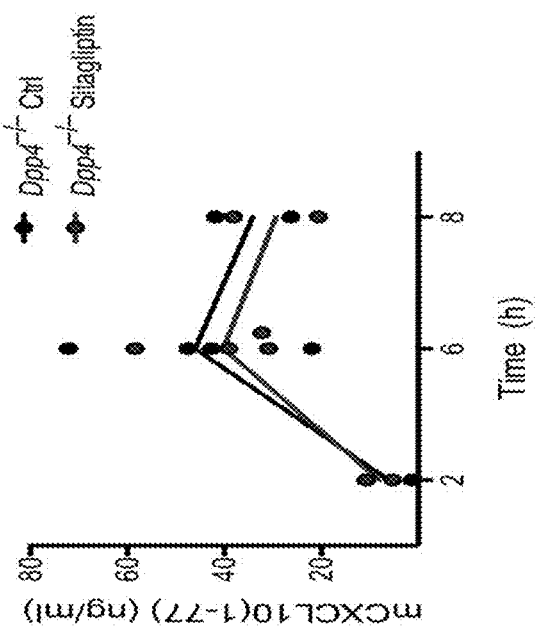
FIG. 12a-d. DPP4 expression modulates chemokine expression in vivo. WT (a,d) or Dpp4–/– (c) mice fed with sitagliptin or ctrl chow were injected intravenously with 5 µg of CpG-A. Graph represents percentage of mCXCL10(1-77) among total mCXCL10 determined in plasma samples at the indicated time points (6 h after CpG injection in b). (c) Dpp4–/– mice fed with ctrl or sitagliptin chow were treated as described in a. Quantification of mCXCL10(1-77) in plasma samples is shown. (d) Expression of mCCL2, mCCL3 and mCCL22 was determined in WT mice treated as described in a. Each circle on the graphs represents a single mouse. Significance was determined using the Mann-Whitney test (*P<0.05). Data are representative of 2 independent experiments.
Figure 12B:
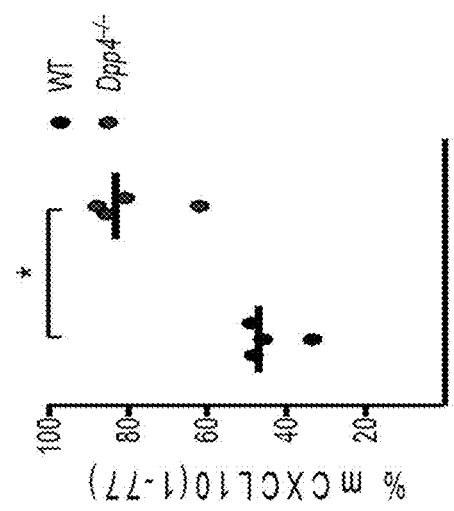
Figure 12A:
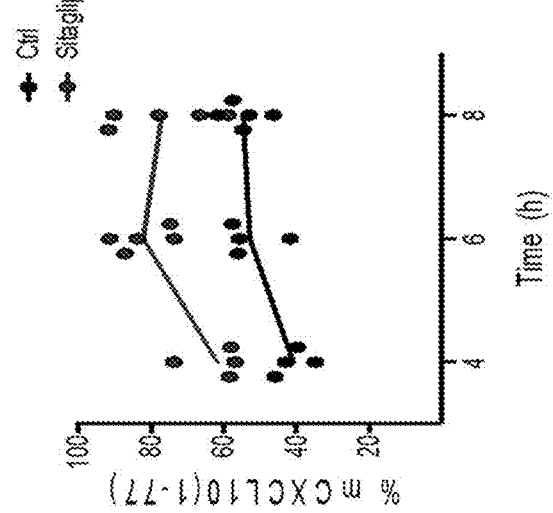
Figure 12D:
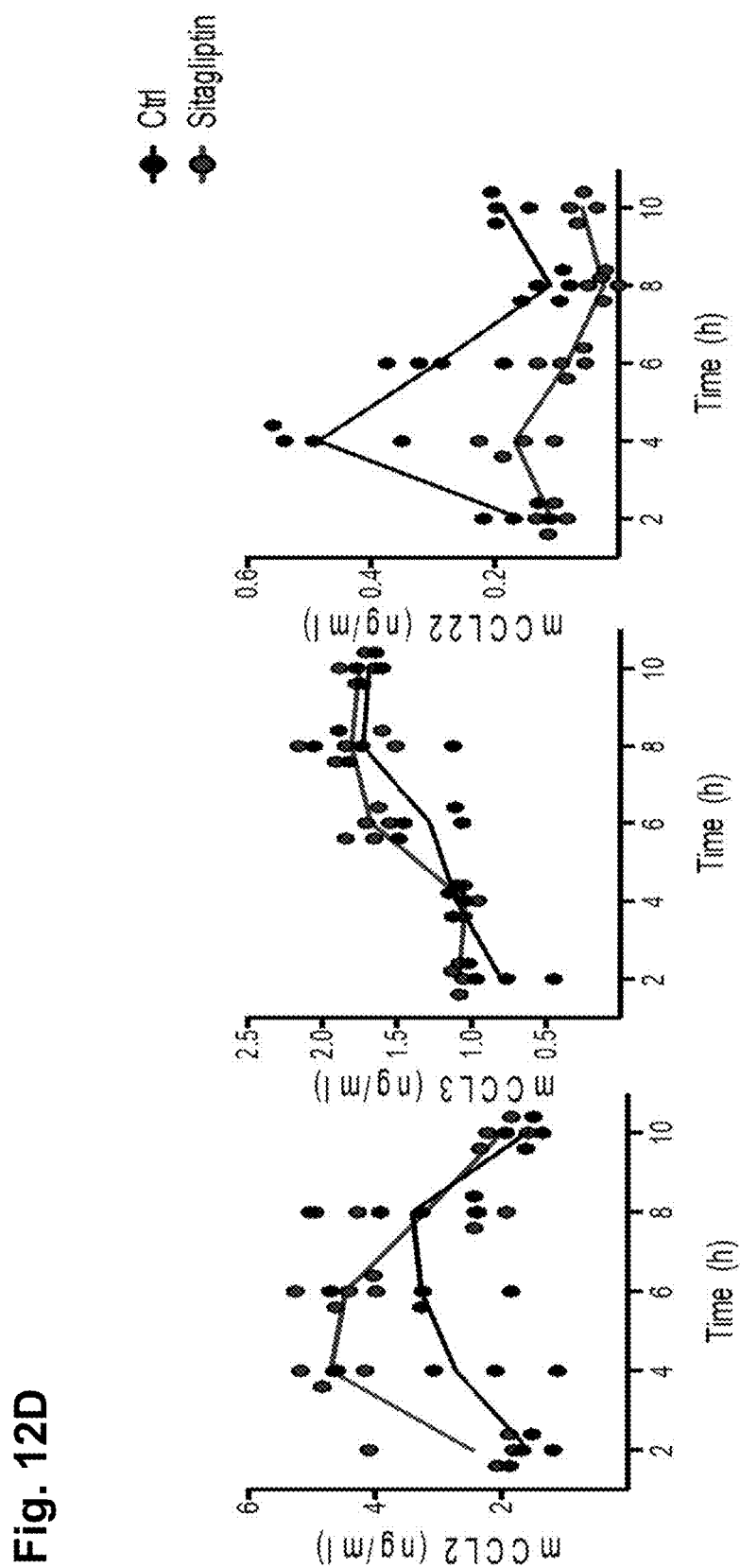

To study whether DPP4 mediates truncation of CXCL10 in vivo, we induced endogenous CXCL10 production by intravenous injection of the Toll-like receptor 9 (TLR9) agonist CpG-A. DPP4 inhibition resulted in stabilization of CpG-A-induced plasma CXCL10 (referred to as total CXCL10 and detected by conventional assays that measure both intact and N-terminally truncated CXCL10), as compared with control WT mice (FIG. 4c). To quantify bioactive CXCL10, we established an immunoassay specific for the intact form of mCXCL10 (i.e., mCXCL10(1-77), possessing the isoleucine-proline as its N-terminal residues). The quantity of mCXCL10(1-77) was significantly higher when DPP4 was inhibited (FIG. 4d and FIG. 12a). Similar results were observed in CpG-A treated Dpp4$^{-/-}$ mice (FIG. 12b). As an additional control, we demonstrated that sitagliptin treatment of Dpp4$^{-/-}$ mice did not have an additive effect, again excluding off-target activity of the drug (FIG. 12c). Of interest, intravenous CpG-A injection also induced expression of mCCL2, mCCL22 and mCCL3. Although the concentrations of mCCL3 were not significantly different between the groups, the quantity of plasma mCCL2 was higher in sitagliptin treated mice (FIG. 12d), a result that correlates with high sensitivity of mCCL2 to DPP4 truncation (FIG. 9c). DPP4 inhibition also modulated the plasma concentration of mCCL22, yet in this instance there was a significant decrease in its expression (FIG. 12d). Indeed, DPP4-mediated N-terminal truncation of mCCL22 renders the chemokine unable to be scavenged by the atypical chemokine receptor D62, helping to interpret this result. These data support DPP4 mediated cleavage as an in vivo mechanism of regulating multiple chemokines with direct evidence for the preservation of the bioactive form of CXCL10 (among others).

Figure 5B:
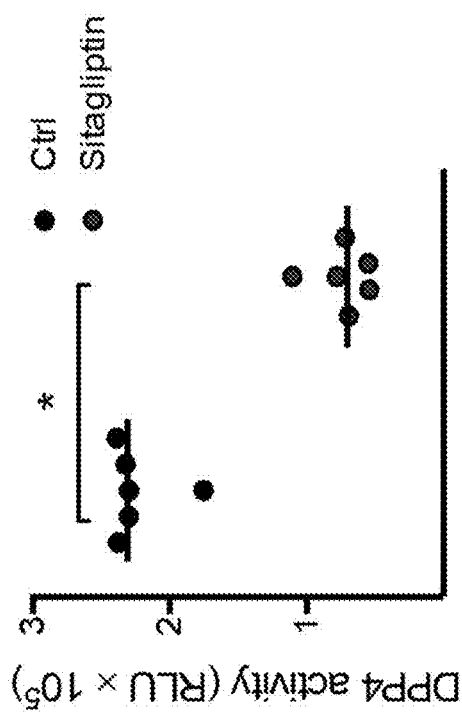
Figure 5A:
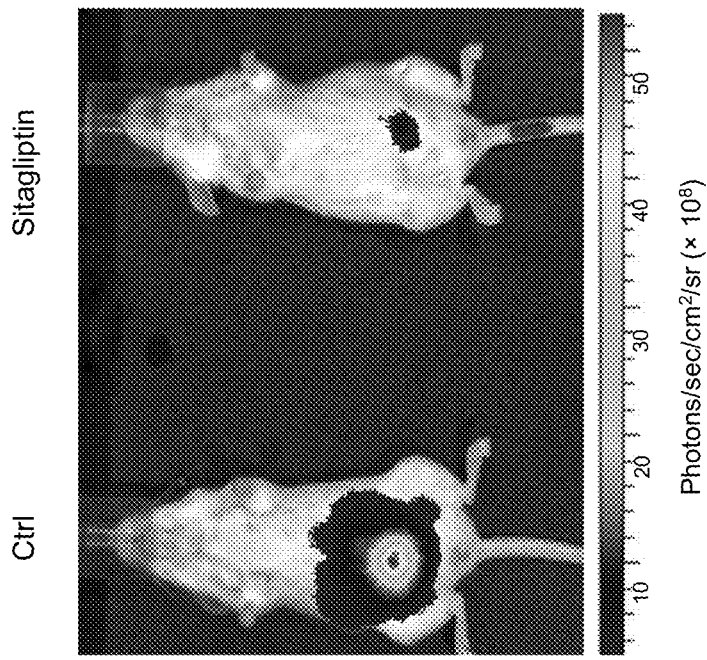
Figure 5D:
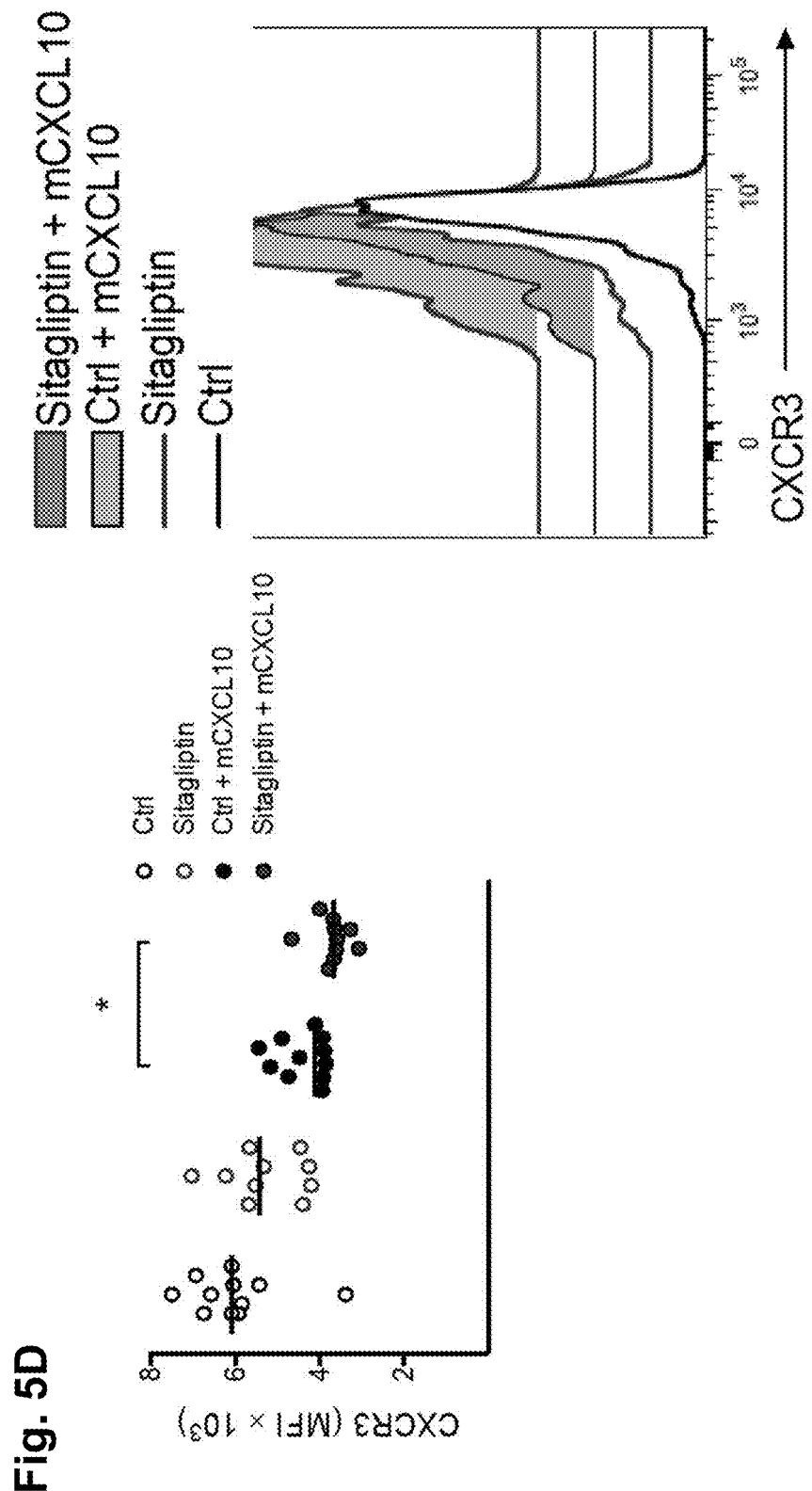
Figure 13A:
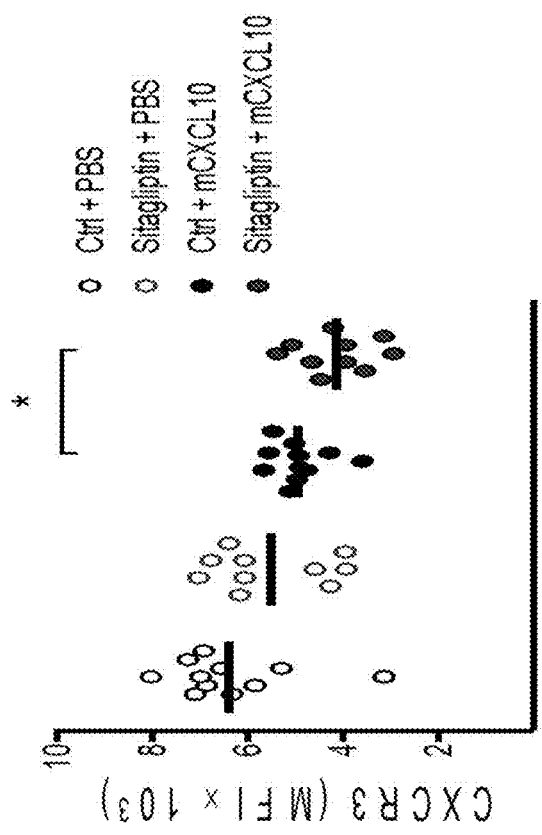
FIG. 13a-e. DPP4 inhibition induces CXCL10-mediated leukocyte trafficking in vivo. WT mice fed with sitagliptin or ctrl chow were injected intraperitoneally with mCXCL10 or PBS (a-c, e). Cellular contents in the peritoneal cavity were analyzed 12-14 h after injection. The number (a) and CXCR3 MFI (b) on CXCR3-expressing CD4+ T cells were analyzed (*P<0.05). (c) CXCR3 MFI of peripheral blood CXCR3+CD8+ T cells. (d) WT and Dpp4–/– mice were treated as described in a. The number of leukocytes in the peritoneal cavity was evaluated 6 h after mCXCL10 injection (*P<0.05, **P<0.01). (e) WT mice were treated as described in a, and the number of eosinophils and neutrophils in the peritoneal cavity was evaluated. Each circle represents one mouse; data were combined from 2 independent experiments. P values were generated via Mann-Whitney test; data are from 1 experiment (c) or are pooled from 2 (a,b,e) or 3 (d) independent experiments.
Figure 13B:
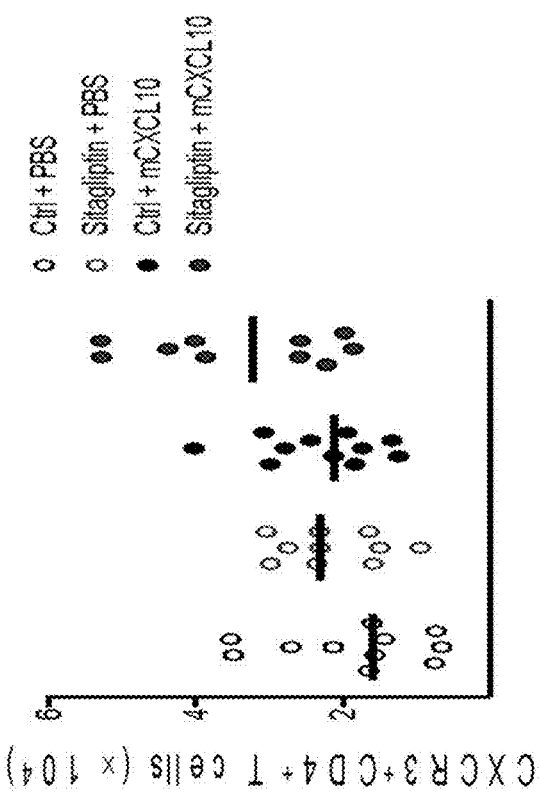
Figure 13C:
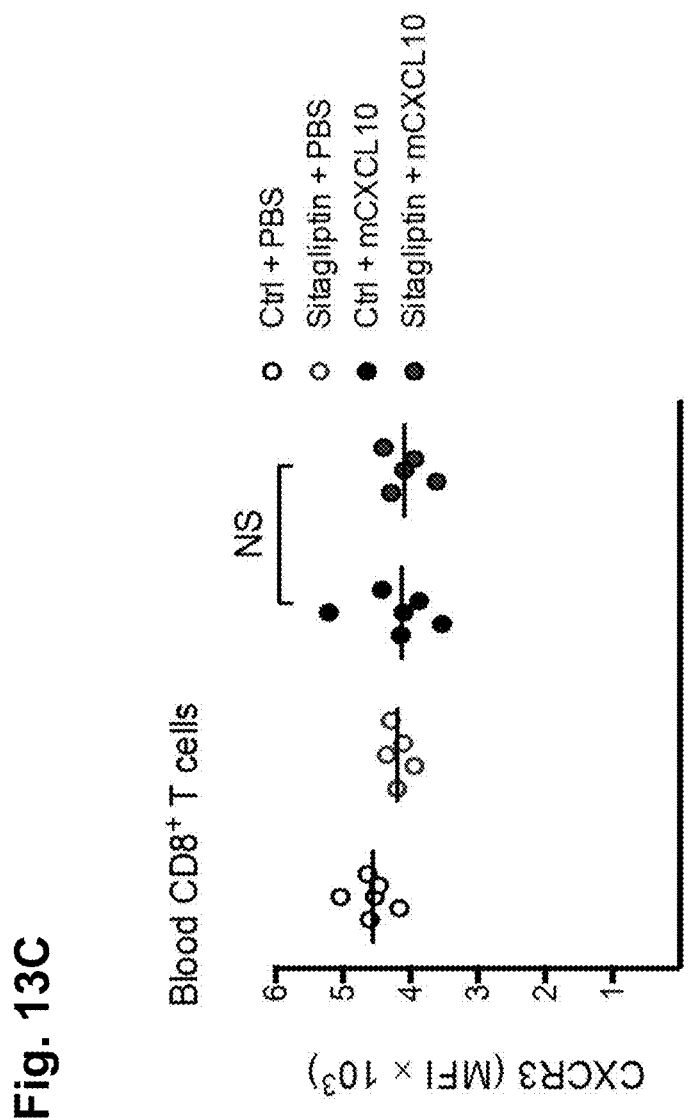
Figure 13D:
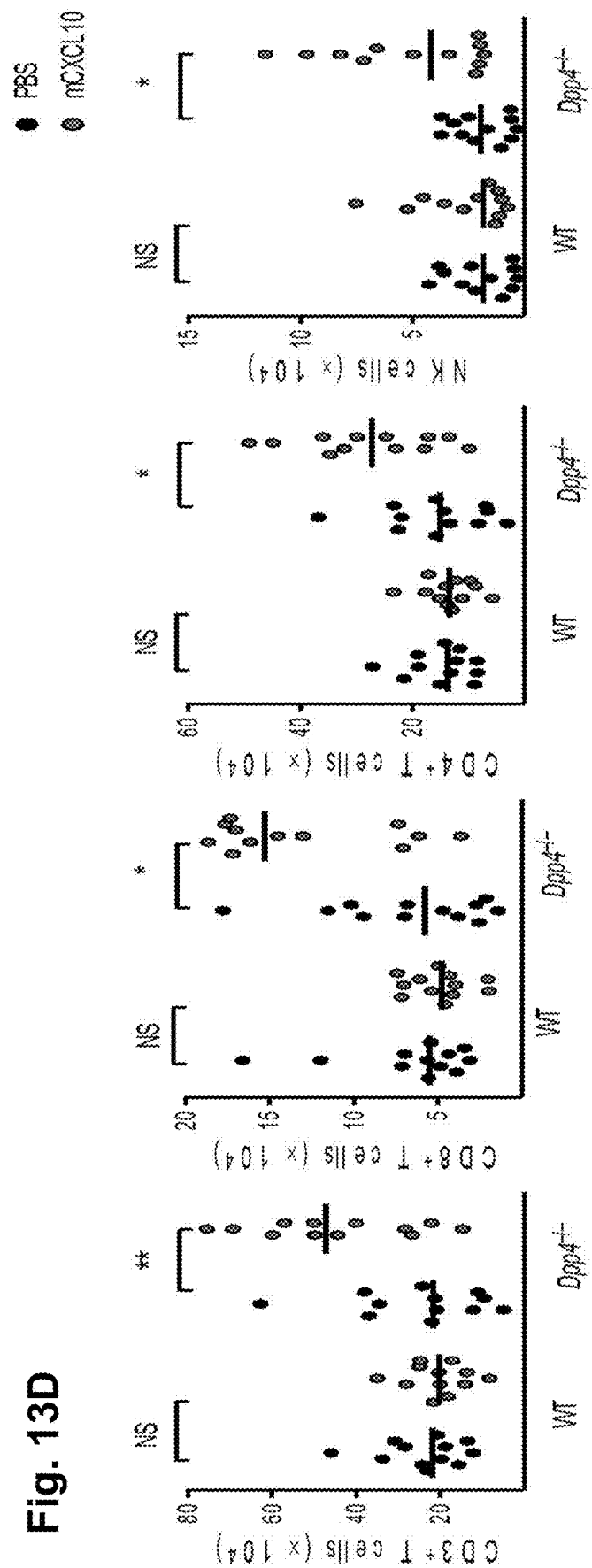
Figure 13E:
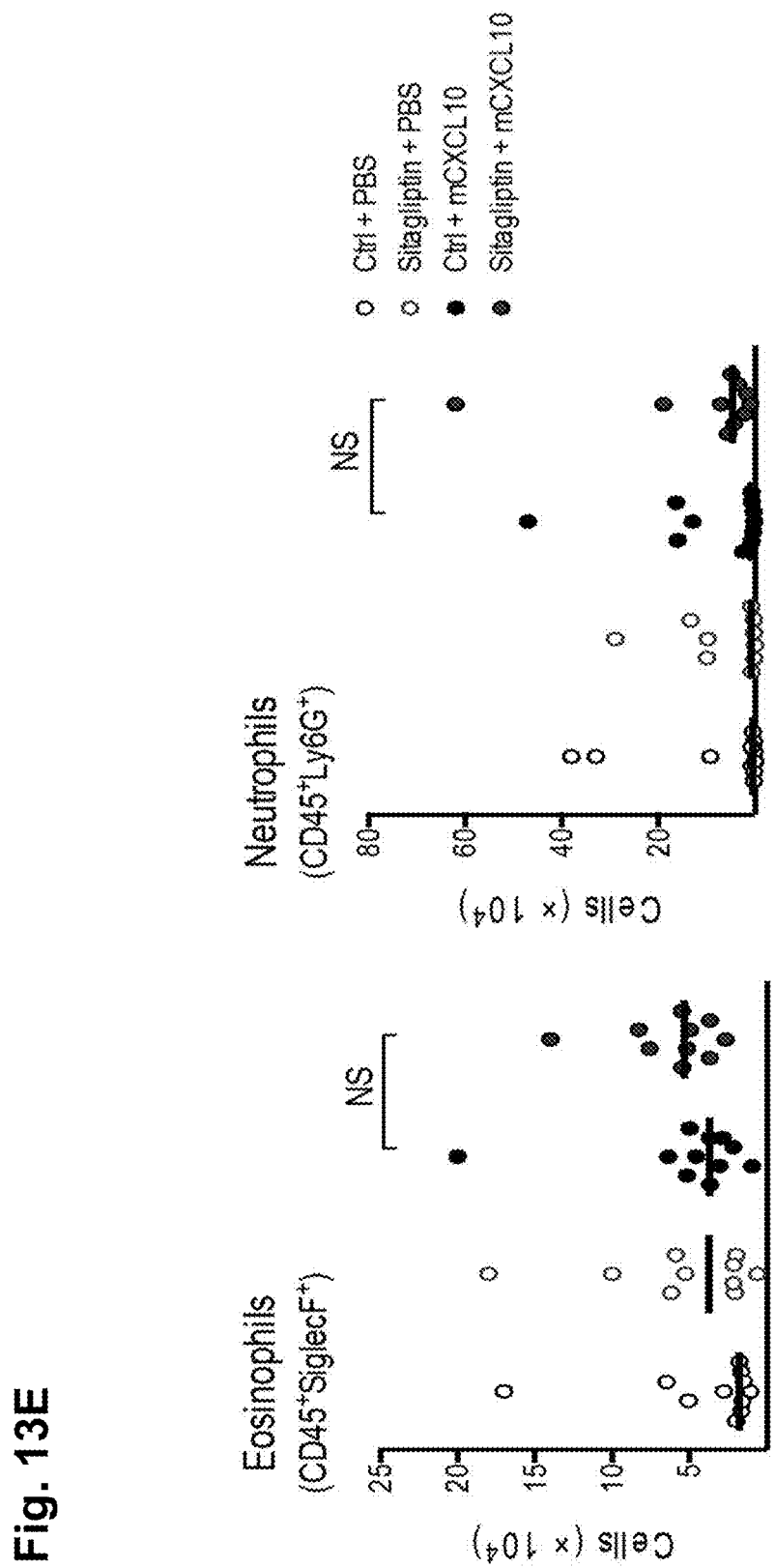

To directly test the role of DPP4 on CXCL10-mediated immune cell trafficking, we next injected recombinant mCXCL10 into the peritoneal cavity of wild-type mice fed with control or sitagliptin chow as a strategy to study chemokine-mediated migration of leukocytes. The peritoneal cavity of mice showed high DPP4 activity, which could be significantly inhibited by sitagliptin treatment (FIG. 5a,b). Notably, mCXCL10 injection failed to induce significant infiltration of CXCR3-expressing T cells in control mice, suggesting rapid catabolism of the administered chemokine (FIG. 5c and FIG. 13a). By contrast, inhibition of DPP4 enhanced mCXCL10-mediated infiltration of T cells (FIG. 5c and FIG. 13a). Additionally, we observed that the CXCR3 plasma membrane expression on migrating T cells was lower in sitagliptin treated mice (FIG. 5d, p=0.002, and FIG. 13b). We interpret this to be a result of DPP4 inhibition enhancing in vivo CXCL10-mediated CXCR3 internalization. This observation was seen locally, at the site of mCXCL10 injection, but not systemically as indicated by the unaltered CXCR3 expression on peripheral blood T cells (FIG. 13c). These findings were replicated in Dpp4$^{-/-}$ mice, which showed higher lymphocyte migration following intraperitoneal injection of mCXCL10, as compared to WT animals (FIG. 13d). As CXCL10 has also been proposed to act as an antagonist of CCR3-mediated leukocyte migration, we analyzed the recruitment of CCR3-expressing eosinophils. Injection of mCXCL10 in control or sitagliptin-fed mice did not show differential recruitment of polymorphonuclear cells into the peritoneal cavity (FIG. 13e).

Figure 14A:
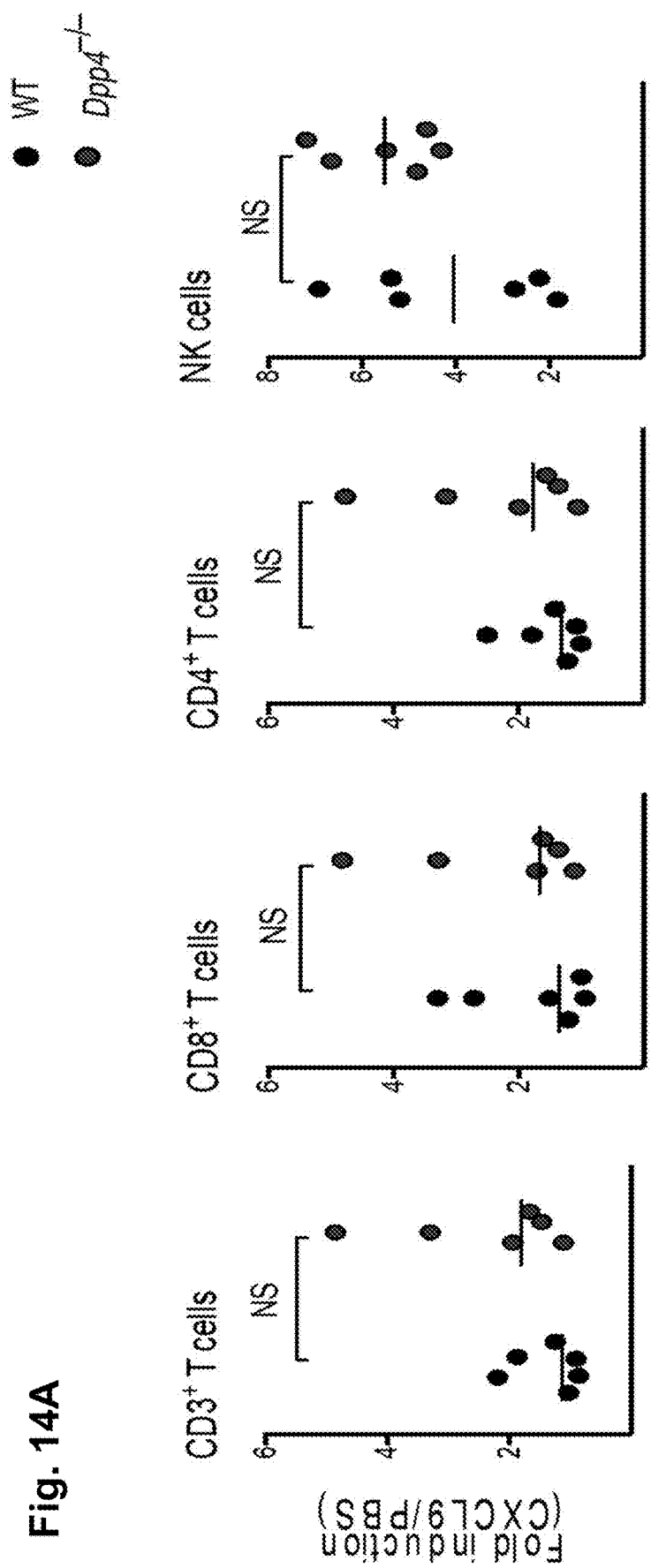
FIG. 14a-b. DPP4 regulates the chemotactic activity of DPP4-sensitive chemokines in vivo. WT and Dpp4−/− mice were injected via the intraperitoneal (IP) route with PBS, (a) 1 μg of mCXCL9 or (b) 1 μg of mCCL5. IP washes were collected 6 h after injection, and the number of leukocyte populations was analyzed. Fold induction of chemokine-mediated over PBS-mediated leukocyte trafficking was calculated. *P<0.05, **P<0.005. Each circle represents a single mouse. P values from Mann-Whitney test. Data are combined from 2 independent experiments.
Figure 14B:
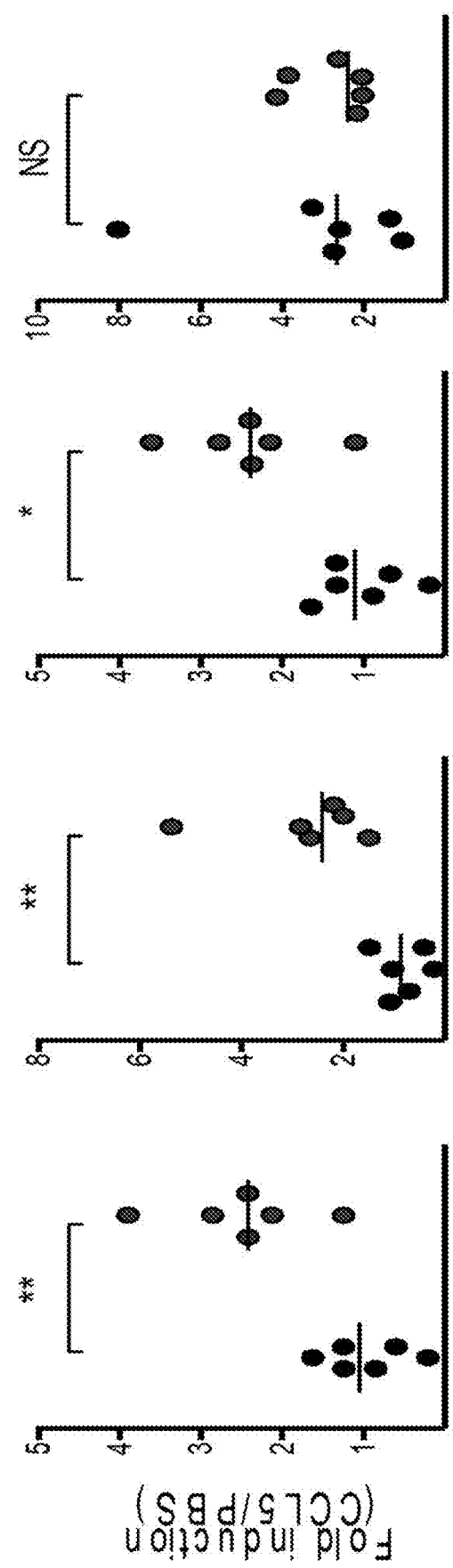
Figure 15A:
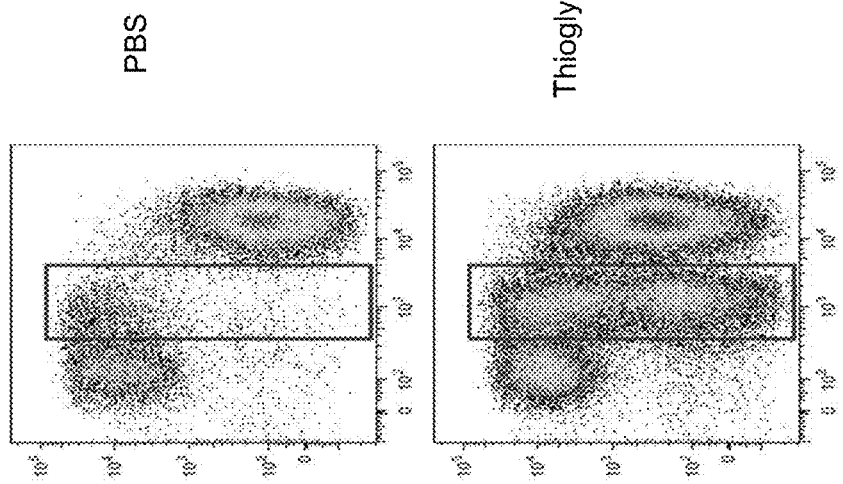
FIG. 15a-c. DPP4 inhibition does not affect thioglycollate-mediated peritonitis.
Figure 15A:
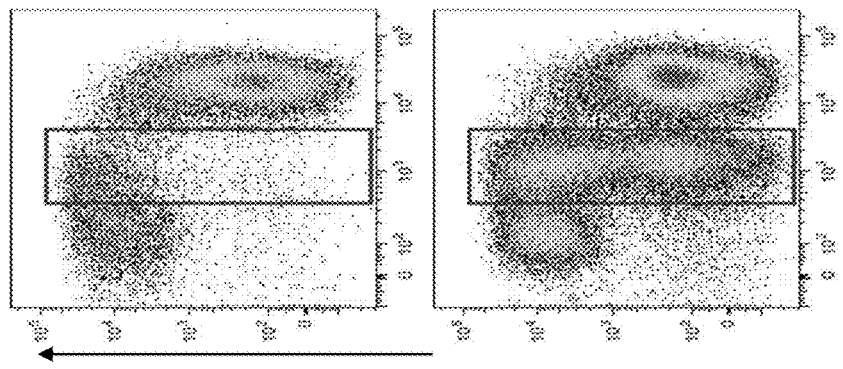
Figure 15A:
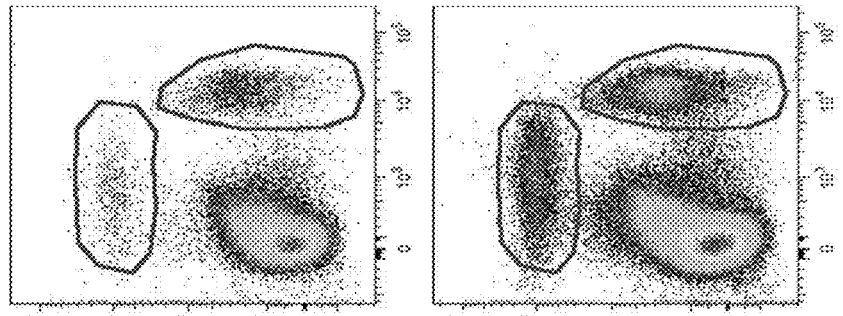
Figure 15A:
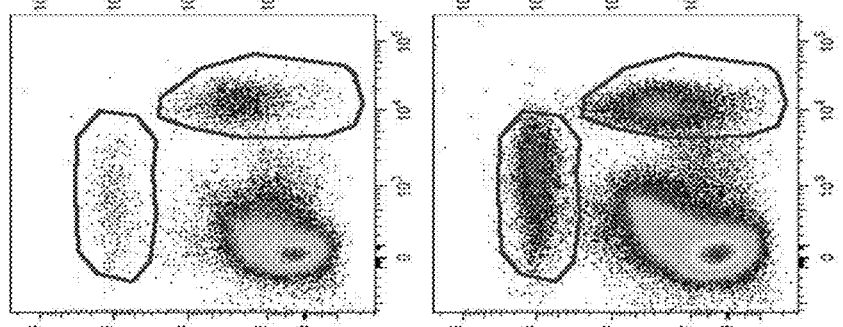
Figure 15B:
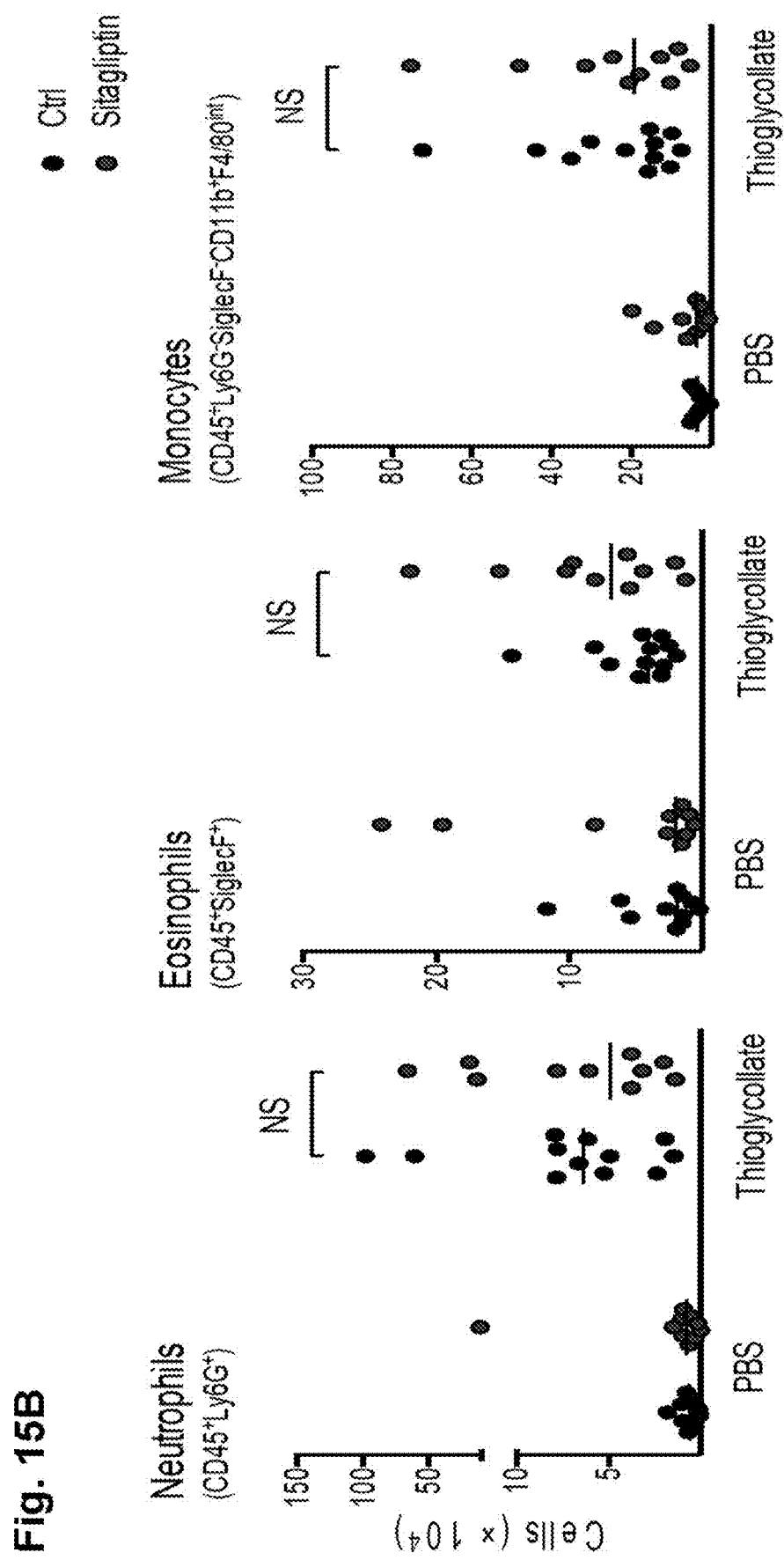
Figure 15C:
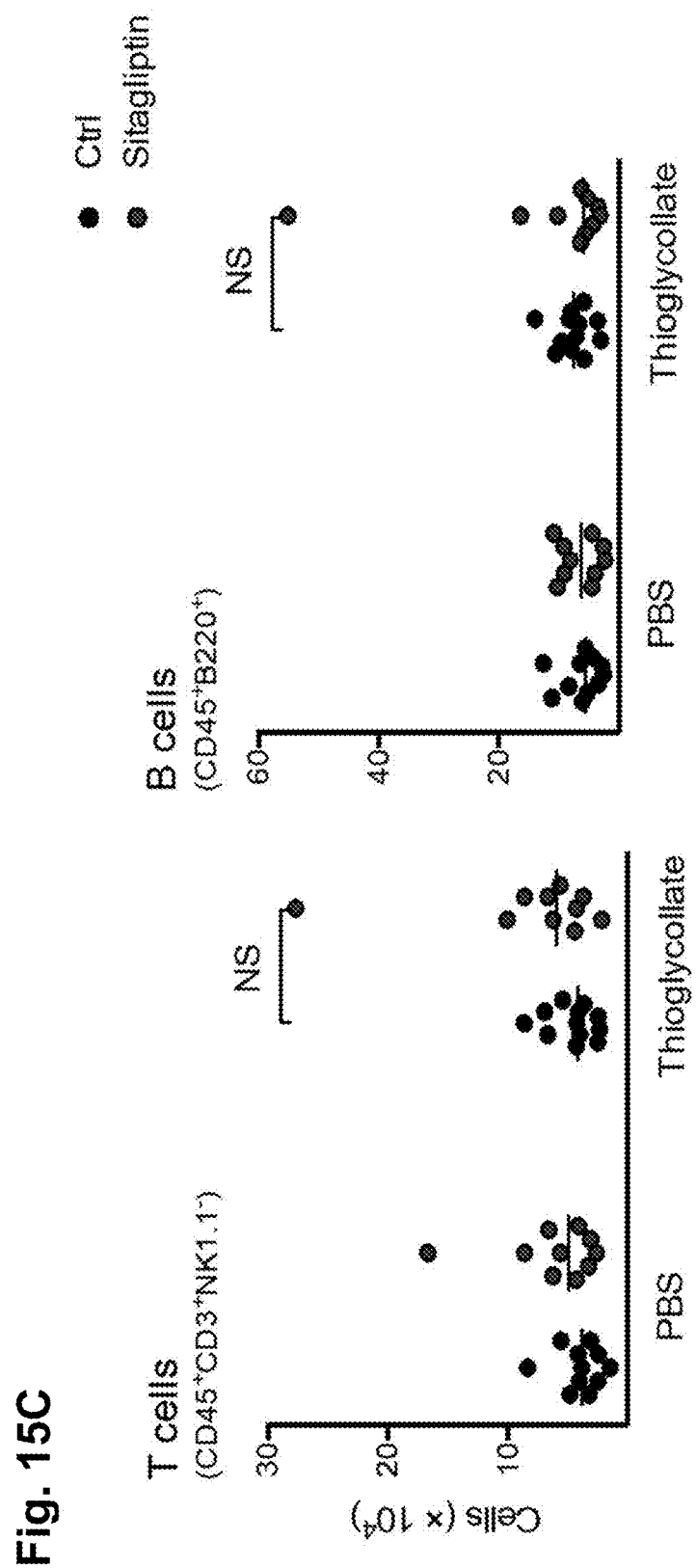

In parallel with studies using recombinant mCXCL10, we also evaluated the intraperitoneal injection of mCXCL9 (insensitive to DPP4-mediated truncation); and mCCL5 (sensitive to $NH_2$-truncation). For mCXCL9, we observed migration of NK cells into the peritoneal cavity, but consistent with it lacking the DPP4 consensus motif, no increase in lymphocyte migration was observed in Dpp4$^{-/-}$ animals (FIG. 14a). Similar to the observations made using mCXCL10, intraperitoneal injection of mCCL5 induced enhanced lymphocyte migration in Dpp4$^{-/-}$ animals (FIG. 14b). We also evaluated the impact of DPP4 inhibition on intraperitoneal thioglycollate-induced inflammation and leucocyte migration. In this model, DPP4 inhibition did not significantly alter the magnitude of leucocyte migration. Thioglycollate stimulated the recruitment of neutrophil, monocyte and eosinophil migration, but no differences were observed in sitagliptin treated animals (FIG. 15a, b). Importantly, thioglycollate does not induced lymphocyte trafficking (FIG. 15c), likely accounting for the lack of a DPP4 phenotype. Together, these data establish DPP4 as an in vivo regulator of chemokine-mediated lymphocyte trafficking.

Figure 5E:
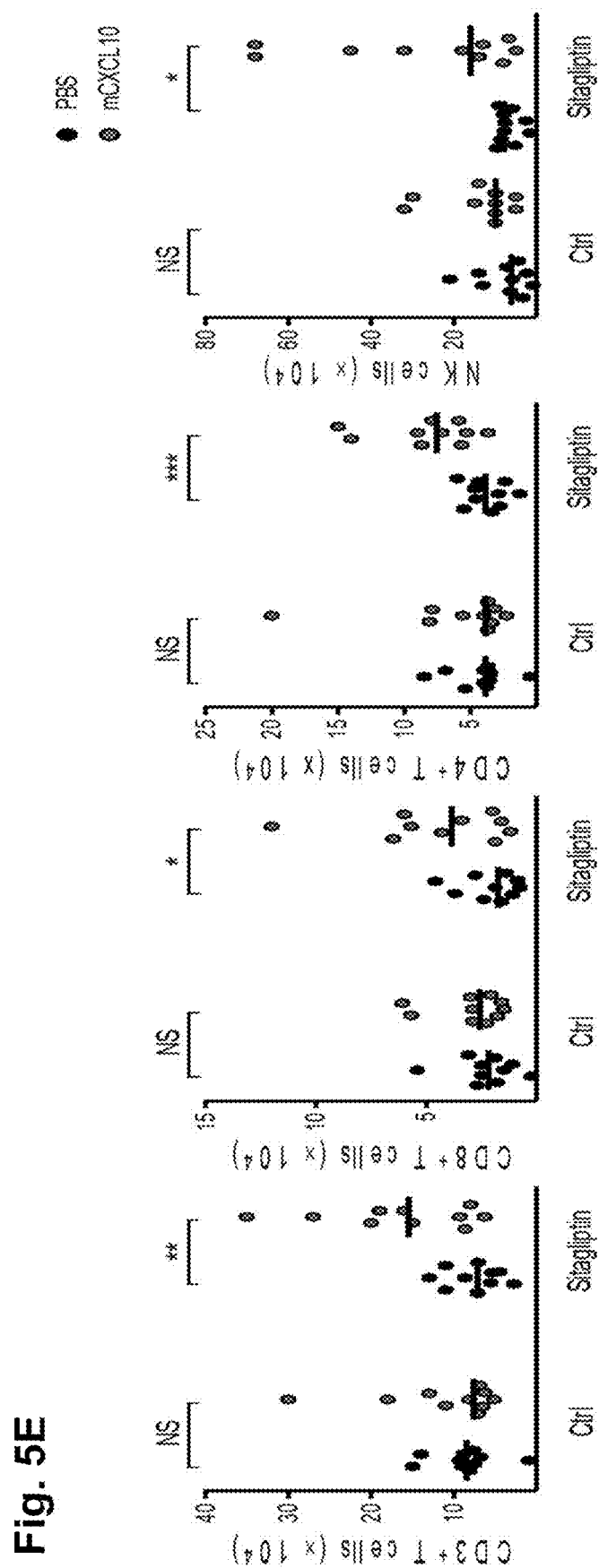

To extend these results to the migration of lymphocytes into the tumor microenvironment, we tested whether mCXCL10 injection was also able to enhance leukocyte trafficking into the tumor parenchyma. Specifically, we performed intratumoral injection of mCXCL10 into day 7 melanoma tumors, growing in mice fed with control or sitagliptin chow. Of note, day 7 tumors were selected as DPP4 inhibition has not yet established differential trafficking by this time point (as seen when comparing PBS treated control mice vs. PBS treated sitagliptin fed mice, p=n.s., FIG. 5e). When mCXCL10 was injected into control mice, no increase in lymphocyte migration could be observed (FIG. 5e). This was consistent with the high degree of intra-tumoral expression of DPP4 (FIG. 1a). Sitagliptin treatment resulted in enhanced CXCL10 recruitment of T cells and NK cells into the tumor parenchyma (FIG. 5e), whereas trafficking of B cells, regulatory T cells, eosinophils or neutrophils were unchanged (FIG. 16).

Figure 5F:
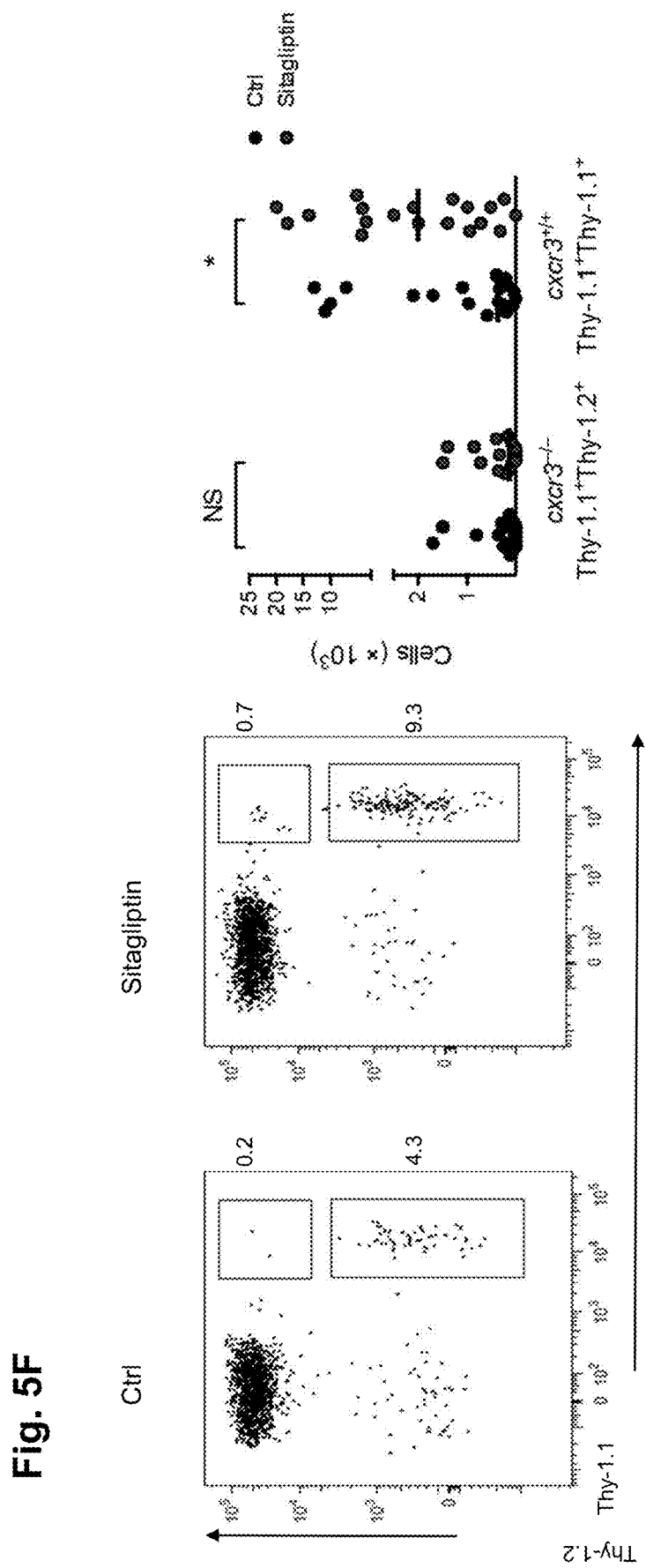

To test a role for CXCR3 expression, we performed adoptive cell transfer of gp100 tumor antigen-specific CD8$^+$T cells (referred to as Pmel-1). Congenic markers were used to track transferred cells. CXCR3 sufficient (Thy1.1$^{+/+}$ Pmel-1) or deficient (Thy1.1$^+$Thy1.2$^+$ Cxcr3$^{-/-}$ Pmel-1) T cells were mixed at a ratio of 1:1 and transferred into wild-type Thy1.2 B16F10 tumor-bearing animals. T cell trafficking was evaluated 12-14 hr after mCXCL10 injection into the tumor. CXCL10-mediated trafficking of Pmel-1 cells into the B16F10 tumors was enhanced by DPP4 inhibition, and showed complete dependence on CXCR3 expression (FIG. 5f). Together these data establish that DPP4 inhibition results in the protection of bioactive CXCL10 and enhanced migration of CXCR3-expressing T cells into sites of inflammation and into the parenchyma of growing tumors.

Example 13. DPP4 Inhibition Improves Response to Immunotherapy

Figure 6D:
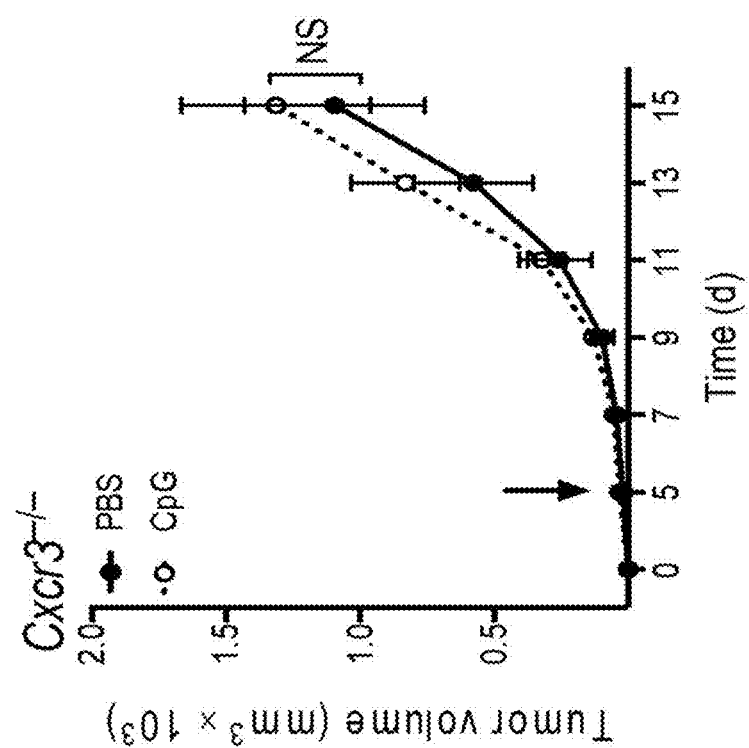
Figure 6C:
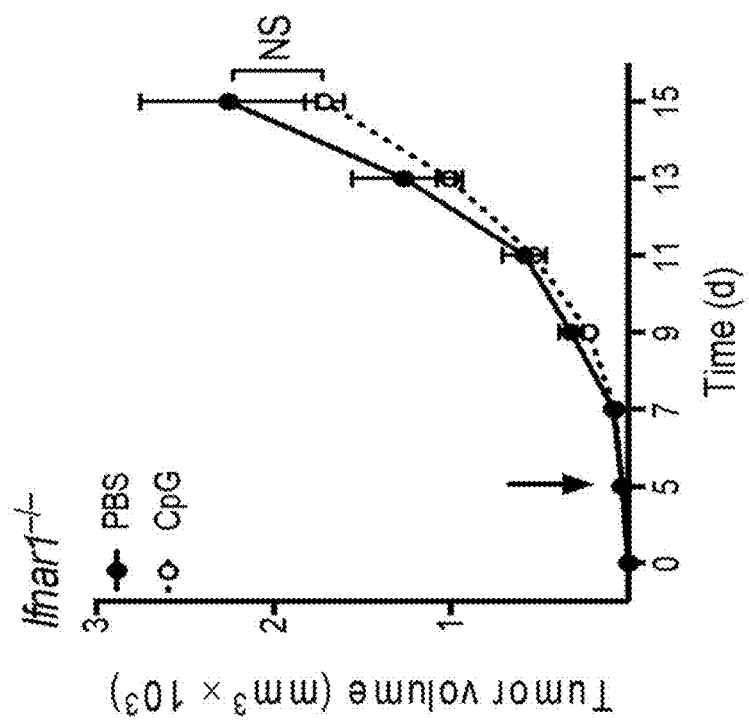
Figure 6E:
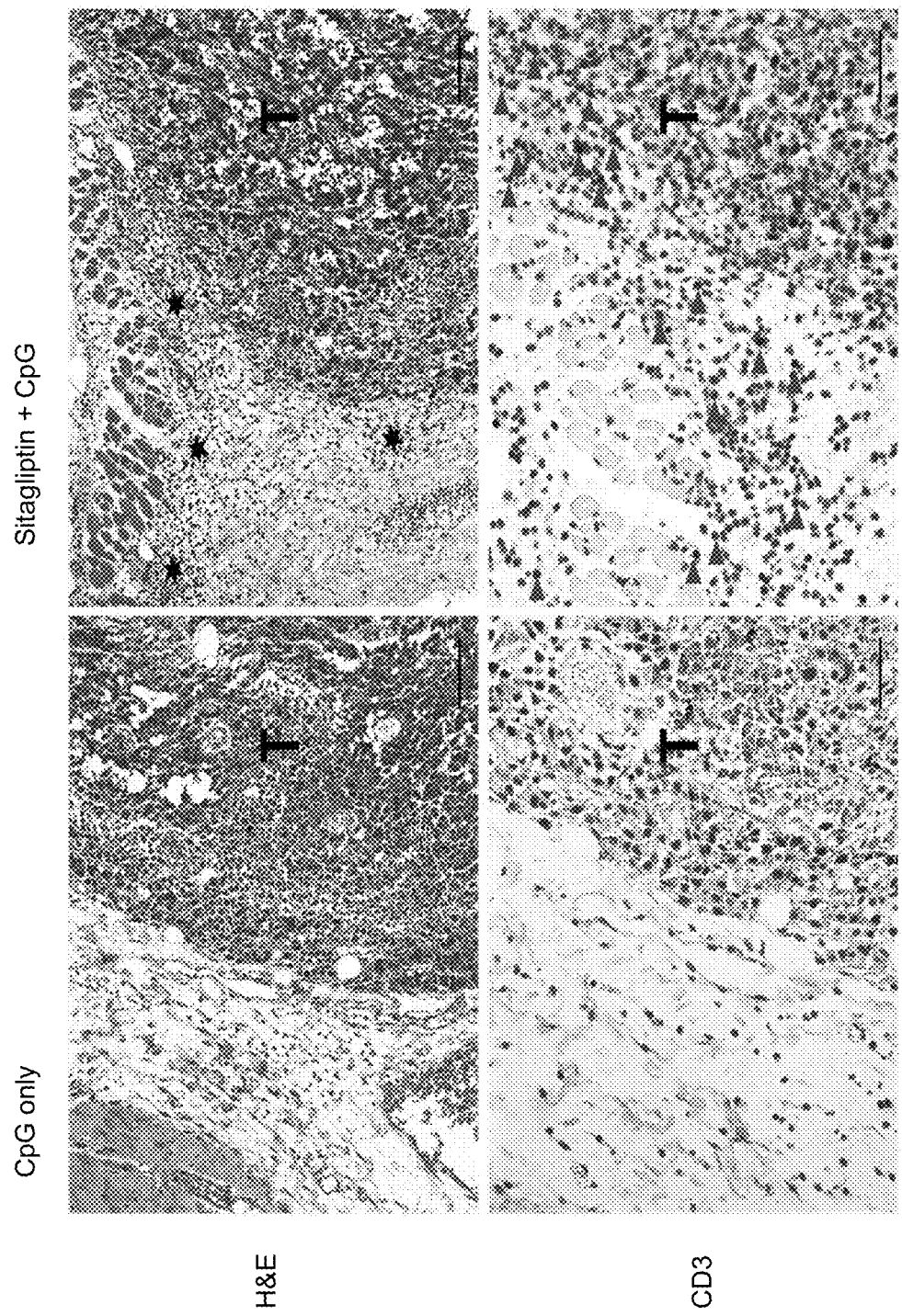

Following from the defined mechanism of action of sitagliptin monotherapy, we predicted that enhanced lymphocyte trafficking could be combined with other immunotherapeutic strategies, especially those that generate high quantities of CXCL10 or that depend on CXCR3-expressing effector T cells. As a first test of our hypothesis, we evaluated the combination of adjuvant therapy and sitagliptin treatment. We selected CpG ODN as it has been used in human trials and is known to induce high amounts of endogenous CXCL10[24,25]. As shown above, bioactive plasma mCXCL10 produced upon CpG treatment is protected by DPP4 inhibition (FIG. 4c,d). Similarly, CpG induced high amounts of intra-tumoral CXCL10 (median concentration ~300 ng/g of tumor homogenate), and sitagliptin administration protected the full-length form of the molecule (FIG. 6a). CpG-A injection also elevated the intra-tumoral expression of mCCL2 and mCCL22, but no significant differences were seen between control and sitagliptin treated animals (data not shown). Supporting the role of CpG-A as a potent anti-tumor immune modulator, a single intra-tumoral injection was sufficient to induce a delay in B16F10 tumor growth, with an additive effect seen when mice were treated with sitagliptin (FIG. 6b). CpG-mediated tumor immunity was dependent on type I interferon receptor (IFNAR1) signaling and CXCR3 expression (FIG. 6c, d). Immunohistochemistry was employed to evaluate lymphocyte migration following CpG treatment, given alone or in combination with sitagliptin. Representative images are shown, taken from eight tumors per group. We observed modest CD3⁺ lymphocyte infiltration of the tumors in CpG only treated mice, and moreover the tumor capsule remained intact (FIG. 6e). By contrast, the addition of sitagliptin resulted in a striking increase in tumor inflammation and T cell recruitment (red arrows indicate infiltrating CD3⁺ cells, FIG. 6e). We also observed that the tumor capsule was disrupted in mice receiving the DPP4 inhibitor, likely a result of the enhanced inflammation. These data suggest that inhibition of DPP4 can be used to stabilize biologically active CXCL10, enhancing T cell migration into the tumor parenchyma as a strategy for enhancing adjuvant-based tumor immunity.

Figure 7A:
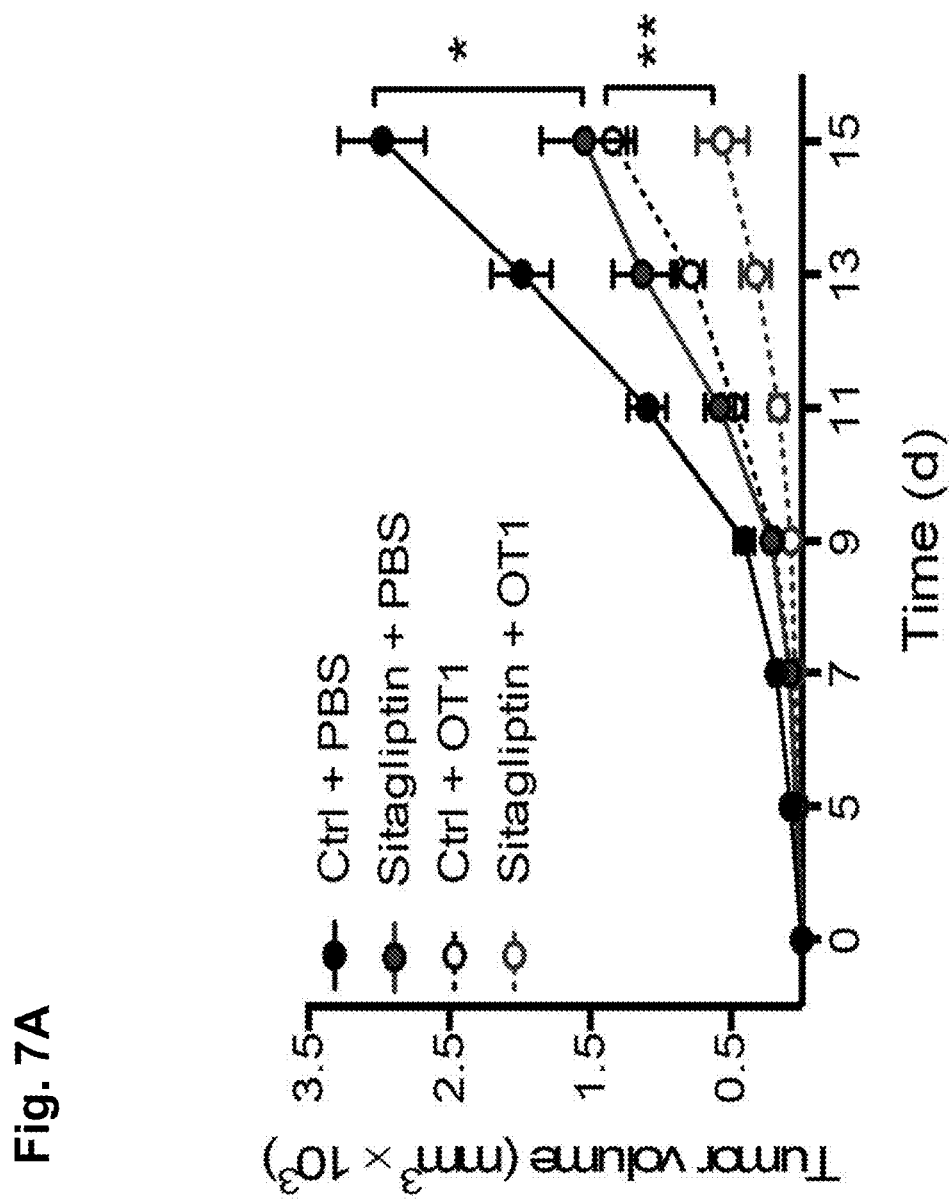
FIG. 7a-b. Combination therapy establishes DPP4 inhibition as a general mechanism to improve tumor immunity. (a) C57Bl/6 WT mice were fed with control or sitagliptin chow prior to subcutaneous injection of B16F10-OVA cells. On day 3 after tumor cell injection, mice received an adoptive transfer of OT1 CD8$^+$ T cells. Tumor volumes are shown (data represent mean±SEM, n=6 mice per group. * P<0.05, ** P<0.01) (b) Balb/c WT mice were fed with ctrl or sitagliptin chow prior to subcutaneous injection of CT26 cells. On day 3, 6 and 9 after tumor implantation, mice were given intraperitoneal injections of the respective control isotype antibodies (200 µg rat-IgG2a+100 µg rat-IgG2b); 200 µg α-PD1; 100 µg α-CTLA-4 or a combination of 200 µg α-PD1+100 µg α-CTLA-4. Tumor volumes are shown. Each line represents one mouse (n=11-12 mice per group, * P<0.01, ** P<0.005). Significance was determined using 2Way Anova tests. Data are representative of 2 (a) or pooled from 2 (b) independent experiments.

We next evaluated DPP4 inhibition in combination with adoptive T cell therapy. Due to B16F10 melanoma being refractory to Pmel-1 adoptive transfer[26], we employed an ovalbumin (OVA)-expressing line called M04 (B16F10 transfected with OVA) that can be recognized by CD8⁺ OT1 T lymphocytes[27]. Sitagliptin or adoptive cell transfer monotherapies (sitagliptin+PBS and control chow+OT1, respectively) both showed a significant delay in B16-OVA tumor growth (FIG. 7a). When used in combination, we observed a synergistic effect with >80% reduction in tumor size at day 15, as compared to the ~50% inhibition seen with either monotherapy regimen (p<0.01, FIG. 7a).

Figure 7B:
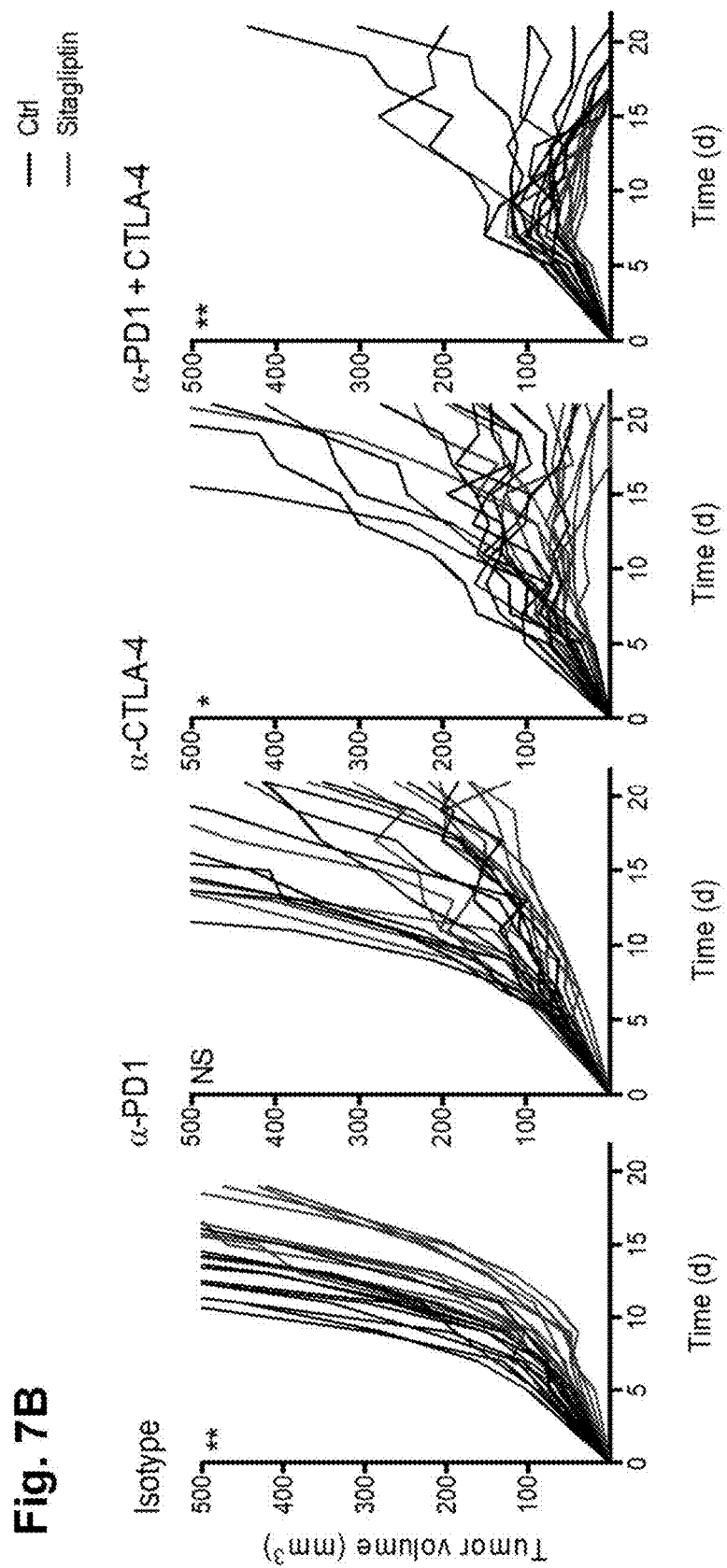

Finally, we studied the combination of sitagliptin and checkpoint blockade (anti-PD1 and anti-CTLA-4) using the CT26 tumor model. As shown above, sitagliptin monotherapy resulted in delayed CT26 growth (p=0.003, FIG. 7b). While combination of sitagliptin and anti-PD1 did not show improved tumor immunity as compared to anti-PD1 monotherapy, we did observe a significant delay in tumor growth for sitagliptin plus anti-CTLA-4 treatment as compared to anti-CTLA-4 alone (FIG. 7b). Most striking was triple therapy-sitagliptin given in combination with both CTLA-4 and PD1 antibodies—which resulted in 100% of the animals rejecting their tumor by day 21; whereas CTLA-4 plus PD1 antibody double-therapy only cured 42% of the mice during the same period of time (p=0.004, FIG. 7b). In summary, our data provides conclusive in vivo evidence that DPP4 regulates chemokine trafficking and that its inhibition can be used to enhance the response to current tumor immunotherapy regimens.

REFERENCES

1. Rot, A. & von Andrian, U. H. Chemokines in innate and adaptive host defense: basic chemokinese grammar for immune cells. *Annu Rev Immunol* 22, 891-928 (2004).
2. Weber, M., et al. Interstitial dendritic cell guidance by haptotactic chemokine gradients. *Science* 339, 328-332 (2013).
3. Mortier, A., Van Damme, J. & Proost, P. Overview of the mechanisms regulating chemokine activity and availability. *Immunol Lett* 145, 2-9 (2012).
4. Proost, P., et al. Amino-terminal truncation of CXCR3 agonists impairs receptor signaling and lymphocyte chemotaxis, while preserving antiangiogenic properties. *Blood* 98, 3554-3561 (2001).
5. Bongers, J., Lambros, T., Ahmad, M. & Heimer, E. P. Kinetics of dipeptidyl peptidase IV proteolysis of growth hormone-releasing factor and analogs. *Biochim Biophys Acta* 1122, 147-153 (1992).
6. Durinx, C., et al. Molecular characterization of dipeptidyl peptidase activity in serum: soluble CD26/dipeptidyl peptidase IV is responsible for the release of X-Pro dipeptides. *Eur J Biochem* 267, 5608-5613 (2000).
7. Stecca, B. A., et al. Aberrant dipeptidyl peptidase IV (DPP IV/CD26) expression in human hepatocellular carcinoma. *J Hepatol* 27, 337-345 (1997).
8. Kajiyama, H., et al. Increased expression of dipeptidyl peptidase IV in human mesothelial cells by malignant ascites from ovarian carcinoma patients. *Oncology* 63, 158-165 (2002).
9. Karagiannis, T., Boura, P. & Tsapas, A. Safety of dipeptidyl peptidase 4 inhibitors: a perspective review. *Ther Adv Drug Saf* 5, 138-146 (2014).
10. Lambeir, A. M., et al. Kinetic investigation of chemokine truncation by CD26/dipeptidyl peptidase IV reveals a striking selectivity within the chemokine family. *J Biol Chem* 276, 29839-29845 (2001).
11. Casrouge, A., et al. Evidence for an antagonist form of the chemokine CXCL10 in patients chronically infected with HCV. *J Clin Invest* 121, 308-317 (2011).
12. Riva, A., et al. Truncated CXCL10 is associated with failure to achieve spontaneous clearance of acute hepatitis C infection. *Hepatology* 60, 487-496 (2014).
13. Ragab, D., et al. CXCL10 antagonism and plasma sDPPIV correlate with increasing liver disease in chronic HCV genotype 4 infected patients. *Cytokine* 63, 105-112 (2013).
14. Christopherson, K. W., 2nd, Cooper, S. & Broxmeyer, H. E. Cell surface peptidase CD26/DPPIV mediates G-CSF mobilization of mouse progenitor cells. *Blood* 101, 4680-4686 (2003).
15. Oravecz, T., et al. Regulation of the receptor specificity and function of the chemokine RANTES (regulated on activation, normal T cell expressed and secreted) by dipeptidyl peptidase IV (CD26)-mediated cleavage. *J Exp Med* 186, 1865-1872 (1997).
16. Fridman, W. H., et al. Prognostic and predictive impact of intra- and peritumoral immune infiltrates. *Cancer Res* 71, 5601-5605 (2011).
17. Pages, F., et al. Immune infiltration in human tumors: a prognostic factor that should not be ignored. *Oncogene* 29, 1093-1102 (2010).
18. Mortier, A., Gouwy, M., Van Damme, J. & Proost, P. Effect of posttranslational processing on the in vitro and in vivo activity of chemokines. *Exp Cell Res* 317, 642-654 (2011).
19. Strieter, R. M., Kunkel, S. L., Arenberg, D. A., Burdick, M. D. &r Polverini, P. J. Interferon gamma-inducible protein 10 (IP-10), a member of the C-X-C chemokine family, is an inhibitor of angiogenesis. *Biochem Biophys Res Commun* 210, 51-57 (1995).
20. Christopherson, K. W., 2nd, Hangoc, G., Mantel, C. R. & Broxmeyer, H. E. Modulation of hematopoietic stem cell homing and engraftment by CD26. *Science* 305, 1000-1003 (2004).
21. Forssmann, U., et al. Inhibition of CD26/dipeptidyl peptidase IV enhances CCL11/eotaxin-mediated recruitment of eosinophils in vivo. *J Immunol* 181, 1120-1127 (2008).
22. Bonecchi, R., et al. Differential recognition and scavenging of native and truncated macrophage-derived chemokine (macrophage-derived chemokine/CC chemokine ligand 22) by the D6 decoy receptor. *J Immunol* 172, 4972-4976 (2004).
23. Loetscher, P., et al. The ligands of CXC chemokine receptor 3, I-TAC, Mig, and IP10, are natural antagonists for CCR3. *J Biol Chem* 276, 2986-2991 (2001).
24. Pashenkov, M., et al. Phase II trial of a toll-like receptor 9-activating oligonucleotide in patients with metastatic melanoma. *J Clin Oncol* 24, 5716-5724 (2006).

25. Krieg, A. M. CpG still rocks! Update on an accidental drug. *Nucleic Acid Ther* 22, 77-89 (2012).
26. Overwijk, W. W., et al. Tumor regression and autoimmunity after reversal of a functionally tolerant state of self-reactive CD8+ T cells. *J Exp Med* 198, 569-580 (2003).
27. Budhu, S., et al. CD8+ T cell concentration determines their efficiency in killing cognate antigen-expressing syngeneic mammalian cells in vitro and in mouse tissues. *J Exp Med* 207, 223-235 (2010).
28. Gorrell, M. D., et al. Structure and function in dipeptidyl peptidase IV and related proteins. *Adv Exp Med Biol* 575, 45-54 (2006).
29. Wilson, M. J., et al. Elevation of dipeptidylpeptidase iv activities in the prostate peripheral zone and prostatic secretions of men with prostate cancer: possible prostate cancer disease marker. *J Urol* 174, 1124-1128 (2005).
30. Ou, X., O'Leary, H. A. & Broxmeyer, H. E. Implications of DPP4 modification of proteins that regulate stem/progenitor and more mature cell types. *Blood* 122, 161-169 (2013).
31. Antonsson, B., De Lys, P., Dechavanne, V., Chevalet, L. & Boschert, U. In vivo processing of CXCL12alpha/SDF-1alpha after intravenous and subcutaneous administration to mice. *Proteomics* 10, 4342-4351 (2010).
32. Favre-Kontula, L., et al. Quantitative detection of therapeutic proteins and their metabolites in serum using antibody-coupled ProteinChip Arrays and SELDI-TOF-MS. *J Immunol Methods* 317, 152-162 (2006).
33. Carbone, A., et al. The expression of CD26 and CD40 ligand is mutually exclusive in human T-cell non-Hodgkin's lymphomas/leukemias. *Blood* 86, 4617-4626 (1995).
34. Kacar, A., et al. Stromal expression of CD34, alpha-smooth muscle actin and CD26/DPPIV in squamous cell carcinoma of the skin: a comparative immunohistochemical study. *Pathol Oncol Res* 18, 25-31 (2012).
35. Adams, S., et al. PT-100, a small molecule dipeptidyl peptidase inhibitor, has potent antitumor effects and augments antibody-mediated cytotoxicity via a novel immune mechanism. *Cancer Res* 64, 5471-5480 (2004).
36. Santos, A. M., Jung, J., Aziz, N., Kissil, J. L. & Pure, E. Targeting fibroblast activation protein inhibits tumor stromagenesis and growth in mice. *J Clin Invest* 119, 3613-3625 (2009).
37. Arwert, E. N., et al. Upregulation of CD26 expression in epithelial cells and stromal cells during wound-induced skin tumour formation. *Oncogene* 31, 992-1000 (2012).
38. Lee, J., Fassnacht, M., Nair, S., Boczkowski, D. & Gilboa, E. Tumor immunotherapy targeting fibroblast activation protein, a product expressed in tumor-associated fibroblasts. *Cancer Res* 65, 11156-11163 (2005).
39. Moelants, E. A., Mortier, A., Van Damme, J. & Proost, P. In vivo regulation of chemokine activity by post-translational modification. *Immunol Cell Biol* 91, 402-407 (2013).
40. Mortier, A., et al. Posttranslational modification of the NH2-terminal region of CXCL5 by proteases or peptidylarginine Deiminases (PAD) differently affects its biological activity. *J Biol Chem* 285, 29750-29759 (2010).
41. Ehlert, J. E., Gerdes, J., Flad, H. D. & Brandt, E. Novel C-terminally truncated isoforms of the CXC chemokine beta-thromboglobulin and their impact on neutrophil functions. *J Immunol* 161, 4975-4982 (1998).
42. Van den Steen, P. E., Husson, S. J., Proost, P., Van Damme, J. & Opdenakker, G. Carboxyterminal cleavage of the chemokines MIG and IP-10 by gelatinase B and neutrophil collagenase. *Biochem Biophys Res Commun* 310, 889-896 (2003).
43. Loos, T., et al. Citrullination of CXCL10 and CXCL11 by peptidylarginine deiminase: a naturally occurring post-translational modification of chemokines and new dimension of immunoregulation. *Blood* 112, 2648-2656 (2008).
44. Hodi, F. S., et al. Improved survival with ipilimumab in patients with metastatic melanoma. *The New England journal of medicine* 363, 711-723 (2010).
45. Kerkar, S. P. & Restifo, N. P. Cellular constituents of immune escape within the tumor microenvironment. *Cancer Res* 72, 3125-3130 (2012).
46. Schmitt, T. M., Ragnarsson, G. B. & Greenberg, P. D. T cell receptor gene therapy for cancer. *Hum Gene Ther* 20, 1240-1248 (2009).
47. June, C. H. Adoptive T cell therapy for cancer in the clinic. *J Clin Invest* 117, 1466-1476 (2007).
48. Gattinoni, L., Powell, D. J., Jr., Rosenberg, S. A. & Restifo, N. P. Adoptive immunotherapy for cancer: building on success. *Nat Rev Immunol* 6, 383-393 (2006).
49. Leach, D. R., Krummel, M. F. & Allison, J. P. Enhancement of antitumor immunity by CTLA-4 blockade. *Science* 271, 1734-1736 (1996).
50. Iwai, Y., et al. Involvement of PD-L1 on tumor cells in the escape from host immune system and tumor immunotherapy by PD-L1 blockade. *Proc Natl Acad Sci USA* 99, 12293-12297 (2002).

The invention claimed is:

1. A method of treating colon cancer in a subject in need thereof, comprising:
   administering a Dipeptidylpeptidase 4 (DPP4) inhibitor selected from Sitagliptin, Vildagliptin, Saxagliptin, Linagliptin, Anagliptin, Teneligliptin, Alogliptin, Gemigliptin, Dutogliptin, Trelagliptin, Omarigliptin, Carmegliptin, Denagliptin, 2-[4-{{2-(2S,5R)-2-cyano-5-ethynyl-1-pyrrolidinyl]-2-oxoethyl]amino]-4-methyl-1-piperidinyl]-4-pyridinecarboxylic acid, (4R, 5S)-5-amino-4-(2,4,5-trifluorophenyl) cyclohex-1-enyl)-(3-(trifluoromethyl)-5,6-dihydro-[1,2,4] triazolo [4,3-a]pyrazine-7(8H)-yl) methanone, or Lupeol; and
   administering Nivolumab or Ipilimumab to the subject.

2. The method of claim 1 comprising administering Ipilimumab to the subject.

3. The method of claim 2 comprising administering Nivolumab and Ipilimumab to the subject.

4. The method of claim 1, wherein the DPP4 inhibitor is selected from Trelagliptin, Sitagliptin, Vildagliptin, Saxagliptin, Alogliptin, Carmegliptin, Denagliptin, 2-[4-{{2-(2S, 5R)-2-cyano-5-ethynyl-1-pyrrolidinyl]-2-oxoethyl]amino]-4-methyl-1-piperidinyl]-4-pyridinecarboxylic acid (4R, 5S)-5-amino-4-(2,4,5-trifluorophenyl) cyclohex-1-enyl)-(3-(trifluoromethyl)-5,6-dihydro-[1,2,4] triazolo [4,3-a] pyrazine-7(8H)-yl) methanone, and Linagliptin.

5. The method of claim 4, wherein the DPP4 inhibitor is selected from Sitagliptin, Linagliptin, Carmegliptin, Denagliptin, 2-[4-{{2-(2S,5R)-2-cyano-5-ethynyl-1-pyrrolidinyl]-2-oxoethyl]amino]-4-methyl-1-piperidinyl]-4-pyridinecarboxylic acid, (4R, 5S)-5-amino-4-(2,4,5-trifluorophenyl) cyclohex-1-enyl)-(3-(trifluoromethyl)-5,6-dihydro-[1,2,4] triazolo [4,3-a]pyrazine-7(8H)-yl) methanone, and Alogliptin.

6. The method of claim 5, wherein the DPP4 inhibitor is selected from Sitagliptin, Linagliptin, and Alogliptin.

7. The method of claim 6, wherein the DPP4 inhibitor is Sitagliptin.

8. The method of claim 6, wherein the DPP4 inhibitor is Linagliptin.

9. The method of claim 6, wherein the DPP4 inhibitor is Alogliptin.

10. The method of claim 2, wherein the DPP4 inhibitor is selected from Trelagliptin, Sitagliptin, Vildagliptin, Saxagliptin, Alogliptin, Carmegliptin, Denagliptin, 2-[4-{{2-(2S, 5R)-2-cyano-5-ethynyl-1-pyrrolidinyl]-2-oxoethyl]amino]-4-methyl-1-piperidinyl]-4-pyridinecarboxylic acid, (4R, 5S)-5-amino-4-(2,4,5-trifluorophenyl) cyclohex-1-enyl)-(3-(trifluoromethyl)-5,6-dihydro-[1,2,4] triazolo [4,3-a]pyrazine-7(8H)-yl) methanone, and Linagliptin.

11. The method of claim 10, wherein the DPP4 inhibitor is selected from Sitagliptin, Linagliptin, Carmegliptin, Denagliptin, 2-[4-{{2-(2S,5R)-2-cyano-5-ethynyl-1-pyrrolidinyl]-2-oxoethyl]amino]-4-methyl-1-piperidinyl]-4-pyridinecarboxylic acid, (4R, 5S)-5-amino-4-(2,4,5-trifluorophenyl) cyclohex-1-enyl)-(3-(trifluoromethyl)-5,6-dihydro-[1,2,4] triazolo [4,3-a]pyrazine-7(8H)-yl) methanone, and Alogliptin.

12. The method of claim 11, wherein the DPP4 inhibitor is selected from Sitagliptin, Linagliptin, and Alogliptin.

13. The method of claim 12, wherein the DPP4 inhibitor is Sitagliptin.

14. The method of claim 12, wherein the DPP4 inhibitor is Linagliptin.

15. The method of claim 12, wherein the DPP4 inhibitor is Alogliptin.

16. The method of claim 3, wherein the DPP4 inhibitor is selected from Trelagliptin, Sitagliptin, Vildagliptin, Saxagliptin, Alogliptin, Carmegliptin, Denagliptin, 2-[4-{{2-(2S, 5R)-2-cyano-5-ethynyl-1-pyrrolidinyl]-2-oxoethyl]amino]-4-methyl-1-piperidinyl]-4-pyridinecarboxylic acid, (4R, 5S)-5-amino-4-(2,4,5-trifluorophenyl) cyclohex-1-enyl)-(3-(trifluoromethyl)-5,6-dihydro-[1,2,4] triazolo [4,3-a]pyrazine-7(8H)-yl) methanone, and Linagliptin.

17. The method of claim 16, wherein the DPP4 inhibitor is selected from Sitagliptin, Linagliptin, Carmegliptin, Denagliptin, 2-[4-{{2-(2S,5R)-2-cyano-5-ethynyl-1-pyrrolidinyl]-2-oxoethyl]amino]-4-methyl-1-piperidinyl]-4-pyridinecarboxylic acid, (4R, 5S)-5-amino-4-(2,4,5-trifluorophenyl) cyclohex-1-enyl)-(3-(trifluoromethyl)-5,6-dihydro-[1,2,4] triazolo [4,3-a]pyrazine-7(8H)-yl) methanone, and Alogliptin.

18. The method of claim 17, wherein the DPP4 inhibitor is selected from Sitagliptin, Linagliptin, and Alogliptin.

19. The method of claim 18, wherein the DPP4 inhibitor is Sitagliptin.

20. The method of claim 18, wherein the DPP4 inhibitor is Linagliptin.

21. The method of claim 18, wherein the DPP4 inhibitor is Alogliptin.

\* \* \* \* \*